(12) United States Patent
Wei

(10) Patent No.: US 11,371,011 B2
(45) Date of Patent: Jun. 28, 2022

(54) BENEFICIAL MICROBES FOR DELIVERY OF EFFECTOR PEPTIDES OR PROTEINS AND USE THEREOF

(71) Applicant: Plant Health Care, Inc., Raleigh, NC (US)

(72) Inventor: Zhongmin Wei, Kirkland, WA (US)

(73) Assignee: PLANT HEALTH CARE, INC., Raleigh, NC (US)

( * ) Notice: Subject to any disclaimer, the term of this patent is extended or adjusted under 35 U.S.C. 154(b) by 0 days.

(21) Appl. No.: 15/476,257

(22) Filed: Mar. 31, 2017

(65) Prior Publication Data

US 2017/0292108 A1    Oct. 12, 2017

Related U.S. Application Data

(60) Provisional application No. 62/319,150, filed on Apr. 6, 2016.

(51) Int. Cl.
| | | |
|---|---|---|
| *C12N 1/21* | (2006.01) | |
| *C12N 1/20* | (2006.01) | |
| *C07K 14/27* | (2006.01) | |
| *C07K 14/32* | (2006.01) | |
| *C12N 1/14* | (2006.01) | |

(52) U.S. Cl.
CPC ............... *C12N 1/20* (2013.01); *C07K 14/27* (2013.01); *C07K 14/32* (2013.01); *C12N 1/14* (2013.01)

(58) Field of Classification Search
None
See application file for complete search history.

(56) References Cited

U.S. PATENT DOCUMENTS

| | | | | |
|---|---|---|---|---|
| 4,751,081 | A * | 6/1988 | Suslow | A01N 63/00 424/93.2 |
| 5,473,039 | A | 12/1995 | Dyer et al. | |
| 5,776,889 | A | 7/1998 | Wei et al. | |
| 5,859,339 | A | 1/1999 | Ronald et al. | |
| 5,977,060 | A | 11/1999 | Zitter et al. | |
| 6,235,974 | B1 | 5/2001 | Qiu et al. | |
| 6,262,018 | B1 * | 7/2001 | Kim | C07K 14/27 514/3.3 |
| 6,277,814 | B1 | 8/2001 | Qiu et al. | |
| 6,310,176 | B1 | 10/2001 | Barra et al. | |
| 6,563,020 | B1 | 5/2003 | Simmons et al. | |
| 6,596,509 | B1 * | 7/2003 | Bauer | C07K 14/21 435/252.3 |
| 6,624,139 | B1 | 9/2003 | Wei et al. | |
| 6,858,707 | B1 | 2/2005 | Wei et al. | |
| 7,132,393 | B2 | 11/2006 | Summerton | |
| 7,132,525 | B2 | 11/2006 | Laby et al. | |
| 8,440,881 | B2 | 5/2013 | Park et al. | |
| 8,686,224 | B2 | 4/2014 | Ryan et al. | |
| 9,109,039 | B2 | 8/2015 | Ryan et al. | |
| 2002/0007501 | A1 | 1/2002 | Song et al. | |
| 2002/0019337 | A1 | 2/2002 | Wei et al. | |
| 2002/0062500 | A1 | 2/2002 | Fan et al. | |
| 2002/0059658 | A1 | 5/2002 | Wei et al. | |
| 2003/0104979 | A1 | 6/2003 | Wei et al. | |
| 2004/0016029 | A1 | 1/2004 | Wei | |
| 2004/0073977 | A1 | 4/2004 | Misra | |
| 2005/0250699 | A1 | 10/2005 | Kristensen et al. | |
| 2006/0248617 | A1 | 11/2006 | Imanaka et al. | |
| 2007/0154449 | A1 | 7/2007 | Cue et al. | |
| 2009/0118134 | A1 | 5/2009 | Vrijloeb et al. | |
| 2009/0300802 | A1 | 12/2009 | Ryan et al. | |
| 2010/0043095 | A1 | 2/2010 | Wei | |
| 2010/0064386 | A1 | 3/2010 | Park et al. | |
| 2011/0191896 | A1 | 8/2011 | Pitkin et al. | |
| 2011/0233469 | A1 | 9/2011 | Petersen | |
| 2012/0265513 | A1 | 10/2012 | Fang et al. | |
| 2013/0116119 | A1 | 5/2013 | Rees et al. | |
| 2013/0125258 | A1 | 5/2013 | Emmanuel et al. | |
| 2013/0150288 | A1 | 6/2013 | Dobson | |

(Continued)

FOREIGN PATENT DOCUMENTS

| | | |
|---|---|---|
| CN | 1793172 | 6/2006 |
| CN | 101284876 | 10/2008 |

(Continued)

OTHER PUBLICATIONS

Kunze et al. (The Plant Cell 16.12 (2004): 3496-3507). (Year: 2004).*
Wang et al. (BioControl 56.1 (2011): 113-121). (Year: 2011).*
Kim et al. (Journal of bacteriology 186.18 (2004): 6239-6247). (Year: 2004).*
Wu et al. (J Microbiol Biotechnol 19.2 (2009): 194-203). (Year: 2009).*
Xie et al (Molecular Plant-Microbe Interactions 27.7 (2014): 655-663). (Year: 2014).*
International Search Report and Written Opinion for PCT/US17/25483 dated Sep. 11, 2017.

(Continued)

*Primary Examiner* — Charles Logsdon
(74) *Attorney, Agent, or Firm* — Troutman Pepper Hamilton Sanders LLP (Rochester)

(57) ABSTRACT

Disclosed are recombinant host cells comprising a promoter-effective nucleic acid molecule operably coupled to a nucleic acid molecule that encodes a plant effector protein or polypeptide that induces an active plant response including, among others, growth enhancement, disease resistance, pest or insect resistance, and stress resistance. Use of these recombinant host cells for modulating plant biochemical signaling, imparting disease resistance to plants, enhancing plant growth, imparting tolerance to biotic stress, imparting tolerance and resistance to abiotic stress, imparting desiccation resistance to cuttings removed from ornamental plants, imparting post-harvest disease or post-harvest desiccation resistance to a fruit or vegetable, or enhancing the longevity of fruit or vegetable ripeness are also disclosed.

31 Claims, No Drawings
Specification includes a Sequence Listing.

(56) References Cited

U.S. PATENT DOCUMENTS

| | | |
|---|---|---|
| 2013/0172185 A1 | 7/2013 | Wei |
| 2013/0274104 A1 | 10/2013 | Reddig et al. |
| 2013/0298287 A1 | 11/2013 | Park et al. |
| 2014/0090103 A1 | 3/2014 | Pitkin et al. |
| 2014/0227767 A2 | 8/2014 | Yeaman et al. |
| 2015/0218099 A1 | 8/2015 | Mann |
| 2016/0095314 A1 | 4/2016 | Wei et al. |
| 2016/0095315 A1 | 4/2016 | Wei et al. |
| 2016/0145310 A1 | 5/2016 | Wei et al. |
| 2016/0297853 A1 | 10/2016 | Wei et al. |
| 2016/0353735 A1 | 12/2016 | Wei et al. |
| 2016/0353736 A1 | 12/2016 | Wei et al. |

FOREIGN PATENT DOCUMENTS

| | | |
|---|---|---|
| CN | 101892244 | 11/2010 |
| CN | 103103202 | 5/2013 |
| CN | 1454989 | 11/2013 |
| CN | 106831964 | 6/2017 |
| EP | 1930025 | 6/2008 |
| EP | 1997502 | 12/2008 |
| EP | 2168592 | 3/2010 |
| EP | 2243487 A1 | 10/2010 |
| EP | 2553102 B1 | 12/2015 |
| WO | 95/31564 | 11/1995 |
| WO | 98/06748 | 2/1998 |
| WO | 99/02655 | 7/1998 |
| WO | 99/37664 | 7/1999 |
| WO | 2000002996 A2 | 1/2000 |
| WO | 00/020452 | 4/2000 |
| WO | 00/28056 | 5/2000 |
| WO | 01/055335 | 8/2001 |
| WO | 01/80639 | 11/2001 |
| WO | 01/98501 A1 | 12/2001 |
| WO | 2001/098501 | 12/2001 |
| WO | 2002/022821 | 3/2002 |
| WO | 2005/017158 | 2/2005 |
| WO | 2006/077601 | 7/2006 |
| WO | 2008/104598 | 9/2008 |
| WO | 2010/019442 | 2/2010 |
| WO | 2010/042654 | 4/2010 |
| WO | 2013/102189 | 7/2013 |
| WO | 2016044655 A2 | 3/2016 |

OTHER PUBLICATIONS

Solar et al., "Replication and Control of Circular Bacterial Plasmids," Microbiology and Molecular Biology Reviews 62(2):434-64 (1998).
Zhang et al., "Insecticidal Effect of Recombinant Endophytic Bacterium Containing Pineilia Ternata Agglutinin Against White Backed Planthopper, Sogatella Furcifera," Crop Protection 30(11):1478-84 (2011).
Bauer et al., "Erwinia Chrysanthemi HarpinEch: An Elicitor of the Hypersensitive Response that Contributes to Soft-Rot Pathogenesis," Molecular Plant-Microbe Interactions 8(4):484-91 (1995).
Kim et al., "Mutational Analysis of Xanthomonas Harpin HpaG Identifies a Key Functional Region That Elicits the Hypersensitive Response in Nonhost Plants," J. Bacteriol. 186(18):6239-6247 (2004).
Ji et al., "Two Coiled-Coil Regions of *Xanthomonas oryzae* pv. Oryzae Harpin Differ in Oligomerization and Hypersensitive Response Induction," Amino Acids 40:381-392 (2011).
Haapalainen et al., "Functional Mapping of Harpin HrpZ of Pseudomonas syringae Reveals the Sites Responsible for Protein Oligomerization, Lipid Interactions, and Plant Defence Induction," Mol. Plant Pathol. 12(2):151-66 (2011).
Lilie et al., "Polyionic and Cysteine-Containing Fusion Peptides as Versatile Protein Tags," Biol. Chem. 394 (8):995-1004 (2013).
Li et al., "Complete Regression of Well-Established Tumors Using a Novel Water-Soluble Poly(L-Glutamic Acid)-Paclitaxel Conjugate," Cancer Res. 58: 2404-2409 (1998).

Arlat et al., "PopA1, a Protein Which Induces a Hypersensitivity-like Response on Specific Petunia Genotypes, is Secreted via the Hrp Pathway of Pseudomonas solanacearum," The EMBO J. 13(3):543-553 (1994).
CAS RN 208293-02-1 (2000).
Chen et al., "Identification of Specific Fragments of HpaG Xooc, a Harpin for *Xanthomonas Oryzae* Pv. Oryzicola, That Induce Disease Resistance and Enhance Growth in Plants," Phytopathology 98(7):781-791 (2008).
Choi et al., "Harpins, Multifunctional Proteins Secreted by Gram-Negative Plant-Pathogenic Bacteria," Molecular Plant-Microbe Interactions 26(10):1115-1122 (2013).
Gentilucci et al., "Chemical Modifications Designed to Improve Peptide Stability: Incorporation of Non-Natural Amino Acids, Pseudo-Peptide Bonds, and Cyclization," Current Pharmaceutical Design 16(28):3185-3203 (2010).
Zeitler et al., "De-Novo Design of Antimicrobial Peptides for Plant Protection," PLOS ONE 8(8):e71687 (2013).
Kim et al., "HrpW of Erwinia Amylovora, a New Harpin That Contains a Domain Homologous to Pectate Lyases of a Distinct Class," J. Bacteriol. 180(19):5203-5210 (1998).
Maget-Dana et al., "Amphiphilic Peptides as Models for Protein-Membrane Interactions: Interfacial Behaviour of Sequential Lys- and Leu-Based Peptides and Their Penetration Into Lipid Monolayers," Supramolecular Sci. 4:365-368 (1997).
Miao et al., "HpaXm from *Xanthomonas citri* Subsp. Malvacearum is a Novel Harpin With Two Heptads for Hypersensitive Response," Journal of Microbiology and Biotechnology 20(1):54-62 (2010).
Mur et al., "The Hypersensitive Response; The Centenary is Upon Us But How Much Do We Know?," Journal of Experimental Botany 59(3):501-520 (2007).
Niv et al., "New Lytic Peptides Based on the D, L-Amphipathic Helix Motif Preferentially Kill Tumor Cells Compared to Normal Cells," Biochemistry, American Chemical Society 42(31):9346-9354 (2003).
Oliveira et al., "Induced Resistance During the Interaction Pathogen x Plant and the Use of Resistance Inducers," Phytochemistry Letters 15:152-158 (2016).
Olsen et al., "Trypsin Cleaves Exclusively C-Terminal to Arginine and Lysine Residues," Mol. and Cell. Proteomics 3.6 3:608-614 (2004).
Osusky et al., "Transgenic Potatoes Expressing a Novel Cationic Peptide are Resistant to Late Blight and Pink Rot," Transgenic Research 13(2):181-190 (2004).
Park et al., "Helix Stability Confers Salt Resistance Upon Helical Antimicrobial Peptides," J. Biol. Chem. 279:13896-13901 (2004).
Saito et al., "Synthesis of a Peptide Emulsifier With an Amphiphilic Structure," Bioscience, Biotechnology, and Biochemistry 59:388-392 (1995).
Slechtova et al., "Insight into Trypsin Miscleavage: Comparison of Kinetic Constants of Problematic Peptide Sequences," Analytical Chemistry 87:7636-7643 (2015).
Trevino et al., "Measuring and Increasing Protein Solubility," Journal of Pharmaceutical Sciences 97 (10):4155-4166 (2008).
Van Loon et al., "Systemic Resistance Induced by Rhizosphere Bacteria," Annu. Rev. Phytopathol. 36:453-83 (1998).
Yevtushenko et al., "Comparison of Pathogen-Induced Expression and Efficacy of Two Amphibian Antimicrobial Peptides, MsrA2 and Temporin A, for Engineering Wide-Spectrum Disease Resistance in Tobacco," Plant Biotechnology Journal 5(6):720-734 (2007).
NCBI Reference No. WP_082338630 (Apr. 11, 2017).
NCBI Reference No. WP_014505138.1 (May 19, 2017).
Inoue et al., "The HrpZ and HrpA Genes are Variable, and Useful for Grouping Pseudomonas Syringae Bacteria," Journal of General Plant Pathology 72(1):26-33 (2006).
Shenge et al., "Molecular Characterization of *Pseudomonas syringae* pv. Tomato Isolates From Tanzania," Phytoparasitica 36(4):338-351 (2008).
Shrestha et al., "The Hrp Gene Cluster in Erwinia Pyrifoliae and Determination of HR Active Domain in HrpNEp Protein," ISHS Acta Horticulturae 793: XI International Workshop on Fire Blight (2008).

(56) References Cited

OTHER PUBLICATIONS

Lee et al., "Relationship Between Antimicrobial Activity and Amphiphilic Property of Basic Model Peptides," Biochimica Biophysica Acta (BBA)—Biomembranes 862(1):211-219 (1986).
CAS RN 429026-68-6 (2002).
Wang et al., "Hpal is a Type III Translocator in *Xanthomonas oryzae* pv. Oryzae," BMC Microbiology (18):105 (2018).

\* cited by examiner

SEQUENCE LISTING

<160> NUMBER OF SEQ ID NOS: 49

<210> SEQ ID NO 1

```
<211> LENGTH: 469
<212> TYPE: DNA
<213> ORGANISM: Artificial
<220> FEATURE:
<223> OTHER INFORMATION: DNA construct for expression in B. subtilis

<400> SEQUENCE: 1
ggatcccaaa aatcagacca gacaaaagcg gcaaatgaat aagcggaacg gggaaggatt      60
tgcggtcaag tccttccctt ccgcacgtat caattcgcaa gcttttcctt tataatagaa     120
tgaatgaaaa ggaggaaaca atcatgtttg caaaaagatt taaaacatca ctgctgccgc     180
tgtttgcagg ctttctgctg ctgtttcatc tggttctggc aggcccggca gcagcatcag     240
cagaaacagc aaataaatca aatgaaaatt ttggcacacc ggattcaaca gttcaaaatc     300
cgcaagatgc atcaaaaccg aatgattcac aatcaaatat tgcaaaactg atttcagcac     360
tgattatgtc actgctgcaa atgtaaccag gcatcaaata aaacgaaagg ctcagtcgaa     420
agactgggcc tttcgtttta tctgttgttt gtcggtgaac gctctcgag               469

<210> SEQ ID NO 2
<211> LENGTH: 2156
<212> TYPE: DNA
<213> ORGANISM: Artificial
<220> FEATURE:
<223> OTHER INFORMATION: DNA construct for expression in Trichoderma
      reesei

<400> SEQUENCE: 2
tctagagttg tgaagtcggt aatcccgctg tatagtaata cgagtcgcat ctaaatactc      60
cgaagctgct gcgaacccgg agaatcgaga tgtgctggaa agcttctagc gagcggctaa     120
attagcatga aaggctatga gaaattctgg agacggcttg ttgaatcatg gcgttccatt     180
cttcgacaag caaagcgttc cgtcgcagta gcaggcactc attcccgaaa aaactcggag     240
attcctaagt agcgatggaa ccggaataat ataataggca atacattgag ttgcctcgac     300
ggttgcaatg caggggtact gagcttggac ataactgttc cgtaccccac ctcttctcaa     360
cctttggcgt ttccctgatt cagcgtaccc gtacaagtcg taatcactat taacccagac     420
tgaccggacg tgttttgccc ttcatttgga gaaataatgt cattgcgatg tgtaatttgc     480
ctgcttgacc gactggggct gttcgaagcc cgaatgtagg attgttatcc gaactctgct     540
cgtagaggca tgttgtgaat ctgtgtcggg caggacacgc ctcgaaggtt cacggcaagg     600
gaaaccaccg atagcagtgt ctagtagcaa cctgtaaagc cgcaatgcag catcactgga     660
aaatacaaac caatggctaa aagtacataa gttaatgcct aaaggagtca tataccagcg     720
gctaataatt gtacaatcaa gtggctaaac gtaccgtaat ttgccaacgg cttgtggggt     780
tgcagaagca acggcaaagc cccacttccc cacgtttgtt tcttcactca gtccaatctc     840
agctggtgat cccccaattg ggtcgcttgt ttgttccggt gaagtgaaag aagacagagg     900
taagaatgtc tgactcggag cgttttgcat acaaccaagg gcagtgatgg aagacagtga     960
aatgttgaca ttcaaggagt atttagccag ggatgcttga gtgtatcgtg taaggaggtt    1020
tgtctgccga tacgacgaat actgtatagt cacttctgat gaagtggtcc atattgaaat    1080
gtaagtcggc actgaacagg caaaagattg agttgaaact gcctaagatc tcgggccctc    1140
gggccttcgg cctttgggtg tacatgtttg tgctccgggc aaatgcaaag tgtggtagga    1200
tcgaacacac tgctgccttt accaagcagc tgagggtatg tgataggcaa atgttcaggg    1260
gccactgcat ggtttcgaat agaaagagaa gcttagccaa gaacaatagc cgataaagat    1320
```

```
agcctcatta aacggaatga gctagtaggc aaagtcagcg aatgtgtata tataaaggtt    1380
cgaggtccgt gcctccctca tgctctcccc atctactcat caactcagat cctccaggag    1440
acttgtacac catcttttga ggcacagaaa cccaatagtc aaccgcggac tggcatcatg    1500
tatcggaagt tggccgtcat ctcggccttc ttggccacag ctcaggccgg ccccagagc    1560 gccaacaaga ccggcaacgt cgacgacgcc aacaaccagg accccatgca ggccctcatg    1620
cagctcctcg aggacctcgt ctaaagctcc gtgcgaaagc ctgacgcacc ggtagattct    1680
tggtgagccc gtatcatgac ggcggcggga gctacatggc cccgggtgat ttattttttt    1740
tgtatctact tctgacccct ttcaaatata cggtcaactc atctttcact ggagatgcgg    1800
cctgcttggt attgcgatgt tgtcagcttg gcaaattgtg gctttcgaaa acacaaaacg    1860
attccttagt agccatgcat tttaagataa cggaatagaa gaagaggaa attaaaaaaa    1920 aaaaaaaac aaacatcccg ttcataaccc gtagaatcgc cgctcttcgt gtatcccagt    1980
accacggcaa aggtatttca tgatcgttca atgttgatat tgttcccgcc agtatggctc    2040 cacccccat ctccgcgaat ctcctcttct cgaacgcggt gtggcgcgcc aattggtaat    2100
gaccccatag ggagacaaac agcataatag caacagtgga aattagtggc gaattc        2156
```

<210> SEQ ID NO 3
<211> LENGTH: 17
<212> TYPE: PRT
<213> ORGANISM: Artificial
<220> FEATURE:
<223> OTHER INFORMATION: CBH I secretion signal

<400> SEQUENCE: 3

Met Tyr Arg Lys Leu Ala Val Ile Ser Ala Phe Leu Ala Thr Ala Arg
1               5                   10                  15

Ala

<210> SEQ ID NO 4
<211> LENGTH: 20
<212> TYPE: PRT
<213> ORGANISM: Artificial
<220> FEATURE:
<223> OTHER INFORMATION: Synthetic peptide

<400> SEQUENCE: 4

Ser Glu Glu Gln Leu Glu Leu Leu Leu Ala Phe Ile Ala Ala Ala Leu
1               5                   10                  15

Gln Gln Glu Glu
            20

<210> SEQ ID NO 5
<211> LENGTH: 17
<212> TYPE: PRT
<213> ORGANISM: Artificial
<220> FEATURE:
<223> OTHER INFORMATION: Synthetic peptide

<400> SEQUENCE: 5

Ser Gln Gly Ile Ser Glu Lys Gln Leu Asp Gln Leu Leu Ser Gln Leu
1               5                   10                  15

Ile

<210> SEQ ID NO 6
<211> LENGTH: 15
<212> TYPE: PRT
<213> ORGANISM: Artificial

<220> FEATURE:
<223> OTHER INFORMATION: Synthetic peptide

<400> SEQUENCE: 6

Leu Glu Glu Leu Leu Glu Glu Leu Ile Glu Glu Leu Leu Glu Glu
1               5                   10                  15

<210> SEQ ID NO 7
<211> LENGTH: 824
<212> TYPE: DNA
<213> ORGANISM: Artificial
<220> FEATURE:
<223> OTHER INFORMATION: Fresno-P30-3 insert

<400> SEQUENCE: 7

| | | | | | |
|---|---|---|---|---|---|
| taagtctact | ctgaacttaa | gcaaaaggag | agggacgcgt | atgaattcac | tgattaaaga | 60 |
| aaatatgcat | atgaaactgt | atatggaagg | cacagttaat | aatcatcatt | ttaaatgcac | 120 |
| atcagaaggc | gaaggcaaac | cgtatgaagg | cacacaaaca | atgagaatta | aagttgttga | 180 |
| aggcggcccg | ctgccgtttg | catttgatat | tctggcaaca | tcatttatgt | atggctcaag | 240 |
| aacatttatt | aaatatccga | aaggcattcc | ggatttttt | aaacaatcat | tccggaagg | 300 |
| ctttacatgg | gaaagagtta | caagatatga | agatggcggc | gttgttacag | caacacaaga | 360 |
| tacatcactg | gaagatggct | gcctggttta | tcatgttcaa | gttagaggcg | ttaattttcc | 420 |
| gtcaaatggc | ccggttatgc | aaaaaaaaac | actgggctgg | gaaccgaata | cagaaatgct | 480 |
| gtatccggca | gatggcggcc | tggaaggcag | atcagatatg | gcactgaaac | tggttggcgg | 540 |
| cggccatctg | tcatgctcat | tgttacaac | atatagatca | aaaaaaacag | ttggcaatat | 600 |
| taaaatgccg | ggcattcatg | cagttgatca | tagactggtt | agaattaaag | aagcagataa | 660 |
| agaaacatat | gttgaacaac | atgaagttgc | agttgcaaaa | tttgcaggcc | tgggcggcgg | 720 |
| catggatgaa | ctgtataaat | tagaggaact | gcttgaagaa | ttaattgaag | aattgctcga | 780 |
| agagtctaga | catcaccatc | atcaccacta | atgcggtagt | ttat | | 824 |

<210> SEQ ID NO 8
<211> LENGTH: 803
<212> TYPE: DNA
<213> ORGANISM: Artificial
<220> FEATURE:
<223> OTHER INFORMATION: Yukon-P30-3 insert

<400> SEQUENCE: 8

| | | | | | |
|---|---|---|---|---|---|
| taagtctact | ctgaacttaa | gcaaaaggag | agggacgcgt | atgtctcttt | ccaagcaggt | 60 |
| ccttccgcgt | gatgttcgta | tgagatttca | tatggatggg | tgtgttaatg | gacatcaatt | 120 |
| tactattgaa | ggtgaaggtg | ctgggaaacc | gtatgaaggt | aaaaaaacat | tgaaactgag | 180 |
| agtgacaaaa | ggtgggcctc | ttcccttcgc | cttcgatata | ctttcagcaa | catttacgta | 240 |
| tggcaatcgg | tgcttttgtg | attacccgga | agatatgccg | gactatttca | aacaaagttt | 300 |
| gccggaggga | tactcatggg | aacgaacgct | gatgtttgag | gatgggggtt | gcggcacagc | 360 |
| gtccgcgcac | atttcgttag | agaaagactg | tttcattcac | aacagcactt | tcatggggt | 420 |
| aaatttcccca | gcaaacggac | ctgtaatgca | gaaaaaaaca | ctgaattggg | aaccttcatc | 480 |
| cgagctgatt | acggcttgtg | atggcatcct | gaaggggggat | gtcacaatgt | ttttactgct | 540 |
| tgagggcgga | caccgattaa | agtgtcaatt | cacaacgtcc | tataaggccc | ataaggcagt | 600 |
| gaaaatgccg | ccgaatcata | ttattgaaca | tgtgctggta | aaaaaagagg | tcgccgacgg | 660 |
| tttccagatt | caggaacatg | ccgtcgcaaa | acatttacc | gtggatgtca | aggaaacatt | 720 |

```
agaggaactg cttgaagaat taattgaaga attgctcgaa gagtctagac atcaccatca    780
tcaccactaa tgcggtagtt tat                                           803
```

<210> SEQ ID NO 9  
<211> LENGTH: 830  
<212> TYPE: DNA  
<213> ORGANISM: Artificial  
<220> FEATURE:  
<223> OTHER INFORMATION: Fresno-P4-111 insert
<400> SEQUENCE: 9

```
taagtctact ctgaacttaa gcaaaaggag agggacgcgt atgaattcac tgattaaaga     60
aaatatgcat atgaaactgt atatggaagg cacagttaat aatcatcatt ttaaatgcac    120
atcagaaggc gaaggcaaac cgtatgaagg cacacaaaca atgagaatta agttgttga    180 aggcggcccg ctgccgtttg catttgatat tctggcaaca tcatttatgt atggctcaag    240
aacatttatt aaatatccga aaggcattcc ggatttttt aaacaatcat ttccggaagg    300
ctttacatgg gaaagagtta caagatatga agatggcggc gttgttacag caacacaaga    360
tacatcactg gaagatggct gcctggttta tcatgttcaa gttagaggcg ttaattttcc    420
gtcaaatggc ccggttatgc aaaaaaaaac actgggctgg aaccgaata cagaaatgct    480 gtatccggca gatggcggcc tggaaggcag atcagatatg gcactgaaac tggttggcgg    540
cggccatctg tcatgctcat tgttacaac atatagatca aaaaaaacag ttggcaatat    600
taaaatgccg ggcattcatg cagttgatca tagactggtt agaattaaag aagcagataa    660
agaaacatat gttgaacaac atgaagttgc agttgcaaaa tttgcaggcc tgggcggcgg    720
catggatgaa ctgtatataaat cgcaaggaat tagtgagaaa cagctagatc aactattatc    780
tcagctcata tctagacatc accatcatca ccactaatgc ggtagtttat                830
```

<210> SEQ ID NO 10  
<211> LENGTH: 809  
<212> TYPE: DNA  
<213> ORGANISM: Artificial  
<220> FEATURE:  
<223> OTHER INFORMATION: Yukon-P4-111 insert
<400> SEQUENCE: 10

```
taagtctact ctgaacttaa gcaaaaggag agggacgcgt atgtcactgt caaaacaagt     60
tctgccgaga gatgttagaa tgagatttca tatggatggc tgcgttaatg ccatcaatt    120 tacaattgaa ggcgaaggcg caggcaaacc gtatgaaggc aaaaaaacac tgaaactgag    180
agttacaaaa ggcggcccgc tgccgtttgc atttgatatt ctgtcagcaa catttacata    240
tggcaataga tgcttttgcg attatccgga agatatgccg gattatttta aacaatcact    300
gccggaaggc tattcatggg aaagaacact gatgtttgaa gatggcggct gcggcacagc    360
atcagcacat atttcactgg aaaaagattg ctttattcat aattcaacat tcatggcgt    420 taattttccg gcaaatggcc cggttatgca aaaaaaaaca ctgaattggg aaccgtcatc    480
agaactgatt acagcatgcg atggcattct gaaaggcgat gttacaatgt ttctgctgct    540
ggaaggcggc catagactga atgccaatt tacaacatca tataaagcac ataaagcagt    600
taaaatgccg ccgaatcata ttattgaaca tgttctggtt aaaaaagaag ttgcagatgg    660
ctttcaaatt caagaacatg cagttgcaaa acatttaca gttgatgtta aagaaacatc    720
gcaaggaatt agtgagaaac agctagatca actattatct cagctcatat ctagacatca    780
```

```
ccatcatcac cactaatgcg gtagtttat                                      809
```

<210> SEQ ID NO 11
<211> LENGTH: 839
<212> TYPE: DNA
<213> ORGANISM: Artificial
<220> FEATURE:
<223> OTHER INFORMATION: Fresno P5-21 insert

<400> SEQUENCE: 11

```
taagtctact ctgaacttaa gcaaaaggag agggacgcgt atgaatagtc ttatcaaaga     60
gaacatgcat atgaaactgt atatggaagg gacagtgaat aaccatcact tcaagtgtac    120
ctctgaagga gaagggaaac cgtatgaagg cacgcaaacg atgcgcatta aagtcgttga    180
aggcggaccc ttaccatttg cctttgacat tctggcaacg agctttatgt atggaagccg    240
gacttttatt aaatacccaa aaggcattcc agatttcttt aaacaaagct cccagaagg     300
gtttacatgg gaacgggtca caagatatga gacggcgga gtcgtgacgg caacacaaga    360
tacgagtctg gaagatggct gcttggtata tcatgtacaa gtcagaggag taaactttcc    420
gtctaacggc ccggtaatgc agaaaaagac tttagggtgg gaaccgaata cggagatgct    480
ttatcctgca gatgggggct tagaaggacg ctcagacatg gcgttaaaat tggtcggcgg    540
cggccatctt tcctgttctt tcgtgaccac ctatcgatct aagaaaactg tgggtaacat    600
caaaatgcca gggatccacg ctgtcgatca tcgtttagta agaatcaaag aagcggacaa    660
agaaacgtac gtcgaacagc atgaagtggc agttgctaaa tttgcaggtt taggaggcgg    720
tatgatgag ttgtacaagt cagaggaaca acttgaactg ttattagcat ttatcgcagc    780
cgcccttcaa caagaagaat ctagacatca ccatcatcac cactaatgcg gtagtttat    839
```

<210> SEQ ID NO 12
<211> LENGTH: 818
<212> TYPE: DNA
<213> ORGANISM: Artificial
<220> FEATURE:
<223> OTHER INFORMATION: Yukon-P5-21 insert

<400> SEQUENCE: 12

```
taagtctact ctgaacttaa gcaaaaggag agggacgcgt atgtctcttt ccaagcaggt     60
ccttccgcgt gatgttcgta tgagatttca tatggatggg tgtgttaatg gacatcaatt    120
tactattgaa ggtgaaggtg ctgggaaacc gtatgaaggt aaaaaaacat tgaaactgag    180
agtgacaaaa ggtgggcctc ttcccttcgc cttcgatata ctttcagcaa catttacgta    240
tggcaatcgg tgcttttgtg attacccgga agatatgccg gactatttca acaaagttt    300
gccggaggga tactcatggg aacgaacgct gatgtttgag gatgggggtt gcggcacagc    360
gtccgcgcac atttcgttag agaaagactg tttcattcac aacagcactt tcatggggt    420
aaatttcccca gcaaacggac ctgtaatgca gaaaaaaaca ctgaattggg aaccttcatc    480
cgagctgatt acggcttgtg atggcatcct gaagggggat gtcacaatgt tttactgct    540
tgagggcgga caccgattaa agtgtcaatt cacaacgtcc tataaggccc ataaggcagt    600
gaaaatgccg ccgaatcata ttattgaaca tgtgctggta aaaaaagagg tcgccgacgg    660
tttccagatt caggaacatg ccgtcgcaaa acatttttacc gtggatgtca aggaaacatc    720
agaggaacaa cttgaactgt tattagcatt tatcgcagcc gcccttcaac aagaagaatc    780
tagacatcac catcatcacc actaatgcgg tagtttat                            818
```

```
<210> SEQ ID NO 13
<211> LENGTH: 261
<212> TYPE: PRT
<213> ORGANISM: Artificial
<220> FEATURE:
<223> OTHER INFORMATION: Synthetic peptide

<400> SEQUENCE: 13

Met Asn Ser Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Met Tyr
    50                  55                  60

Gly Ser Arg Thr Phe Ile Lys Tyr Pro Lys Gly Ile Pro Asp Phe Phe
65                  70                  75                  80

Lys Gln Ser Phe Pro Glu Gly Phe Thr Trp Glu Arg Val Thr Arg Tyr
                85                  90                  95

Glu Asp Gly Gly Val Val Thr Ala Thr Gln Asp Thr Ser Leu Glu Asp
            100                 105                 110

Gly Cys Leu Val Tyr His Val Gln Val Arg Gly Val Asn Phe Pro Ser
        115                 120                 125

Asn Gly Pro Val Met Gln Lys Lys Thr Leu Gly Trp Glu Pro Asn Thr
    130                 135                 140

Glu Met Leu Tyr Pro Ala Asp Gly Gly Leu Glu Gly Arg Ser Asp Met
145                 150                 155                 160

Ala Leu Lys Leu Val Gly Gly His Leu Ser Cys Ser Phe Val Thr
                165                 170                 175

Thr Tyr Arg Ser Lys Lys Thr Val Gly Asn Ile Lys Met Pro Gly Ile
            180                 185                 190

His Ala Val Asp His Arg Leu Val Arg Ile Lys Glu Ala Asp Lys Glu
        195                 200                 205

Thr Tyr Val Glu Gln His Glu Val Ala Val Ala Lys Phe Ala Gly Leu
    210                 215                 220

Gly Gly Gly Met Asp Glu Leu Tyr Lys Ser Glu Glu Gln Leu Glu Leu
225                 230                 235                 240

Leu Leu Ala Phe Ile Ala Ala Leu Gln Gln Glu Glu Ser Arg His
                245                 250                 255

His His His His
        260

<210> SEQ ID NO 14
<211> LENGTH: 254
<212> TYPE: PRT
<213> ORGANISM: Artificial
<220> FEATURE:
<223> OTHER INFORMATION: Synthetic peptide

<400> SEQUENCE: 14

Met Ser Leu Ser Lys Gln Val Leu Pro Arg Asp Val Arg Met Arg Phe
1               5                   10                  15

His Met Asp Gly Cys Val Asn Gly His Gln Phe Thr Ile Glu Gly Glu
            20                  25                  30

Gly Ala Gly Lys Pro Tyr Glu Gly Lys Lys Thr Leu Lys Leu Arg Val
        35                  40                  45
```

Thr Lys Gly Gly Pro Leu Pro Phe Ala Phe Asp Ile Leu Ser Ala Thr
 50                  55                  60

Phe Thr Tyr Gly Asn Arg Cys Phe Cys Asp Tyr Pro Glu Asp Met Pro
 65                  70                  75                  80

Asp Tyr Phe Lys Gln Ser Leu Pro Glu Gly Tyr Ser Trp Glu Arg Thr
                 85                  90                  95

Leu Met Phe Glu Asp Gly Gly Cys Gly Thr Ala Ser Ala His Ile Ser
                100                 105                 110

Leu Glu Lys Asp Cys Phe Ile His Asn Ser Thr Phe His Gly Val Asn
            115                 120                 125

Phe Pro Ala Asn Gly Pro Val Met Gln Lys Lys Thr Leu Asn Trp Glu
130                 135                 140

Pro Ser Ser Glu Leu Ile Thr Ala Cys Asp Gly Ile Leu Lys Gly Asp
145                 150                 155                 160

Val Thr Met Phe Leu Leu Leu Glu Gly Gly His Arg Leu Lys Cys Gln
                165                 170                 175

Phe Thr Thr Ser Tyr Lys Ala His Lys Ala Val Lys Met Pro Pro Asn
                180                 185                 190

His Ile Ile Glu His Val Leu Val Lys Lys Glu Val Ala Asp Gly Phe
            195                 200                 205

Gln Ile Gln Glu His Ala Val Ala Lys His Phe Thr Val Asp Val Lys
210                 215                 220

Glu Thr Ser Glu Glu Gln Leu Glu Leu Leu Ala Phe Ile Ala Ala
225                 230                 235                 240

Ala Leu Gln Gln Glu Glu Ser Arg His His His His His His
                245                 250

<210> SEQ ID NO 15
<211> LENGTH: 257
<212> TYPE: PRT
<213> ORGANISM: Artificial
<220> FEATURE:
<223> OTHER INFORMATION: Synthetic peptide

<400> SEQUENCE: 15

Met Asn Ser Leu Ile Lys Glu Asn Met His Met Lys Leu Tyr Met Glu
 1               5                  10                  15

Gly Thr Val Asn Asn His His Phe Lys Cys Thr Ser Glu Gly Glu Gly
                20                  25                  30

Lys Pro Tyr Glu Gly Thr Gln Thr Met Arg Ile Lys Val Val Glu Gly
             35                  40                  45

Gly Pro Leu Pro Phe Ala Phe Asp Ile Leu Ala Thr Ser Phe Met Tyr
 50                  55                  60

Gly Ser Arg Thr Phe Ile Lys Tyr Pro Lys Gly Ile Pro Asp Phe Phe
 65                  70                  75                  80

Lys Gln Ser Phe Pro Glu Gly Phe Thr Trp Glu Arg Val Thr Arg Tyr
                 85                  90                  95

Glu Asp Gly Gly Val Val Thr Ala Gln Asp Thr Ser Leu Glu Asp
                100                 105                 110

Gly Cys Leu Val Tyr His Val Gln Val Arg Gly Val Asn Phe Pro Ser
            115                 120                 125

Asn Gly Pro Val Met Gln Lys Lys Thr Leu Gly Trp Glu Pro Asn Thr
130                 135                 140

Glu Met Leu Tyr Pro Ala Asp Gly Gly Leu Glu Gly Arg Ser Asp Met
145                 150                 155                 160

```
Ala Leu Lys Val Gly Gly His Leu Ser Cys Ser Phe Val Thr Thr
            165                 170                 175

Tyr Arg Ser Lys Lys Thr Val Gly Asn Ile Lys Met Pro Gly Ile His
        180                 185                 190

Ala Val Asp His Arg Leu Val Arg Ile Lys Glu Ala Asp Lys Glu Thr
        195                 200                 205

Tyr Val Glu Gln His Glu Val Ala Val Ala Lys Phe Ala Gly Leu Gly
    210                 215                 220

Gly Gly Met Asp Glu Leu Tyr Lys Ser Gln Gly Ile Ser Glu Lys Gln
225                 230                 235                 240

Leu Asp Gln Leu Leu Ser Gln Leu Ile Ser Arg His His His His
                245                 250                 255

His
```

<210> SEQ ID NO 16
<211> LENGTH: 251
<212> TYPE: PRT
<213> ORGANISM: Artificial
<220> FEATURE:
<223> OTHER INFORMATION: Synthetic peptide

<400> SEQUENCE: 16

```
Met Ser Leu Ser Lys Gln Val Leu Pro Arg Asp Val Arg Met Arg Phe
1               5                   10                  15

His Met Asp Gly Cys Val Asn Gly His Gln Phe Thr Ile Glu Gly Glu
            20                  25                  30

Gly Ala Gly Lys Pro Tyr Glu Gly Lys Lys Thr Leu Lys Leu Arg Val
        35                  40                  45

Thr Lys Gly Gly Pro Leu Pro Phe Ala Phe Asp Ile Leu Ser Ala Thr
    50                  55                  60

Phe Thr Tyr Gly Asn Arg Cys Phe Cys Asp Tyr Pro Glu Asp Met Pro
65                  70                  75                  80

Asp Tyr Phe Lys Gln Ser Leu Pro Glu Gly Tyr Ser Trp Glu Arg Thr
                85                  90                  95

Leu Met Phe Glu Asp Gly Gly Cys Gly Thr Ala Ser Ala His Ile Ser
            100                 105                 110

Leu Glu Lys Asp Cys Phe Ile His Asn Ser Thr Phe His Gly Val Asn
        115                 120                 125

Phe Pro Ala Asn Gly Pro Val Met Gln Lys Lys Thr Leu Asn Trp Glu
    130                 135                 140

Pro Ser Ser Glu Leu Ile Thr Ala Cys Asp Gly Ile Leu Lys Gly Asp
145                 150                 155                 160

Val Thr Met Phe Leu Leu Leu Glu Gly Gly His Arg Leu Lys Cys Gln
                165                 170                 175

Phe Thr Thr Ser Tyr Lys Ala His Lys Ala Val Lys Met Pro Pro Asn
            180                 185                 190

His Ile Ile Glu His Val Leu Val Lys Lys Glu Val Ala Asp Gly Phe
        195                 200                 205

Gln Ile Gln Glu His Ala Val Ala Lys His Phe Thr Val Asp Val Lys
    210                 215                 220

Glu Thr Ser Gln Gly Ile Ser Glu Lys Gln Leu Asp Gln Leu Leu Ser
225                 230                 235                 240

Gln Leu Ile Ser Arg His His His His His His
                245                 250
```

-continued

```
<210> SEQ ID NO 17
<211> LENGTH: 256
<212> TYPE: PRT
<213> ORGANISM: Artificial
<220> FEATURE:
<223> OTHER INFORMATION: Synthetic peptide

<400> SEQUENCE: 17

Met Asn Ser Leu Ile Lys Glu Asn Met His Met Lys Leu Tyr Met Glu
1               5                   10                  15

Gly Thr Val Asn Asn His His Phe Lys Cys Thr Ser Glu Gly Glu Gly
                20                  25                  30

Lys Pro Tyr Glu Gly Thr Gln Thr Met Arg Ile Lys Val Val Glu Gly
            35                  40                  45

Gly Pro Leu Pro Phe Ala Phe Asp Ile Leu Ala Thr Ser Phe Met Tyr
        50                  55                  60

Gly Ser Arg Thr Phe Ile Lys Tyr Pro Lys Gly Ile Pro Asp Phe Phe
65                  70                  75                  80

Lys Gln Ser Phe Pro Glu Gly Phe Thr Trp Glu Arg Val Thr Arg Tyr
                85                  90                  95

Glu Asp Gly Gly Val Val Thr Ala Thr Gln Asp Thr Ser Leu Glu Asp
            100                 105                 110

Gly Cys Leu Val Tyr His Val Gln Val Arg Gly Val Asn Phe Pro Ser
        115                 120                 125

Asn Gly Pro Val Met Gln Lys Lys Thr Leu Gly Trp Glu Pro Asn Thr
130                 135                 140

Glu Met Leu Tyr Pro Ala Asp Gly Gly Leu Glu Gly Arg Ser Asp Met
145                 150                 155                 160

Ala Leu Lys Leu Val Gly Gly His Leu Ser Cys Ser Phe Val Thr
                165                 170                 175

Thr Tyr Arg Ser Lys Lys Thr Val Gly Asn Ile Lys Met Pro Gly Ile
            180                 185                 190

His Ala Val Asp His Arg Leu Val Arg Ile Lys Glu Ala Asp Lys Glu
        195                 200                 205

Thr Tyr Val Glu Gln His Glu Val Ala Val Ala Lys Phe Ala Gly Leu
    210                 215                 220

Gly Gly Gly Met Asp Glu Leu Tyr Lys Leu Glu Glu Leu Leu Glu Glu
225                 230                 235                 240

Leu Ile Glu Glu Leu Leu Glu Glu Ser Arg His His His His His His
                245                 250                 255

<210> SEQ ID NO 18
<211> LENGTH: 249
<212> TYPE: PRT
<213> ORGANISM: Artificial
<220> FEATURE:
<223> OTHER INFORMATION: Synthetic peptide

<400> SEQUENCE: 18

Met Ser Leu Ser Lys Gln Val Leu Pro Arg Asp Val Arg Met Arg Phe
1               5                   10                  15

His Met Asp Gly Cys Val Asn Gly His Gln Phe Thr Ile Glu Gly Glu
                20                  25                  30

Gly Ala Gly Lys Pro Tyr Glu Gly Lys Lys Thr Leu Lys Leu Arg Val
            35                  40                  45

Thr Lys Gly Gly Pro Leu Pro Phe Ala Phe Asp Ile Leu Ser Ala Thr
        50                  55                  60
```

Phe Thr Tyr Gly Asn Arg Cys Phe Cys Asp Tyr Pro Glu Asp Met Pro
65                  70                  75                  80

Asp Tyr Phe Lys Gln Ser Leu Pro Glu Gly Tyr Ser Trp Glu Arg Thr
            85                  90                  95

Leu Met Phe Glu Asp Gly Gly Cys Gly Thr Ala Ser Ala His Ile Ser
            100                 105                 110

Leu Glu Lys Asp Cys Phe Ile His Asn Ser Thr Phe His Gly Val Asn
        115                 120                 125

Phe Pro Ala Asn Gly Pro Val Met Gln Lys Lys Thr Leu Asn Trp Glu
    130                 135                 140

Pro Ser Ser Glu Leu Ile Thr Ala Cys Asp Gly Ile Leu Lys Gly Asp
145                 150                 155                 160

Val Thr Met Phe Leu Leu Leu Glu Gly Gly His Arg Leu Lys Cys Gln
            165                 170                 175

Phe Thr Thr Ser Tyr Lys Ala His Lys Ala Val Lys Met Pro Pro Asn
            180                 185                 190

His Ile Ile Glu His Val Leu Val Lys Lys Glu Val Ala Asp Gly Phe
        195                 200                 205

Gln Ile Gln Glu His Ala Val Ala Lys His Phe Thr Val Asp Val Lys
    210                 215                 220

Glu Thr Leu Glu Glu Leu Leu Glu Glu Leu Ile Glu Glu Leu Leu Glu
225                 230                 235                 240

Glu Ser Arg His His His His His His
            245

<210> SEQ ID NO 19
<211> LENGTH: 23
<212> TYPE: PRT
<213> ORGANISM: Artificial
<220> FEATURE:
<223> OTHER INFORMATION: P4 consensus
<220> FEATURE:
<221> NAME/KEY: MISC_FEATURE
<222> LOCATION: (1)..(1)
<223> OTHER INFORMATION: Xaa at position 1 is S
<220> FEATURE:
<221> NAME/KEY: MISC_FEATURE
<222> LOCATION: (2)..(2)
<223> OTHER INFORMATION: Xaa at position 2 is Q, E, gamma-glutamate
      ("g-glutamate"), G, A, or S
<220> FEATURE:
<221> NAME/KEY: MISC_FEATURE
<222> LOCATION: (3)..(3)
<223> OTHER INFORMATION: Xaa at position 3 is G
<220> FEATURE:
<221> NAME/KEY: MISC_FEATURE
<222> LOCATION: (4)..(4)
<223> OTHER INFORMATION: Xaa at position 4 is I
<220> FEATURE:
<221> NAME/KEY: MISC_FEATURE
<222> LOCATION: (5)..(5)
<223> OTHER INFORMATION: Xaa at position 5 is S
<220> FEATURE:
<221> NAME/KEY: MISC_FEATURE
<222> LOCATION: (6)..(6)
<223> OTHER INFORMATION: Xaa at position 6 is E
<220> FEATURE:
<221> NAME/KEY: MISC_FEATURE
<222> LOCATION: (7)..(7)
<223> OTHER INFORMATION: Xaa at position 7 is K
<220> FEATURE:
<221> NAME/KEY: MISC_FEATURE
<222> LOCATION: (8)..(8)
<223> OTHER INFORMATION: Xaa at position 8 is Q, E, g-glutamate, G, A,
      or S
<220> FEATURE:
<221> NAME/KEY: MISC_FEATURE

```
<222> LOCATION: (9)..(9)
<223> OTHER INFORMATION: Xaa at position 9 is L, A, D, isoaspartic acid
      ("isoD"), I, V, or F
<220> FEATURE:
<221> NAME/KEY: MISC_FEATURE
<222> LOCATION: (10)..(10)
<223> OTHER INFORMATION: Xaa at position 10 is D
<220> FEATURE:
<221> NAME/KEY: MISC_FEATURE
<222> LOCATION: (11)..(11)
<223> OTHER INFORMATION: Xaa at position 11 is Q, E, g-glutamate, G, A,
      or S
<220> FEATURE:
<221> NAME/KEY: MISC_FEATURE
<222> LOCATION: (12)..(12)
<223> OTHER INFORMATION: Xaa at position 12 is L, D, isoD, I, or F
<220> FEATURE:
<221> NAME/KEY: MISC_FEATURE
<222> LOCATION: (13)..(13)
<223> OTHER INFORMATION: Xaa at position 13 is L, I, V, or F
<220> FEATURE:
<221> NAME/KEY: MISC_FEATURE
<222> LOCATION: (14)..(14)
<223> OTHER INFORMATION: Xaa at position 14 is any hydrophilic amino
      acid, preferably C, S, or T, S or T, or only S
<220> FEATURE:
<221> NAME/KEY: MISC_FEATURE
<222> LOCATION: (15)..(15)
<223> OTHER INFORMATION: Xaa at position 15 is Q, E, g-glutamate, G, A,
      S, K, or I
<220> FEATURE:
<221> NAME/KEY: MISC_FEATURE
<222> LOCATION: (16)..(16)
<223> OTHER INFORMATION: Xaa at position 16 is L, A, I, V, M, or F
<220> FEATURE:
<221> NAME/KEY: MISC_FEATURE
<222> LOCATION: (17)..(17)
<223> OTHER INFORMATION: Xaa at position 17 is I, S, or F
<220> FEATURE:
<221> NAME/KEY: MISC_FEATURE
<222> LOCATION: (18)..(18)
<223> OTHER INFORMATION: Xaa at position 18 is Q, E, g-glutamate, G, A,
      or S
<220> FEATURE:
<221> NAME/KEY: MISC_FEATURE
<222> LOCATION: (19)..(19)
<223> OTHER INFORMATION: Xaa at position 19 is A
<220> FEATURE:
<221> NAME/KEY: MISC_FEATURE
<222> LOCATION: (20)..(20)
<223> OTHER INFORMATION: Xaa at position 20 is L, I, V, or F
<220> FEATURE:
<221> NAME/KEY: MISC_FEATURE
<222> LOCATION: (21)..(21)
<223> OTHER INFORMATION: Xaa at position 21 is L or F
<220> FEATURE:
<221> NAME/KEY: MISC_FEATURE
<222> LOCATION: (22)..(22)
<223> OTHER INFORMATION: Xaa at position 22 is Q, E, g-glutamate, G, A,
      or S
<220> FEATURE:
<221> NAME/KEY: MISC_FEATURE
<222> LOCATION: (23)..(23)
<223> OTHER INFORMATION: Xaa at position 23 is P

<400> SEQUENCE: 19

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 20
<211> LENGTH: 23
<212> TYPE: PRT
<213> ORGANISM: Artificial
<220> FEATURE:
```

```
<223> OTHER INFORMATION: P1 consensus
<220> FEATURE:
<221> NAME/KEY: MISC_FEATURE
<222> LOCATION: (1)..(1)
<223> OTHER INFORMATION: Xaa at position 1 is N, D, isoD, G, A, or S
<220> FEATURE:
<221> NAME/KEY: MISC_FEATURE
<222> LOCATION: (2)..(2)
<223> OTHER INFORMATION: Xaa at position 2 is Q, E, g-glutamate, G, A,
      or S
<220> FEATURE:
<221> NAME/KEY: MISC_FEATURE
<222> LOCATION: (3)..(3)
<223> OTHER INFORMATION: Xaa at position 3 is G
<220> FEATURE:
<221> NAME/KEY: MISC_FEATURE
<222> LOCATION: (4)..(4)
<223> OTHER INFORMATION: Xaa at position 4 is I
<220> FEATURE:
<221> NAME/KEY: MISC_FEATURE
<222> LOCATION: (5)..(5)
<223> OTHER INFORMATION: Xaa at position 5 is S
<220> FEATURE:
<221> NAME/KEY: MISC_FEATURE
<222> LOCATION: (6)..(6)
<223> OTHER INFORMATION: Xaa at position 6 is E
<220> FEATURE:
<221> NAME/KEY: MISC_FEATURE
<222> LOCATION: (7)..(7)
<223> OTHER INFORMATION: Xaa at position 7 is K
<220> FEATURE:
<221> NAME/KEY: MISC_FEATURE
<222> LOCATION: (8)..(8)
<223> OTHER INFORMATION: Xaa at position 8 is Q, E, g-glutamate, G, A,
      or S
<220> FEATURE:
<221> NAME/KEY: MISC_FEATURE
<222> LOCATION: (9)..(9)
<223> OTHER INFORMATION: Xaa at position 9 is L
<220> FEATURE:
<221> NAME/KEY: MISC_FEATURE
<222> LOCATION: (10)..(10)
<223> OTHER INFORMATION: Xaa at position 10 is D
<220> FEATURE:
<221> NAME/KEY: MISC_FEATURE
<222> LOCATION: (11)..(11)
<223> OTHER INFORMATION: Xaa at position 11 is Q, E, g-glutamate, G, A,
      or S
<220> FEATURE:
<221> NAME/KEY: MISC_FEATURE
<222> LOCATION: (12)..(12)
<223> OTHER INFORMATION: Xaa at position 12 is L
<220> FEATURE:
<221> NAME/KEY: MISC_FEATURE
<222> LOCATION: (13)..(13)
<223> OTHER INFORMATION: Xaa at position 13 is L
<220> FEATURE:
<221> NAME/KEY: MISC_FEATURE
<222> LOCATION: (14)..(14)
<223> OTHER INFORMATION: Xaa at position 14 is T
<220> FEATURE:
<221> NAME/KEY: MISC_FEATURE
<222> LOCATION: (15)..(15)
<223> OTHER INFORMATION: Xaa at position 15 is Q, E, g-glutamate, G, A,
      or S
<220> FEATURE:
<221> NAME/KEY: MISC_FEATURE
<222> LOCATION: (16)..(16)
<223> OTHER INFORMATION: Xaa at position 16 is L
<220> FEATURE:
<221> NAME/KEY: MISC_FEATURE
<222> LOCATION: (17)..(17)
<223> OTHER INFORMATION: Xaa at position 17 is I
<220> FEATURE:
<221> NAME/KEY: MISC_FEATURE
<222> LOCATION: (18)..(18)
<223> OTHER INFORMATION: Xaa at position 18 is M, T, K, E, g-glutamate,
      G, A, or S
<220> FEATURE:
```

```
<221> NAME/KEY: MISC_FEATURE
<222> LOCATION: (19)..(19)
<223> OTHER INFORMATION: Xaa at position 19 is A
<220> FEATURE:
<221> NAME/KEY: MISC_FEATURE
<222> LOCATION: (20)..(20)
<223> OTHER INFORMATION: Xaa at position 20 is L
<220> FEATURE:
<221> NAME/KEY: MISC_FEATURE
<222> LOCATION: (21)..(21)
<223> OTHER INFORMATION: Xaa at position 21 is L
<220> FEATURE:
<221> NAME/KEY: MISC_FEATURE
<222> LOCATION: (22)..(22)
<223> OTHER INFORMATION: Xaa at position 22 is Q, E, g-glutamate, G, A,
      or S
<220> FEATURE:
<221> NAME/KEY: MISC_FEATURE
<222> LOCATION: (23)..(23)
<223> OTHER INFORMATION: Xaa at position 23 is Q, E, g-glutamate, G, A,
      or S

<400> SEQUENCE: 20

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa
            20

<210> SEQ ID NO 21
<211> LENGTH: 13
<212> TYPE: PRT
<213> ORGANISM: Artificial
<220> FEATURE:
<223> OTHER INFORMATION: P17/18 min consensus peptide
<220> FEATURE:
<221> NAME/KEY: MISC_FEATURE
<222> LOCATION: (1)..(1)
<223> OTHER INFORMATION: Xaa at position 1 is L or M
<220> FEATURE:
<221> NAME/KEY: MISC_FEATURE
<222> LOCATION: (2)..(2)
<223> OTHER INFORMATION: Xaa at position 2 is A, S, T, G, D, isoD, E,
      g-glutamate, Q, N, K, or R
<220> FEATURE:
<221> NAME/KEY: MISC_FEATURE
<222> LOCATION: (3)..(3)
<223> OTHER INFORMATION: Xaa at position 3 is Q, A, S, T, G, D, isoD, E,
      g-glutamate, N, K, or R
<220> FEATURE:
<221> NAME/KEY: MISC_FEATURE
<222> LOCATION: (4)..(4)
<223> OTHER INFORMATION: Xaa at position 4 is L
<220> FEATURE:
<221> NAME/KEY: MISC_FEATURE
<222> LOCATION: (5)..(5)
<223> OTHER INFORMATION: Xaa at position 5 is L
<220> FEATURE:
<221> NAME/KEY: MISC_FEATURE
<222> LOCATION: (6)..(6)
<223> OTHER INFORMATION: Xaa at position 6 is A, S, T, G, D, isoD, E,
      g-glutamate, Q, N, K, or R
<220> FEATURE:
<221> NAME/KEY: MISC_FEATURE
<222> LOCATION: (7)..(7)
<223> OTHER INFORMATION: Xaa at position 7 is Q, A, S, T, G, D, isoD, E,
      g-glutamate, N, K, or R
<220> FEATURE:
<221> NAME/KEY: MISC_FEATURE
<222> LOCATION: (8)..(8)
<223> OTHER INFORMATION: Xaa at position 8 is L
<220> FEATURE:
<221> NAME/KEY: MISC_FEATURE
<222> LOCATION: (9)..(9)
<223> OTHER INFORMATION: Xaa at position 9 is L
<220> FEATURE:
<221> NAME/KEY: MISC_FEATURE
```

```
<222> LOCATION: (10)..(10)
<223> OTHER INFORMATION: Xaa at position 10 is K, A, S, T, G, D, isoD,
      E, g-glutamate, Q, N, or R
<220> FEATURE:
<221> NAME/KEY: MISC_FEATURE
<222> LOCATION: (11)..(11)
<223> OTHER INFORMATION: Xaa at position 11 is S, A,T, G, D, isoD, E,
      g-glutamate, Q, N, K, or R
<220> FEATURE:
<221> NAME/KEY: MISC_FEATURE
<222> LOCATION: (12)..(12)
<223> OTHER INFORMATION: Xaa at position 12 is L
<220> FEATURE:
<221> NAME/KEY: MISC_FEATURE
<222> LOCATION: (13)..(13)
<223> OTHER INFORMATION: Xaa at position 13 is L

<400> SEQUENCE: 21

Xaa Xaa Xaa Xaa Xaa Xaa Xaa Xaa Xaa Xaa Xaa Xaa Xaa
1               5                   10

<210> SEQ ID NO 22
<211> LENGTH: 13
<212> TYPE: PRT
<213> ORGANISM: Artificial
<220> FEATURE:
<223> OTHER INFORMATION: P19 consensus peptide
<220> FEATURE:
<221> NAME/KEY: MISC_FEATURE
<222> LOCATION: (1)..(1)
<223> OTHER INFORMATION: Xaa at position 1 is optional and can be L, I,
      V, F, or M
<220> FEATURE:
<221> NAME/KEY: MISC_FEATURE
<222> LOCATION: (2)..(2)
<223> OTHER INFORMATION: Xaa at position 2 is L
<220> FEATURE:
<221> NAME/KEY: MISC_FEATURE
<222> LOCATION: (3)..(3)
<223> OTHER INFORMATION: Xaa at position 3 is K, A, S, T, G, D, isoD, E,
      g-glutamate, Q, N, or R
<220> FEATURE:
<221> NAME/KEY: MISC_FEATURE
<222> LOCATION: (4)..(4)
<223> OTHER INFORMATION: Xaa at position 4 is A, S, T, G, D, isoD, E,
      g-glutamate, Q, N, K, or R
<220> FEATURE:
<221> NAME/KEY: MISC_FEATURE
<222> LOCATION: (5)..(5)
<223> OTHER INFORMATION: Xaa at position 5 is L or M
<220> FEATURE:
<221> NAME/KEY: MISC_FEATURE
<222> LOCATION: (6)..(6)
<223> OTHER INFORMATION: Xaa at position 6 is L
<220> FEATURE:
<221> NAME/KEY: MISC_FEATURE
<222> LOCATION: (7)..(7)
<223> OTHER INFORMATION: Xaa at position 7 is K, A, S, T, G, D, isoD, E,
      g-glutamate, Q, N, or R
<220> FEATURE:
<221> NAME/KEY: MISC_FEATURE
<222> LOCATION: (8)..(8)
<223> OTHER INFORMATION: Xaa at position 8 is L
<220> FEATURE:
<221> NAME/KEY: MISC_FEATURE
<222> LOCATION: (9)..(9)
<223> OTHER INFORMATION: Xaa at position 9 is I
<220> FEATURE:
<221> NAME/KEY: MISC_FEATURE
<222> LOCATION: (10)..(10)
<223> OTHER INFORMATION: Xaa at position 10 is A, S, T, G, D, isoD, E,
      g-glutamate, Q, N, K, or R
<220> FEATURE:
<221> NAME/KEY: MISC_FEATURE
<222> LOCATION: (11)..(11)
<223> OTHER INFORMATION: Xaa at position 11 is R, A, S, T, G, D, isoD,
      E, g-glutamate, Q, N, or K
```

```
<220> FEATURE:
<221> NAME/KEY: MISC_FEATURE
<222> LOCATION: (12)..(12)
<223> OTHER INFORMATION: Xaa at position 12 is L, I, V, F, or M
<220> FEATURE:
<221> NAME/KEY: MISC_FEATURE
<222> LOCATION: (13)..(13)
<223> OTHER INFORMATION: Xaa at position 13 is L, I, V, F, or M

<400> SEQUENCE: 22

Xaa Xaa Xaa Xaa Xaa Xaa Xaa Xaa Xaa Xaa Xaa Xaa Xaa
1               5                   10

<210> SEQ ID NO 23
<211> LENGTH: 23
<212> TYPE: PRT
<213> ORGANISM: Artificial
<220> FEATURE:
<223> OTHER INFORMATION: P1-18t peptide

<400> SEQUENCE: 23

Asn Gln Gly Ile Ser Glu Lys Gln Leu Asp Gln Leu Leu Thr Gln Leu
1               5                   10                  15

Ile Thr Ala Leu Leu Gln Gln
            20

<210> SEQ ID NO 24
<211> LENGTH: 23
<212> TYPE: PRT
<213> ORGANISM: Artificial
<220> FEATURE:
<223> OTHER INFORMATION: P4-14s peptide

<400> SEQUENCE: 24

Ser Gln Gly Ile Ser Glu Lys Gln Leu Asp Gln Leu Leu Ser Gln Leu
1               5                   10                  15

Ile Gln Ala Leu Leu Gln Pro
            20

<210> SEQ ID NO 25
<211> LENGTH: 27
<212> TYPE: PRT
<213> ORGANISM: Artificial
<220> FEATURE:
<223> OTHER INFORMATION: P18 peptide

<400> SEQUENCE: 25

Gln Gln Pro Ile Asp Arg Gln Thr Ile Glu Gln Met Ala Gln Leu Leu
1               5                   10                  15

Ala Gln Leu Leu Lys Ser Leu Leu Ser Pro Gln
            20                  25

<210> SEQ ID NO 26
<211> LENGTH: 25
<212> TYPE: PRT
<213> ORGANISM: Artificial
<220> FEATURE:
<223> OTHER INFORMATION: P19 peptide

<400> SEQUENCE: 26

Ile Thr Pro Asp Gly Gln Gly Gly Gln Ile Gly Asp Asn Pro Leu
1               5                   10                  15

Leu Lys Ala Met Leu Lys Leu Ile Ala
            20                  25
```

-continued

```
<210> SEQ ID NO 27
<211> LENGTH: 15
<212> TYPE: PRT
<213> ORGANISM: Artificial
<220> FEATURE:
<223> OTHER INFORMATION: P30-3 peptide

<400> SEQUENCE: 27

Leu Glu Glu Leu Leu Glu Glu Leu Ile Glu Glu Leu Leu Glu Glu
1               5                   10                  15

<210> SEQ ID NO 28
<211> LENGTH: 13
<212> TYPE: PRT
<213> ORGANISM: Artificial
<220> FEATURE:
<223> OTHER INFORMATION: P30-4 peptide

<400> SEQUENCE: 28

Leu Glu Glu Leu Leu Glu Glu Leu Ile Glu Glu Leu Leu
1               5                   10

<210> SEQ ID NO 29
<211> LENGTH: 9
<212> TYPE: PRT
<213> ORGANISM: Artificial
<220> FEATURE:
<223> OTHER INFORMATION: Peptide
<220> FEATURE:
<221> NAME/KEY: MISC_FEATURE
<222> LOCATION: (1)..(1)
<223> OTHER INFORMATION: Xaa at position 1 is L
<220> FEATURE:
<221> NAME/KEY: MISC_FEATURE
<222> LOCATION: (2)..(2)
<223> OTHER INFORMATION: Xaa at position 2 is G, A, S, T, D, isoD, E,
      g-glutamate, Q, N, K, or R
<220> FEATURE:
<221> NAME/KEY: MISC_FEATURE
<222> LOCATION: (3)..(3)
<223> OTHER INFORMATION: Xaa at position 3 is G, A, S, T, D, isoD, E,
      g-glutamate, Q, N, K, or R
<220> FEATURE:
<221> NAME/KEY: MISC_FEATURE
<222> LOCATION: (4)..(4)
<223> OTHER INFORMATION: Xaa at position 4 is L or I
<220> FEATURE:
<221> NAME/KEY: MISC_FEATURE
<222> LOCATION: (5)..(5)
<223> OTHER INFORMATION: Xaa at position 5 is L or I
<220> FEATURE:
<221> NAME/KEY: MISC_FEATURE
<222> LOCATION: (6)..(6)
<223> OTHER INFORMATION: Xaa at position 6 is G, A, S, T, D, isoD, E,
      g-glutamate, Q, N, K, or R
<220> FEATURE:
<221> NAME/KEY: MISC_FEATURE
<222> LOCATION: (7)..(7)
<223> OTHER INFORMATION: Xaa at position 7 is G, A, S, T, D, isoD, E,
      g-glutamate, Q, N, K, or R
<220> FEATURE:
<221> NAME/KEY: MISC_FEATURE
<222> LOCATION: (8)..(8)
<223> OTHER INFORMATION: Xaa at position 8 is L, I, or V
<220> FEATURE:
<221> NAME/KEY: MISC_FEATURE
<222> LOCATION: (9)..(9)
<223> OTHER INFORMATION: Xaa at position 9 is L, I, or V

<400> SEQUENCE: 29

Xaa Xaa Xaa Xaa Xaa Xaa Xaa Xaa Xaa
1               5
```

```
<210> SEQ ID NO 30
<211> LENGTH: 17
<212> TYPE: PRT
<213> ORGANISM: Artificial
<220> FEATURE:
<223> OTHER INFORMATION: P1-29

<400> SEQUENCE: 30

Asn Gln Gly Ile Ser Glu Lys Gln Leu Asp Gln Leu Leu Thr Gln Leu
1               5                   10                  15

Ile

<210> SEQ ID NO 31
<211> LENGTH: 17
<212> TYPE: PRT
<213> ORGANISM: Artificial
<220> FEATURE:
<223> OTHER INFORMATION: P4-111

<400> SEQUENCE: 31

Ser Gln Gly Ile Ser Glu Lys Gln Leu Asp Gln Leu Leu Ser Gln Leu
1               5                   10                  15

Ile

<210> SEQ ID NO 32
<211> LENGTH: 33
<212> TYPE: PRT
<213> ORGANISM: Artificial
<220> FEATURE:
<223> OTHER INFORMATION: P14

<400> SEQUENCE: 32

Gln Ala Gly Pro Gln Ser Ala Asn Lys Thr Gly Asn Val Asp Asp Ala
1               5                   10                  15

Asn Asn Gln Asp Pro Met Gln Ala Leu Met Gln Leu Leu Glu Asp Leu
                20                  25                  30

Val

<210> SEQ ID NO 33
<211> LENGTH: 18
<212> TYPE: PRT
<213> ORGANISM: Artificial
<220> FEATURE:
<223> OTHER INFORMATION: P14a

<400> SEQUENCE: 33

Ala Asn Asn Gln Asp Pro Met Gln Ala Leu Met Gln Leu Leu Glu Asp
1               5                   10                  15

Leu Val

<210> SEQ ID NO 34
<211> LENGTH: 13
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa at position 1 is L
<220> FEATURE:
<221> NAME/KEY: MISC_FEATURE
<222> LOCATION: (2)..(2)
<223> OTHER INFORMATION: Xaa at position 2 is M, A, D, isoD, E,
      g-glutamate, Q, N, S, or G
<220> FEATURE:
```

```
<221> NAME/KEY: MISC_FEATURE
<222> LOCATION: (3)..(3)
<223> OTHER INFORMATION: Xaa at position 3 is optional and, when
      present, is selected from D, isoD, E, g-glutamate, Q, N, S, or G
<220> FEATURE:
<221> NAME/KEY: MISC_FEATURE
<222> LOCATION: (4)..(4)
<223> OTHER INFORMATION: Xaa at position 4 is L
<220> FEATURE:
<221> NAME/KEY: MISC_FEATURE
<222> LOCATION: (5)..(5)
<223> OTHER INFORMATION: Xaa at position 5 is L
<220> FEATURE:
<221> NAME/KEY: MISC_FEATURE
<222> LOCATION: (6)..(6)
<223> OTHER INFORMATION: Xaa at position 6 is L
<220> FEATURE:
<221> NAME/KEY: MISC_FEATURE
<222> LOCATION: (7)..(7)
<223> OTHER INFORMATION: Xaa at position 7 is M, A, D, isoD, E,
      g-glutamate, Q, N, S, or G
<220> FEATURE:
<221> NAME/KEY: MISC_FEATURE
<222> LOCATION: (8)..(8)
<223> OTHER INFORMATION: Xaa at position 8 is F or L
<220> FEATURE:
<221> NAME/KEY: MISC_FEATURE
<222> LOCATION: (9)..(9)
<223> OTHER INFORMATION: Xaa at position 9 is I or L
<220> FEATURE:
<221> NAME/KEY: MISC_FEATURE
<222> LOCATION: (10)..(10)
<223> OTHER INFORMATION: Xaa at position 10 is M, A, D, isoD, E,
      g-glutamate, Q, N, S, or G
<220> FEATURE:
<221> NAME/KEY: MISC_FEATURE
<222> LOCATION: (11)..(11)
<223> OTHER INFORMATION: Xaa at position 11 is M, A, D, isoD, E,
      g-glutamate, Q, N, S, or G
<220> FEATURE:
<221> NAME/KEY: MISC_FEATURE
<222> LOCATION: (12)..(12)
<223> OTHER INFORMATION: Xaa at position 12 is M, A, D, isoD, E,
      g-glutamate, Q, N, S, or G
<220> FEATURE:
<221> NAME/KEY: MISC_FEATURE
<222> LOCATION: (13)..(13)
<223> OTHER INFORMATION: Xaa at position 13 is L

<400> SEQUENCE: 34

Xaa Xaa Xaa Xaa Xaa Xaa Xaa Xaa Xaa Xaa Xaa Xaa Xaa
1               5                   10

<210> SEQ ID NO 35
<211> LENGTH: 17
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa at position 1 is Q or E
<220> FEATURE:
<221> NAME/KEY: MISC_FEATURE
<222> LOCATION: (2)..(2)
<223> OTHER INFORMATION: Xaa at position 2 is Q or E
<220> FEATURE:
<221> NAME/KEY: MISC_FEATURE
<222> LOCATION: (3)..(3)
<223> OTHER INFORMATION: Xaa at position 3 is L, I, V, or F
<220> FEATURE:
<221> NAME/KEY: MISC_FEATURE
<222> LOCATION: (4)..(4)
<223> OTHER INFORMATION: Xaa at position 4 is M, A, D, isoD, E,
      g-glutamate, Q, N, S, or G
<220> FEATURE:
```

-continued

```
<221> NAME/KEY: MISC_FEATURE
<222> LOCATION: (5)..(5)
<223> OTHER INFORMATION: Xaa at position 5 is optional and, when
      present, is selected from D, isoD, E, g-glutamate, Q, N, S, and G
<220> FEATURE:
<221> NAME/KEY: MISC_FEATURE
<222> LOCATION: (6)..(6)
<223> OTHER INFORMATION: Xaa at position 6 is L, I, V, or F
<220> FEATURE:
<221> NAME/KEY: MISC_FEATURE
<222> LOCATION: (7)..(7)
<223> OTHER INFORMATION: Xaa at position 7 is L, I, V, or F
<220> FEATURE:
<221> NAME/KEY: MISC_FEATURE
<222> LOCATION: (8)..(8)
<223> OTHER INFORMATION: Xaa at position 8 is L, I, V, or F
<220> FEATURE:
<221> NAME/KEY: MISC_FEATURE
<222> LOCATION: (9)..(9)
<223> OTHER INFORMATION: Xaa at position 9 is M, A, D, isoD, E,
      g-glutamate, Q, N, S, or G
<220> FEATURE:
<221> NAME/KEY: MISC_FEATURE
<222> LOCATION: (10)..(10)
<223> OTHER INFORMATION: Xaa at position 10 is L, I, V, or F
<220> FEATURE:
<221> NAME/KEY: MISC_FEATURE
<222> LOCATION: (11)..(11)
<223> OTHER INFORMATION: Xaa at position 11 is L, I, V, or F
<220> FEATURE:
<221> NAME/KEY: MISC_FEATURE
<222> LOCATION: (12)..(12)
<223> OTHER INFORMATION: Xaa at position 12 is M, A, D, isoD, E,
      g-glutamate, Q, N, S, or G
<220> FEATURE:
<221> NAME/KEY: MISC_FEATURE
<222> LOCATION: (13)..(13)
<223> OTHER INFORMATION: Xaa at position 13 is M, A, D, isoD, E,
      g-glutamate, Q, N, S, or G
<220> FEATURE:
<221> NAME/KEY: MISC_FEATURE
<222> LOCATION: (14)..(14)
<223> OTHER INFORMATION: Xaa at position 14 is M, A, D, isoD, E,
      g-glutamate, Q, N, S, or G
<220> FEATURE:
<221> NAME/KEY: MISC_FEATURE
<222> LOCATION: (15)..(15)
<223> OTHER INFORMATION: Xaa at position 15 is L, I, V, or F
<220> FEATURE:
<221> NAME/KEY: MISC_FEATURE
<222> LOCATION: (16)..(16)
<223> OTHER INFORMATION: Xaa at position 16 is D, G, Q, or E
<220> FEATURE:
<221> NAME/KEY: MISC_FEATURE
<222> LOCATION: (17)..(17)
<223> OTHER INFORMATION: Xaa at position 17 is D, G, Q, or E

<400> SEQUENCE: 35

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 36
<211> LENGTH: 15
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa at position 1 is L, I, V, or F
<220> FEATURE:
<221> NAME/KEY: MISC_FEATURE
<222> LOCATION: (2)..(2)
<223> OTHER INFORMATION: Xaa at position 2 is M, A, D, isoD, E,
```

```
            g-glutamate, Q, N, S, and G
<220> FEATURE:
<221> NAME/KEY: MISC_FEATURE
<222> LOCATION: (3)..(3)
<223> OTHER INFORMATION: Xaa at position 3 is optional and, when
      present, is selected from D, isoD, E, g-glutamate, Q, N, S, and G
<220> FEATURE:
<221> NAME/KEY: MISC_FEATURE
<222> LOCATION: (4)..(4)
<223> OTHER INFORMATION: Xaa at position 4 is L, I, V, or F
<220> FEATURE:
<221> NAME/KEY: MISC_FEATURE
<222> LOCATION: (5)..(5)
<223> OTHER INFORMATION: Xaa at position 5 is L, I, V, or F
<220> FEATURE:
<221> NAME/KEY: MISC_FEATURE
<222> LOCATION: (6)..(6)
<223> OTHER INFORMATION: Xaa at position 6 is L, I, V, or F
<220> FEATURE:
<221> NAME/KEY: MISC_FEATURE
<222> LOCATION: (7)..(7)
<223> OTHER INFORMATION: Xaa at position 7 is M, A, D, isoD, E,
      g-glutamate, Q, N, S, and G
<220> FEATURE:
<221> NAME/KEY: MISC_FEATURE
<222> LOCATION: (8)..(8)
<223> OTHER INFORMATION: Xaa at position 8 is L, I, V, or F
<220> FEATURE:
<221> NAME/KEY: MISC_FEATURE
<222> LOCATION: (9)..(9)
<223> OTHER INFORMATION: Xaa at position 9 is L, I, V, or F
<220> FEATURE:
<221> NAME/KEY: MISC_FEATURE
<222> LOCATION: (10)..(10)
<223> OTHER INFORMATION: Xaa at position 10 is M, A, D, isoD, E,
      g-glutamate, Q, N, S, and G
<220> FEATURE:
<221> NAME/KEY: MISC_FEATURE
<222> LOCATION: (11)..(11)
<223> OTHER INFORMATION: Xaa at position 11 is M, A, D, isoD, E,
      g-glutamate, Q, N, S, and G
<220> FEATURE:
<221> NAME/KEY: MISC_FEATURE
<222> LOCATION: (12)..(12)
<223> OTHER INFORMATION: Xaa at position 12 is M, A, D, isoD, E,
      g-glutamate, Q, N, S, and G
<220> FEATURE:
<221> NAME/KEY: MISC_FEATURE
<222> LOCATION: (13)..(13)
<223> OTHER INFORMATION: Xaa at position 13 is L, I, V, or F
<220> FEATURE:
<221> NAME/KEY: MISC_FEATURE
<222> LOCATION: (14)..(14)
<223> OTHER INFORMATION: Xaa at position 14 is D, G, Q, or E
<220> FEATURE:
<221> NAME/KEY: MISC_FEATURE
<222> LOCATION: (15)..(15)
<223> OTHER INFORMATION: Xaa at position 15 is D, G, Q, or E

<400> SEQUENCE: 36

Xaa Xaa Xaa Xaa Xaa Xaa Xaa Xaa Xaa Xaa Xaa Xaa Xaa Xaa Xaa
1               5                   10                  15

<210> SEQ ID NO 37
<211> LENGTH: 15
<212> TYPE: PRT
<213> ORGANISM: Artificial
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: Xaa at position 1 is Q or E
<220> FEATURE:
<221> NAME/KEY: MISC_FEATURE
<222> LOCATION: (2)..(2)
<223> OTHER INFORMATION: Xaa at position 2 is Q or E
```

```
<220> FEATURE:
<221> NAME/KEY: MISC_FEATURE
<222> LOCATION: (3)..(3)
<223> OTHER INFORMATION: Xaa at position 3 is L, I, V, or F
<220> FEATURE:
<221> NAME/KEY: MISC_FEATURE
<222> LOCATION: (4)..(4)
<223> OTHER INFORMATION: Xaa at position 4 is M, A, D, isoD, E,
      g-glutamate, Q, N, S, or G
<220> FEATURE:
<221> NAME/KEY: MISC_FEATURE
<222> LOCATION: (5)..(5)
<223> OTHER INFORMATION: Xaa at position 5 is optional and, when
      present, is selected from D, isoD, E, g-glutamate, Q, N, S, and G
<220> FEATURE:
<221> NAME/KEY: MISC_FEATURE
<222> LOCATION: (6)..(6)
<223> OTHER INFORMATION: Xaa at position 6 is L, I, V, or F
<220> FEATURE:
<221> NAME/KEY: MISC_FEATURE
<222> LOCATION: (7)..(7)
<223> OTHER INFORMATION: Xaa at position 7 is L, I, V, or F
<220> FEATURE:
<221> NAME/KEY: MISC_FEATURE
<222> LOCATION: (8)..(8)
<223> OTHER INFORMATION: Xaa at position 8 is L, I, V, or F
<220> FEATURE:
<221> NAME/KEY: MISC_FEATURE
<222> LOCATION: (9)..(9)
<223> OTHER INFORMATION: Xaa at position 9 is M, A, D, isoD, E,
      g-glutamate, Q, N, S, or G
<220> FEATURE:
<221> NAME/KEY: MISC_FEATURE
<222> LOCATION: (10)..(10)
<223> OTHER INFORMATION: Xaa at position 10 is L, I, V, or F
<220> FEATURE:
<221> NAME/KEY: MISC_FEATURE
<222> LOCATION: (11)..(11)
<223> OTHER INFORMATION: Xaa at position 11 is L, I, V, or F
<220> FEATURE:
<221> NAME/KEY: MISC_FEATURE
<222> LOCATION: (12)..(12)
<223> OTHER INFORMATION: Xaa at position 12 is M, A, D, isoD, E,
      g-glutamate, Q, N, S, or G
<220> FEATURE:
<221> NAME/KEY: MISC_FEATURE
<222> LOCATION: (13)..(13)
<223> OTHER INFORMATION: Xaa at position 13 is M, A, D, isoD, E,
      g-glutamate, Q, N, S, or G
<220> FEATURE:
<221> NAME/KEY: MISC_FEATURE
<222> LOCATION: (14)..(14)
<223> OTHER INFORMATION: Xaa at position 14 is M, A, D, isoD, E,
      g-glutamate, Q, N, S, or G
<220> FEATURE:
<221> NAME/KEY: MISC_FEATURE
<222> LOCATION: (15)..(15)
<223> OTHER INFORMATION: Xaa at position 15 is L, I, V, or F

<400> SEQUENCE: 37

Xaa Xaa Xaa Xaa Xaa Xaa Xaa Xaa Xaa Xaa Xaa Xaa Xaa Xaa Xaa
1               5                   10                  15

<210> SEQ ID NO 38
<211> LENGTH: 21
<212> TYPE: PRT
<213> ORGANISM: Artificial
<220> FEATURE:
<223> OTHER INFORMATION: P5

<400> SEQUENCE: 38

Ser Ala Gly Ser Glu Gln Gln Leu Asp Leu Leu Leu Met Phe Ile Met
1               5                   10                  15

Met Met Leu Gln Gln
            20
```

```
<210> SEQ ID NO 39
<211> LENGTH: 22
<212> TYPE: PRT
<213> ORGANISM: Artificial
<220> FEATURE:
<223> OTHER INFORMATION: P5a

<400> SEQUENCE: 39

Ser Ala Gly Ser Glu Gln Gln Leu Asp Gln Leu Leu Leu Met Phe Ile
1               5                   10                  15

Met Met Met Leu Gln Gln
            20

<210> SEQ ID NO 40
<211> LENGTH: 20
<212> TYPE: PRT
<213> ORGANISM: Artificial
<220> FEATURE:
<223> OTHER INFORMATION: P5-21

<400> SEQUENCE: 40

Ser Glu Glu Gln Leu Glu Leu Leu Leu Ala Phe Ile Ala Ala Ala Leu
1               5                   10                  15

Gln Gln Glu Glu
            20

<210> SEQ ID NO 41
<211> LENGTH: 21
<212> TYPE: PRT
<213> ORGANISM: Artificial
<220> FEATURE:
<223> OTHER INFORMATION: P5-25

<400> SEQUENCE: 41

Ser Glu Glu Glu Glu Gln Leu Asp Gln Leu Leu Leu Ala Phe Ile Ala
1               5                   10                  15

Ala Ala Leu Gln Gln
            20

<210> SEQ ID NO 42
<211> LENGTH: 24
<212> TYPE: PRT
<213> ORGANISM: Artificial
<220> FEATURE:
<223> OTHER INFORMATION: K to E P1-18t variant

<400> SEQUENCE: 42

Asn Gln Gly Ile Ser Glu Glu Gln Leu Asp Gln Leu Leu Thr Gln Leu
1               5                   10                  15

Ile Thr Ala Leu Leu Gln Gln Arg
            20

<210> SEQ ID NO 43
<211> LENGTH: 24
<212> TYPE: PRT
<213> ORGANISM: Artificial
<220> FEATURE:
<223> OTHER INFORMATION: K to E P4-14s variant

<400> SEQUENCE: 43

Ser Gln Gly Ile Ser Glu Glu Gln Leu Asp Gln Leu Leu Ser Gln Leu
1               5                   10                  15

Ile Gln Ala Leu Leu Gln Pro Arg
```

20

<210> SEQ ID NO 44
<211> LENGTH: 28
<212> TYPE: PRT
<213> ORGANISM: Artificial
<220> FEATURE:
<223> OTHER INFORMATION: K/R to E P18 variant

<400> SEQUENCE: 44

Gln Gln Pro Ile Asp Glu Gln Thr Ile Glu Gln Met Ala Gln Leu Leu
1               5                   10                  15
Ala Gln Leu Leu Glu Ser Leu Leu Ser Pro Gln Arg
            20                  25

<210> SEQ ID NO 45
<211> LENGTH: 26
<212> TYPE: PRT
<213> ORGANISM: Artificial
<220> FEATURE:
<223> OTHER INFORMATION: K to E P19 variant

<400> SEQUENCE: 45

Ile Thr Pro Asp Gly Gln Gly Gly Gly Gln Ile Gly Asp Asn Pro Leu
1               5                   10                  15
Leu Glu Ala Met Leu Glu Leu Ile Ala Arg
            20                  25

<210> SEQ ID NO 46
<211> LENGTH: 18
<212> TYPE: PRT
<213> ORGANISM: Artificial
<220> FEATURE:
<223> OTHER INFORMATION: K to E P1-29 variant

<400> SEQUENCE: 46

Asn Gln Gly Ile Ser Glu Glu Gln Leu Asp Gln Leu Leu Thr Gln Leu
1               5                   10                  15
Ile Arg

<210> SEQ ID NO 47
<211> LENGTH: 18
<212> TYPE: PRT
<213> ORGANISM: Artificial
<220> FEATURE:
<223> OTHER INFORMATION: K to E P4-111 variant

<400> SEQUENCE: 47

Ser Gln Gly Ile Ser Glu Glu Gln Leu Asp Gln Leu Leu Ser Gln Leu
1               5                   10                  15
Ile Arg

<210> SEQ ID NO 48
<211> LENGTH: 34
<212> TYPE: PRT
<213> ORGANISM: Artificial
<220> FEATURE:
<223> OTHER INFORMATION: K to E P14 variant

<400> SEQUENCE: 48

Gln Ala Gly Pro Gln Ser Ala Asn Glu Thr Gly Asn Val Asp Asp Ala
1               5                   10                  15
Asn Asn Gln Asp Pro Met Gln Ala Leu Met Gln Leu Leu Glu Asp Leu
            20                  25                  30

Val Arg

```
<210> SEQ ID NO 49
<211> LENGTH: 27
<212> TYPE: PRT
<213> ORGANISM: Artificial
<220> FEATURE:
<223> OTHER INFORMATION: P17/P18 consensus
<220> FEATURE:
<221> NAME/KEY: MISC_FEATURE
<222> LOCATION: (1)..(1)
<223> OTHER INFORMATION: Xaa at position 1 is Q, S, E, g-glutamate, A,
      T, G, D, isoD, N, K, or R
<220> FEATURE:
<221> NAME/KEY: MISC_FEATURE
<222> LOCATION: (2)..(2)
<223> OTHER INFORMATION: Xaa at position 2 is Q, S, E, g-glutamate, A,
      T, G, D, isoD, N, K, or R
<220> FEATURE:
<221> NAME/KEY: MISC_FEATURE
<222> LOCATION: (3)..(3)
<223> OTHER INFORMATION: Xaa at position 3 is P, Q, S, E, g-glutamate,
      A, T, G, D, isoD, N, K, or R
<220> FEATURE:
<221> NAME/KEY: MISC_FEATURE
<222> LOCATION: (4)..(4)
<223> OTHER INFORMATION: Xaa at position 4 is I, Q, S, E, g-glutamate,
      A, T, G, D, N, isoD, K, or R
<220> FEATURE:
<221> NAME/KEY: MISC_FEATURE
<222> LOCATION: (5)..(5)
<223> OTHER INFORMATION: Xaa at position 5 is D, isoD, S, E,
      g-glutamate, A, T, G, N, Q, K, or R
<220> FEATURE:
<221> NAME/KEY: MISC_FEATURE
<222> LOCATION: (6)..(6)
<223> OTHER INFORMATION: Xaa at position 6 is R, Q, S, E, g-glutamate,
      A, T, G, D, isoD, N, or K
<220> FEATURE:
<221> NAME/KEY: MISC_FEATURE
<222> LOCATION: (7)..(7)
<223> OTHER INFORMATION: Xaa at position 7 is Q, S, E, g-glutamate, A,
      T, G, D, isoD, N, K, or R
<220> FEATURE:
<221> NAME/KEY: MISC_FEATURE
<222> LOCATION: (8)..(8)
<223> OTHER INFORMATION: Xaa at position 8 is T, Q, S, E, g-glutamate,
      A, G, D, isoD, N, K, or R
<220> FEATURE:
<221> NAME/KEY: MISC_FEATURE
<222> LOCATION: (9)..(9)
<223> OTHER INFORMATION: Xaa at position 9 is I, Q, S, E, g-glutamate,
      A, T, G, D, isoD, N, K, or R
<220> FEATURE:
<221> NAME/KEY: MISC_FEATURE
<222> LOCATION: (10)..(10)
<223> OTHER INFORMATION: Xaa at position 10 is E, g-glutamate, Q, S, A,
      T, G, D, isoD, N, K, or R
<220> FEATURE:
<221> NAME/KEY: MISC_FEATURE
<222> LOCATION: (11)..(11)
<223> OTHER INFORMATION: Xaa at position 11 is Q, S, E, g-glutamate, A,
      T, G, D, isoD, N, K, or R
<220> FEATURE:
<221> NAME/KEY: MISC_FEATURE
<222> LOCATION: (12)..(12)
<223> OTHER INFORMATION: Xaa at position 12 is L or M
<220> FEATURE:
<221> NAME/KEY: MISC_FEATURE
<222> LOCATION: (13)..(13)
<223> OTHER INFORMATION: Xaa at position 13 is A, S, T, G, D, isoD, E,
      g-glutamate, Q, N, K, or R
<220> FEATURE:
<221> NAME/KEY: MISC_FEATURE
<222> LOCATION: (14)..(14)
<223> OTHER INFORMATION: Q, A, S, T, G, D, isoD, E, g-glutamate, N, K,
      or R
```

```
<220> FEATURE:
<221> NAME/KEY: MISC_FEATURE
<222> LOCATION: (15)..(15)
<223> OTHER INFORMATION: Xaa at position 15 is L
<220> FEATURE:
<221> NAME/KEY: MISC_FEATURE
<222> LOCATION: (16)..(16)
<223> OTHER INFORMATION: Xaa at position 16 is L
<220> FEATURE:
<221> NAME/KEY: MISC_FEATURE
<222> LOCATION: (17)..(17)
<223> OTHER INFORMATION: Xaa at position 17 is A, S, T, G, D, isoD, E,
     g-glutamate, Q, N, K, or R
<220> FEATURE:
<221> NAME/KEY: MISC_FEATURE
<222> LOCATION: (18)..(18)
<223> OTHER INFORMATION: Xaa at position 18 is Q, A, S, T, G, D, isoD,
     E, g-glutamate, N, K, or R
<220> FEATURE:
<221> NAME/KEY: MISC_FEATURE
<222> LOCATION: (19)..(19)
<223> OTHER INFORMATION: Xaa at position 19 is L
<220> FEATURE:
<221> NAME/KEY: MISC_FEATURE
<222> LOCATION: (20)..(20)
<223> OTHER INFORMATION: Xaa at position 20 is L
<220> FEATURE:
<221> NAME/KEY: MISC_FEATURE
<222> LOCATION: (21)..(21)
<223> OTHER INFORMATION: Xaa at position 21 is K, A, S, T, G, D, isoD,
     E, g-glutamate, Q, N, or R
<220> FEATURE:
<221> NAME/KEY: MISC_FEATURE
<222> LOCATION: (22)..(22)
<223> OTHER INFORMATION: Xaa at position 22 is S, A,T, G, D, isoD, E,
     g-glutamate, Q, N, K, or R
<220> FEATURE:
<221> NAME/KEY: MISC_FEATURE
<222> LOCATION: (23)..(23)
<223> OTHER INFORMATION: Xaa at position 23 is L
<220> FEATURE:
<221> NAME/KEY: MISC_FEATURE
<222> LOCATION: (24)..(24)
<223> OTHER INFORMATION: Xaa at position 24 is L
<220> FEATURE:
<221> NAME/KEY: MISC_FEATURE
<222> LOCATION: (25)..(25)
<223> OTHER INFORMATION: Xaa at position 25 is S, A, T, G, D, isoD, E,
     g-glutamate, Q, N, K, or R
<220> FEATURE:
<221> NAME/KEY: MISC_FEATURE
<222> LOCATION: (26)..(26)
<223> OTHER INFORMATION: Xaa at position 26 is P, S, A, T, G, D, isoD,
     E, g-glutamate, Q, N, K, or R
<220> FEATURE:
<221> NAME/KEY: MISC_FEATURE
<222> LOCATION: (27)..(27)
<223> OTHER INFORMATION: Xaa at position 27 is Q, S, A, T, G, D, isoD,
     E, g-glutamate, N, K, or R

<400> SEQUENCE: 49

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25
```

BENEFICIAL MICROBES FOR DELIVERY OF EFFECTOR PEPTIDES OR PROTEINS AND USE THEREOF

This application claims the priority benefit of U.S. Provisional Patent Application Ser. No. 62/319,150, filed Apr. 6, 2016, which is hereby incorporated by reference in its entirety.

FIELD OF THE INVENTION

The present invention relates to recombinant beneficial microbes for delivery of plant effector proteins or polypeptides and their use for inducing active plant responses including, among others, growth enhancement, disease resistance, pest or insect resistance, and stress resistance.

BACKGROUND OF THE INVENTION

The identification and isolation of harpin proteins came from basic research at Cornell University attempting to understand how plant pathogenic bacteria interact with plants. A first line of defense is the hypersensitive response (HR), a localized plant cell death at the site of infection. Cell death creates a physical barrier to movement of the pathogen and in some plants dead cells can release compounds toxic to the invading pathogen. Research had indicated that pathogenic bacteria were likely to have a single factor that was responsible for triggering the HR. A basic aim of the Cornell research was to identify a specific bacterial protein responsible for eliciting the HR. The target protein was known to be encoded by one of a group of bacteria genes called the Hypersensitive Response and Pathogenicity (hrp) gene cluster. The hrp cluster in the bacterium *Erwinia amylovora* (Ea), which causes fire blight in pear and apple, was dissected and a single protein was identified that elicited HR in certain plants. This protein was given the name harpin (and, later, harpin$_{Ea}$) and the corresponding gene designated hrpN. This was the first example of such a protein and gene identified from any bacterial species.

A number of different harpin proteins have since been identified from *Erwinia, Pseudomonas, Ralstonia, Xanthomonas,* and *Pantoea* species, among others. Harpin proteins, while diverse at the primary amino acid sequence level, share common biochemical and biophysical characteristics as well as biological functions. Based on their unique properties, the harpin proteins are regarded in the literature as belonging to a single class of proteins.

Subsequent to their identification and isolation, it was thereafter discovered that harpins could elicit disease resistance in plants and increase plant growth. An important early finding was that application of purified harpin protein made a plant resistant to a subsequent pathogen attack, and in locations on the plant well away from the injection site. This meant that harpin proteins can trigger a Systemic Acquired Resistance (SAR), a plant defense mechanism that provides resistance to a variety of viral, bacterial, and fungal pathogens.

In crop protection, there is a continuous need for compositions that improve the health of plants. Healthier plants are desirable since they result in better yields and/or a better quality of the plants or crops. Healthier plants also better resist biotic and abiotic stress. A high resistance against biotic stresses in turn allows the growers to reduce the quantity of pesticides applied and consequently to slow down the development of resistances against the respective pesticides.

Harpin$_{\alpha,\beta}$ is a fusion protein that is derived from several different harpins. Harpin$_{\alpha,\beta}$ has been shown to suppress nematode egg production, enhance the growth, quality and yield of a plant, and increase a plant's vigor. Its amino acid and nucleotide sequences are described in detail in U.S. Application Publ. No. 2010/0043095.

To date, harpin and harpin$_{\alpha,\beta}$ production and their use in agricultural and horticultural applications have been as a powdered solid coated on starch. This limits the use and versatility of the harpin proteins, because liquid suspensions of the powdered harpin proteins in water have an effective useful life of only 48-72 hours before significant degradation and loss of activity occurs. Another problem with harpin solutions is protein solubility and stability.

Once solutions of the harpin proteins or polypeptides are applied topically to plants, the proteins or polypeptides will induce an active plant response, but the response typically is of a limited duration insofar as multiple applications are used over the course of a growing season. Indeed, the commercial instructions for using harpin$_{\alpha,\beta}$-containing products recommend using liquid formulations within a short period of time (e.g., 8 or 24 hours) of mixing and, depending on the type of crop and benefits sought, multiple applications are often recommended. It would be desirable, therefore, to identify a mechanism for delivery of protein-based elicitor peptides that can be effective for prolonged period of time during the growing season so as to minimize the number of applications while also enhancing efficacy thereof.

The present invention is directed to overcoming these and other deficiencies in the art.

SUMMARY OF THE INVENTION

A first aspect of the invention relates to a recombinant host cell comprising a transgene that comprises a promoter-effective nucleic acid molecule operably coupled to a nucleic acid molecule that encodes a plant effector protein or polypeptide, wherein the recombinant host cell is a microbe that imparts a first benefit to a plant grown in the presence of the recombinant microbe and the plant effector protein or polypeptide imparts a second benefit to the plant grown in the presence of the recombinant microbe.

A second aspect of the invention relates to a composition that includes a plurality of recombinant host cells according to the first aspect of the invention.

A third aspect of the invention relates to a method for treating plant seeds. This method includes: providing one or more plant seeds and applying to the provided one or more plant seeds either a recombinant host cell according to the first aspect of the invention, or a composition according to the second aspect of the invention.

A fourth aspect of the invention relates to a method for treating plants. This method includes: providing one or more plants and applying to the provided one or more plants either a recombinant host cell according to the first aspect of the invention, or a composition according to the second aspect of the invention.

A fifth aspect of the invention relates to a method for treating plants. This method includes: applying to a locus where plants are being grown or are expected to be grown either a recombinant host cell according to the first aspect of the invention, or a composition according to the second aspect of the invention.

A sixth aspect of the invention relates to a method of imparting disease resistance to plants. This method includes: applying an effective amount of recombinant host cell according to the first aspect of the invention, or a composition according to the second aspect of the invention to a plant or plant seed or the locus where the plant is growing or is expected to grow, wherein said applying is effective to impart disease resistance.

A seventh aspect of the invention relates to a method of enhancing plant growth. This method includes: applying an effective amount of recombinant host cell according to the first aspect of the invention, or a composition according to the second aspect of the invention to a plant or plant seed or the locus where the plant is growing or is expected to grow, wherein said applying is effective to enhance plant growth.

An eighth aspect of the invention relates to a method of increasing a plant's tolerance and resistance to biotic stressors. This method includes: applying an effective amount of recombinant host cell according to the first aspect of the invention, or a composition according to the second aspect of the invention to a plant or plant seed or the locus where the plant is growing or is expected to grow, wherein said applying is effective to increase the plant's tolerance and resistance to biotic stress factors selected from the group consisting of pests such as insects, arachnids, nematodes, weeds, and combinations thereof.

A ninth aspect of the invention relates to a method of increasing a plant's tolerance to abiotic stress. This method includes: applying an effective amount of recombinant host cell according to the first aspect of the invention, or a composition according to the second aspect of the invention to a plant or plant seed or the locus where the plant is growing or is expected to grow, wherein said applying is effective to increase the plant's tolerance to abiotic stress factors selected from the group consisting of salt stress, water stress (including drought and flooding), ozone stress, heavy metal stress, cold stress, heat stress, nutritional stress (phosphate, potassium, nitrogen deficiency), bleaching and light-induced stress, and combinations thereof.

A tenth aspect of the invention relates to a method imparting desiccation resistance to cuttings removed from ornamental plants. This method includes: applying recombinant host cell according to the first aspect of the invention, or a composition according to the second aspect of the invention to a plant or the locus where the plant is growing, wherein said applying is effective to impart desiccation resistance to cuttings removed from the ornamental plant.

An eleventh aspect of the invention relates to a method of imparting post-harvest disease or post-harvest desiccation resistance to a fruit or vegetable. This method includes: applying an effective amount of recombinant host cell according to the first aspect of the invention, or a composition according to the second aspect of the invention to a plant containing a fruit or vegetable or the locus where the plant is growing; or applying an effective amount of the recombinant host cell or the composition to a harvested fruit or vegetable, wherein said applying is effective to impart post-harvest disease resistance or desiccation resistance to the fruit or vegetable.

A twelfth aspect of the invention relates to a method of enhancing the longevity of fruit or vegetable ripeness. This method includes: applying an effective amount of recombinant host cell according to the first aspect of the invention, or a composition according to the second aspect of the invention to a plant containing a fruit or vegetable or the locus where the plant is growing; or applying an effective amount of the recombinant host cell or the composition to a harvested fruit or vegetable, wherein said applying is effective to enhance the longevity of fruit or vegetable ripeness.

A thirteenth aspect of the invention relates to a method of modulating one or more biological signaling processes of a plant. This method includes: applying an effective amount of recombinant host cell according to the first aspect of the invention, or a composition according to the second aspect of the invention to a plant or the locus where the plant is growing, wherein said applying is effective in modulating one or more biochemical signaling processes.

A growing aspect of the commercial crop protection market involves the use of living biological agents, including bacteria, fungi, and other beneficial microbes. These organisms may directly or indirectly antagonize plant pathogens through killing, competition for resources, and competition for space on plant surfaces. In addition, some beneficial microbes may set up a direct symbiotic relationship with the host plant. Since there are significant benefits to a grower in reducing the number of products applied to the field as well as reducing the total number of applications, the present invention affords many benefits to growers by using a long-lived, recombinant microorganism to produce a non-native harpin protein or effector peptide for inducing plant stimulation. Thus, in a single application a plant grower can obtain both the long-lasting benefits afforded by the microorganism and the harpin protein or effector peptide expressed by the microorganism.

DETAILED DESCRIPTION OF THE INVENTION

One aspect of the invention relates to a recombinant host cell comprising a transgene that comprises a promoter-effective nucleic acid molecule operably coupled to a nucleic acid molecule that encodes a plant effector protein or polypeptide, wherein the recombinant host cell is a microbe that imparts a first benefit to a plant grown in the presence of the recombinant microbe and the plant effector protein or polypeptide imparts a second benefit to the plant grown in the presence of the recombinant microbe.

The terms defined immediately below are more fully defined by reference to the specification as a whole.

The term "transgene" refers to a gene introduced into the beneficial microbe, making the beneficial microbe recombinant. The introduction of a transgene into the beneficial microbe has the potential to change the phenotype of that microbe, in the present case due to the expression of the plant effector protein or polypeptide by the recombinant beneficial microbe. The construction of a transgene involves the assembly of a few main parts, including a promoter sequence (defined below), a protein coding sequence (defined below), and a stop codon.

The term "promoter" is defined herein as a nucleic acid that directs transcription of a downstream polynucleotide in a cell. In certain cases, the polynucleotide may contain a coding sequence and the promoter may direct the transcription of the coding sequence into translatable RNA.

The term "coding sequence" is defined herein as a nucleic acid that, when placed under the control of appropriate control sequences including a promoter, is transcribed into mRNA which can be translated into a polypeptide. A coding sequence may contain a single open reading frame, or several open reading frames separated by introns, for example. A coding sequence may be cDNA, genomic DNA, synthetic DNA or recombinant DNA, for example. A coding sequence generally starts at a start codon (e.g., ATG) and ends at a stop codon (e.g., UAA, UAG and UGA).

The term "recombinant" refers to a polynucleotide or polypeptide that does not naturally occur in a host cell, as well as host cells that contain a non-naturally occurring polynucleotide or polypeptide. A recombinant molecule may contain two or more naturally occurring sequences that are linked together in a way that does not occur naturally. Thus, a "recombinant host cell" refers to a host cell that is non-naturally occurring, e.g., through the introduction of a recombinant polynucleotide (or transgene) into the host cell.

The term "operably coupled" refers to a juxtaposition, wherein elements are in an arrangement allowing them to be functionally related. For example, a promoter is operably linked to a coding sequence if it controls the transcription of the sequence, and a signal sequence is operably linked to a protein if the signal sequence directs the protein through the secretion system of a host cell. Generally, this operable linkage is reflected by the relative positioning of elements along a DNA strand.

The term "nucleic acid" encompasses DNA, RNA, single or doubled stranded and modification thereof. The terms "nucleic acid" and "polynucleotide" may be used interchangeability herein.

As used herein, the terms "polypeptide" and "protein" are used interchangeably and include reference to a polymer of any number of amino acid residues. The terms apply to amino acid polymers in which one or more amino acid residue is an artificial chemical analog of a corresponding naturally occurring amino acid, as well as to naturally occurring amino acid polymers. The terms also apply to polymers containing conservative amino acid substitutions such that the polypeptide remains functional. "Peptides" are polypeptides having less than 50 amino acid residues.

A "host cell" is a cell that contains a subject recombinant nucleic acid, either in the genome of the host cell or in an extrachromosomal vector that replicates autonomously from the genome of the host cell. A host cell may be any cell type.

In various embodiments, a host cell comprising a subject recombinant nucleic acid is provided. The host cell may be any cell type, but is preferably a microbe, e.g., a bacterial or fungal (such as a non-filamentous or filamentous fungal) host cell.

In certain embodiments, the microbe is a beneficial microbe that imparts a benefit to a plant grown in the presence of the microbe. A recombinant beneficial microbe also imparts a benefit to a plant grown in the presence of the microbe, but due to the presence of a recombinant polynucleotide the recombinant beneficial microbe also expresses a plant effector protein or polypeptide that imparts a second benefit to the plant grown in the presence of the recombinant microbe.

The term "filamentous fungi" refers to all filamentous forms of the subdivision Eumycotina (see Alexopoulos, C. J., INTRODUCTORY MYCOLOGY, Wiley, New York (1962), which is hereby incorporated by reference in its entirety). These fungi are characterized by a vegetative mycelium with a cell wall composed of chitin, glucans, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic.

In certain embodiments, the beneficial microbe is a bacterium.

Suitable beneficial bacterium include, without limitation, *Pseudomonas* (e.g., *P. fluorescens, P. aureofaciens, P. chlororaphis, P. solanacearum*, and *P. syringae*), *Sphingomonas* (e.g., *S. phyllosphaerae, S. roseiflava, S. melonis, S. azotifigens*, and *S. mali*) (see also Innerebner et al., "Protection of *Arabidopsis thaliana* Against Leaf-Pathogenic *Pseudomonas syringae* by *Sphingomonas* Strains in a Controlled Model System," *Appl. Environ. Microbiol.* 77:3202-3210 (2011), which is hereby incorporated by reference in its entirety), *Bacillus* (*B. firmus, B. licheniformis, B. megaterium, B. mucilaginous, B. pumilus, B. subtilis*, and *B. subtilis* var. *amyloliquefaciens*), *Streptomyces* (e.g., *S. griseoviridis* and *S. lydicus*), *Rhizobium* (e.g., *R. meliloti, R. trifolii, R. leguminosarum, R. phaseolin, R. lupine*, and *R. japonicum*), *Frankia* (e.g., *F. alni*), and *Azospirillum* (e.g., *A. brasilense* and *A. lipoferum*).

Additional beneficial bacterium, include, without limitation, *Agrobacterium radiobacter, Azotobacter chroococcum, Burkholderia cepacia, Delftia acidovorans, Paenobacillus macerans, Pantoea agglomerans*, and *Serratia entomophilia*.

In certain embodiments, the host cell may be a filamentous fungal host cell. In some embodiments, the host cell may be a cell of a strain that has a history of use for production of proteins that has GRAS status, i.e., a Generally Recognized as Safe, by the FDA.

In some embodiments, subject fungal host cells may be of a strain of *Aspergillus niger* which include ATCC 22342, ATCC 44733, ATCC 14331, ATCC 11490, NRRL 3112, and strains derived therefrom. In some embodiments, subject fungal cells may be strains of *Trichoderma* (e.g. *T. harzianum, T. viride, T. koningi, T. reesei* and *T. hamatum*) which include functional equivalents of RL-P37 (Sheir-Neiss et al. *Appl. Microbiol. Biotechnology* 20:46-53 (1984), which is hereby incorporated by reference in its entirety). Other useful host strains include, without limitation, NRRL 15709, ATCC 13631, ATCC 26921 (QM 9414) ATCC 32098, ATCC 32086, and ATCC 56765 (RUT-30). In some embodiments, subject fungal cells may be strains of non-filamentous fungal yeasts, including, without limitation, strains of *Rhodotorula* (e.g., *R. graminis* WP1 and *R. mucilaginosa*) (see U.S. Pat. No. 8,728,781 and Xin et al., "Characterization of Three Endophytic, Indole-3-Acetic Acid-Producing Yeasts Occurring in *Populus* Trees," *Mycol. Res.* 113:973-980 (2009), which are hereby incorporated by reference in their entirety).

In some embodiments, a host cell may be one wherein native genes have been deleted or inactivated. For example, genes corresponding to protease genes (e.g., aspartyl protease, (Berka et al. *Gene* 86:153-162 (1990) and U.S. Pat. No. 6,509,171, which are hereby incorporated by reference in their entirety)) or genes corresponding to cellulase genes (e.g., cbh1, cbh2 and egl1, and eg12) may be deleted or inactivated. One example of this is the quad deleted strain of *T. reesei* disclosed in PCT Application Publ. No. WO 05/001036, which is hereby incorporated by reference in its entirety.

In certain embodiments, the recombinant microbe is epiphytic. Such a microbe lives non-parasitically on the surface of the host plant tissues, including without limit, at the surface of leaves or near roots.

In other embodiments, the recombinant microbe is endophytic. Such a microbe lives at least part of its life-cycle non-parasitically within plant tissues, including without limit, within leaves, roots, and stems.

One aspect of the invention is a DNA molecule capable of directing production of the plant bioactive polypeptide or protein. This DNA molecule contains several component sequences. These include but are not limited to the sequence coding the open reading frame for the plant effector protein or polypeptide, a ribosome-binding sequence, and a promoter. Additional sequences may include a selectable marker and an origin of replication. Optional sequences include secretion signals and sequences for genomic integration.

The term "signal sequence" or "signal peptide" refers to a sequence of amino acids at the N-terminal portion of a protein, which facilitates the secretion of the mature form of the protein outside the host cell. The mature form of the extracellular protein lacks the signal sequence which is cleaved off during the secretion process.

A promoter sequence directs the recruitment of an RNA polymerase complex to the DNA template. The choice of promoter sequence determines the conditions under which the transgene will be transcribed to allow for protein expression. Promoter sequences differ between species as they must interact with host cell transcription factors. Although strong promoters are often preferred for protein expression during fermentation, the present invention is not limited to strong, exponential growth promoters. Weak promoters and promoters activated during stationary phase and slow-growth conditions are also appropriate.

A preferred constitutively active promoter sequence for *B. subtilis* is the aprE promoter sequence as described by Park et al., "*Bacillus subtilis* subtilisin gene (aprE) is expressed from a sigma A (sigma 43) promoter in vitro and in vivo," *J Bact.* 171:2657-2665 (1989), which is hereby incorporated by reference in its entirety. Another preferred constitutively active weak promoter sequence is PliaG promoter as described by Jordan et al., "Regulation of LiaRS-dependent Gene Expression in *Bacillus subtilis*: Identification of Inhibitor Proteins, Regulator Binding Sites and Target Genes of a Conserved Cell Envelope Stress-sensing Two-component System," *J Bacteriol.* 188: 5153-5166 (2006), which is hereby incorporated by reference in its entirety. Another preferred promoter sequence is the ctc promoter that is activated under nutrient and other stress conditions, as described by Igo and Losick, "Regulation of a Promoter That is Utilized by Minor Forms of RNA Polymerase Holoenzyme in *Bacillus subtilis*," *J Mol. Biol.* 191: 615-624 (1986), which is hereby incorporated by reference in its entirety. More recently, additional tools have been developed for protein expression in *B. subtilis*, including a number of promoters, as summarized by Radeck et al., "The *Bacillus* BioBrick Box: Generation and Evaluation of Essential Genetic Building Blocks for Standardized Work with *Bacillus subtilis*," *J Biol. Eng.* 7:29 (2013), which is hereby incorporated by reference in its entirety. Additional information is available online at the iGEM Registry of Standard Biological Parts (see http://parts.igem.org/Promoters/Catalog/B._subtilis/Constitutive and http://parts.igem.org/Bacillus_subtilis).

In certain embodiments, the polynucleotide may be codon optimized for expression of the protein in a particular host cell. Since codon usage tables listing the usage of each codon in many cells are known in the art (see, e.g., Nakamura et al, *Nucl. Acids Res.* 28: 292 (2000), which is hereby incorporated by reference in its entirety) or readily derivable, such nucleic acids can be readily designed giving the amino acid sequence of a protein to be expressed.

In addition to a coding sequence, the recombinant nucleic acid may in certain embodiments further contain other elements that are necessary for expression of the protein in the host cell. For example, the nucleic acid may contain a transcriptional terminator, and 5' and 3' UTR sequences. Suitable 5' UTR sequences may be obtained from the *T. reesei* cbh1, cbh2, egl1, egl2, egl5, xln1 and xln2 genes, for example. Suitable terminators include the *T. reesei* cbh1, cbh2, egl1, egl2, egl5, xln1 and xln2 terminators, and many others, including, for example, the terminators from *A. niger* or *A. awamori* glucoamylase genes (Nunberg et al. *Mol. Cell. Biol.* 4: 2306-2353 (1984); Boel et al., *EMBO J.* 3:1097-1102 (1984), each of which is hereby incorporated by reference in its entirety), *Aspergillus nidulans* anthranilate synthase genes, *Aspergillus oryzae* TAKA amylase genes, or *A. nidulans* trpc (Punt et al., *Gene* 56:117-124 (1987), which is hereby incorporated by reference in its entirety). The promoter and/or terminator may be native or non-endogenous to the host cell. In certain cases, the promoter and protein coding sequence may be separated by a sequence encoding a 5' untranslated region, for example.

As will be discussed in greater detail below, a subject recombinant nucleic acid may be present in a vector, or integrated into a genome (i.e., the nuclear genome) of a host cell.

The term "vector" is defined herein as a polynucleotide designed to carry nucleic acid sequences to be introduced into one or more cell types. Vectors include cloning vectors, expression vectors, shuttle vectors, plasmids, phage or virus particles, DNA constructs, cassettes and the like. Expression vectors may include regulatory sequences such as promoters, signal sequences, a coding sequences and transcription terminators.

An "expression vector" as used herein means a DNA construct comprising a coding sequence that is operably linked to suitable control sequences capable of effecting expression of a protein or polypeptide in a suitable host. Such control sequences may include a promoter to effect transcription, an optional operator sequence to control transcription, a sequence encoding suitable ribosome binding sites on the mRNA, enhancers and sequences which control termination of transcription and translation.

In certain embodiments, the expression vector comprises an origin of replication operable in the recombinant host cell.

The term "DNA construct" as used herein means a nucleic acid sequence that comprises at least two DNA polynucleotide fragments.

A subject recombinant nucleic acid may be present in a vector, e.g., a phage, plasmid, viral, or retroviral vector that autonomously replicates in a host cell. In certain embodiments, the vector may be an expression vector for expressing a protein or polypeptide in a host cell. In certain embodiments, the vector may be an expression vector for expressing a subject polypeptide in a filamentous fungal cell.

Vectors for expression of recombinant proteins are well known in the art (Ausubel, et al, Short Protocols in Molecular Biology, 3rd ed., Wiley & Sons (1995); Sambrook, et al., Molecular Cloning: A Laboratory Manual, Second Edition, (1989) Cold Spring Harbor, N.Y., each of which is hereby incorporated by reference in its entirety).

A subject vector may be constructed using well known techniques as is generally described for example in EP Application Publication 0215594, which is hereby incorporated by reference in its entirety. Once the fusion DNA construct is made it may be incorporated into any number of vectors as is known in the art. While the DNA construct will preferably include a promoter sequence, in some embodiments the vector will include regulatory sequences functional in the host to be transformed, such as promoters, ribosomal binding sites, transcription start and stop sequences, terminator sequences, polyadenylation signals, enhancers and/or activators.

Polypeptide expression systems can be created using existing plasmid systems by one skilled in the art. One notable guideline is that regulation of polypeptide expression should be well controlled. High polypeptide concentrations detected by the plant will likely trigger an intense immune response with widespread cell death characteristic of the hypersensitive response. In contrast, lower polypeptide expression levels should stimulate desired immunity while minimizing cell death. This effect may be further balanced by careful choice of secretion sequences. Expression of polypeptides in *Pseudomonas fluorescens* may be accomplished using the expression strains and tools described by Retallack et al., "Reliable protein production in a *Pseudomonas fluorescens* expression system," *Protein Expression and Purification* 81:157-65 (2012), which is hereby incorporated by reference in its entirety. Expression of peptides in *Bacillus subtilis* can be accomplished through vectors utilizing a subtilisin (aprE) promoter system. This can optionally be augmented using signal peptides to direct secretion of the peptide outside of the microbe. These functions are implemented in the "*Bacillus Subtilis* Secretory Protein Expression System" manual available from Clontech, which is hereby incorporated by reference in its entirety. Expression of proteins in *Streptomyces* has been demonstrated using plasmids as described by Fernandez-Abalos et al., "Posttranslational Processing of the Xylanase Xys1 L From *Streptomyces halstedii* JM8 is Carried Out by Secreted Serine Proteases," *Microbiology* 149:1623-32 (2003), which is hereby incorporated by reference in its entirety. Additional peptide expression systems can be produced by one skilled in the art.

Depending on the species of microbe chosen, the inserted sequences may exist as a circular plasmid that is independently propagated within the cell. Briefly, a plasmid incorporates all of the necessary DNA sequences for protein expression along with the optional sequences described below. A plasmid also requires an origin of replication, which is necessary for replication and maintenance of the plasmid. Optionally, a plasmid can contain a second origin of replication specific for *E. coli*, including the well-known pMB1 origin of replication present in the pBR322 vector as described by Sutcliffe, "Complete Nucleotide Sequence of the *Escherichia coli* Plasmid pBR322," *Cold Spring Harb. Symp. Quant. Biol.* 43: 77-90 (1979), which is hereby incorporated by reference. Other *E. coli* replication origins are known to one skilled in the art.

As an alternative to an independent plasmid, the expression sequences may be integrated into the genome of the host microbe. In certain organisms, notably fungi, this is accomplished by homologous recombination between sequences in a plasmid and the host genome. This requires that the heterologous plasmid contain host DNA sequences for mediation of the recombination event. Integration may also be accomplished using selection for a random non-homologous integration event or directed integration via genome editing techniques, including CRISPR-Cas9-directed integration as described by U.S. Pat. No. 8,871,445, which is hereby incorporated by reference in its entirety.

Although optional, inclusion of a selectable marker can speed development of transgenic organisms. One option for a selectable marker is the inclusion of an antibiotic resistance gene in bacteria, for instance: Ampicillin resistance by an expressed beta-lactamase enzyme or tetracycline resistance by an expressed drug efflux pump. Only cells containing the expression construct will survive challenge with the corresponding antibiotic. Examples of additional antibiotics include, but are not limited to, hygromycin, bleomycin, chloramphenicol and phleomycin). Additional antibiotics and corresponding resistance genes are known to one skilled in the art. Due to the ethical concerns of increased antibiotic use, alternative selection methods are preferred. These include the use of auxotrophic organisms. In this case, the microbe can be mutated by the removal of a biosynthetic gene for a required nutrient. Examples are genes associated with tryptophan, uracil, or adenine biosynthesis. The organism can grow on media supplemented with the nutrient, but cannot grow in conditions of a minimal medium that does not contain the nutrient. The expression construct is then modified with an intact copy of the missing biosynthetic gene (e.g. pyr4 complementation of a pyr4 deficient *A. nidulans, A. awamori* or *Trichoderma reesei* and argB complementation of an argB deficient strain). Reference is made to Kelley et al., *EMBO J.* 4: 475-479 (1985); Penttila et al., *Gene* 61:155-164 (1987) and Kinghom et al Applied Molecular Genetics of Filamentous Fungi, Blackie Academic and Professional, Chapman and Hall, London (1992), which are hereby incorporated by reference in their entirety. A final option is to include a toxin/anti-toxin system. Briefly, one gene encodes a long-lived toxin which will cause cell death. The toxin is bound and inactivated by an antitoxin protein. A cell containing a genomic copy of the toxin gene will die unless the cell also expresses the antitoxin protein. In general, the antitoxin protein is more highly-expressed as compared with the toxin protein, but it is also quickly degraded within the cell. The ratA/tpxA toxin system is endogenous to *Bacillus subtilis* as described by Silvaggi et al., "Small Untranslated RNA Antitoxin in *Bacillus subtilis,*" *J Bacteriol.* 187: 6641-6650 (2005), which is incorporated by reference in its entirety, and can control selection of a recombinant plasmid. Another bacterial toxin, GST-ParE, is disclosed in PCT Application Publ. No. WO/2002020750, which is hereby incorporated by reference in its entirety. Many other toxin/antitoxin systems are known in the art, as reviewed by Unterholzner et al., "Toxin-antitoxin systems: Biology, identification, and application," *Mobile Genetic Elements* 3:5, e26219 (2013), which is hereby incorporated by reference in its entirety.

Another optional factor in the design of the expression construct is the choice of secretion signals for the peptide or protein. These signal sequences are added to the bioactive peptide or protein gene sequence and result in a fusion protein with a secretion tag sequence that directs localization of the active peptide through the host microbe's existing secretion machinery.

A library of secretion tags specific for *Bacillus subtilis* is available from Clontech as part of the *Bacillus subtilis* Secretory Protein Expression System; any one of these secretion tags can be used to direct secretion of a recombinant protein or polypeptide in *B. subtilis*.

One suitable secretion signal sequence for *Trichoderma reesei* is the CBH I secretion signal (MYRKLAVISAFLA-TARA, SEQ ID NO: 3) as described by Zhong et al., "Expression and Secretion of the Human Erythropoietin Using an Optimized cbh1 Promoter and the Native CBH I Signal Sequence in the Industrial Fungus *Trichoderma reesei,*" *Appl. Biochem. Biotechnol.* 165:1169-1177 (2011), which is hereby incorporated by reference in its entirety.

Terminator sequences which are recognized by the expression host to terminate transcription may be operably linked to the 3' end of the fusion DNA construct encoding the fusion protein to be expressed. Those of general skill in the art are well aware of various terminator sequences that may be used with filamentous fungi. Non-limiting examples include the terminator from the *Aspergillus nidulans* trpC gene (Yelton M. et al., *Proc. Natl. Acad. Sci. USA* 81: 1470-1474 (1984), which is hereby incorporated by reference in its entirety) and the terminator from the *Aspergillus* niger glucoamylase genes (Nunberg et al., *Mol. Cell. Biol.* 4: 2306-2353 (1984), which is hereby incorporated by reference in its entirety). Likewise, transcriptional terminators for bacteria including *E. coli, Bacillus subtilis*, and others are known in the art. In particular, *Bacillus* terminators for the genes amyE, penP, and bglS have been characterized for efficacy by Hess and Graham, "Efficiency of transcriptional terminators in *Bacillus subtilis*," *Gene* 95:137-41 (1990), which is hereby incorporated by reference in its entirety. Likewise, a bioinformatics approached revealed a large array of transcriptional terminators in *B. subtilis* and related species (de Hoon et al, "Prediction of transcriptional terminators in *Bacillus subtilis* and related species," *PLOS Comput. Biol.* 1:e25 (2005), which is hereby incorporated by reference in its entirety. A similar study in *E. coli* showed the efficacy of the rrnB transcriptional terminator sequence (Lesnik et al., "Prediction of the rho-independent transcriptional terminators in *Escherichia coli*," *Nucleic Acids Research* 29:3583-3594 (2001), which is hereby incorporated by reference in its entirety).

One exemplary DNA construct for expression in *B. subtilis* comprises the PliaG promoter fused with a *B. subtilis* codon-optimized synthetic gene containing the AmyE secretion signal fused N-terminal to the sequence of P15a (as described in U.S. patent application Ser. No. 14/872,298 to Wei et al. which is hereby incorporated by reference in its entirety) and the rho-independent transcriptional terminator from *E. coli* rrnB. Such a construct, further incorporating BamHI and XhoI sites for insertion into a DNA vector, is demonstrated by the DNA molecule of SEQ ID NO: 1 and the sequence annotation in FIG. 1. SEQ ID NO: 1 is reproduced below:

```
GGATCCAAAAATCAGACCAGACAAAAGCGGCAAATGAATAAGCGGAACG

GGGAAGGATTTGCGGTCAAGTCCTTCCCTTCCGCACGTATCAATTCGCAA

GCTTTTCCTTTATAATAGAATGAATGAAAAGGAGGAAACAATCATGTTTG

CAAAAAGATTTAAAACATCACTGCTGCCGCTGTTTGCAGGCTTTCTGCTG

CTGTTTCATCTGGTTCTGGCAGGCCCGGCAGCAGCATCAGCAGAAACAGC

AAATAAATCAAATGAAATTTTGGCACACCGGATTCAACAGTTCAAAATC

CGCAAGATGCATCAAAACCGAATGATTCACAATCAAATATTGCAAAACTG

ATTTCAGCACTGATTATGTCACTGCTGCAAATGTAACCAGGCATCAAATA

AAACGAAAGGCTCAGTCGAAAGACTGGGCCTTTCGTTTTATCTGTTGTTT

GTCGGTGAACGCTCTCGAG
```

One exemplary DNA construct for expression in *Trichoderma reesei* comprises a fusion of the cellobiosehydrolase I (CBH I) promoter with a secretion signal for cbhI, a synthetic codon-optimized P14 sequence (as described in U.S. patent application Ser. No. 14/872,347 to Wei et al., which is hereby incorporated by reference in its entirety) and the cbhI terminator sequence from *Trichoderma reesei*. Such a construct, further incorporating XbaI and EcoRI sites for insertion into a DNA vector, is demonstrated by the DNA molecule of SEQ ID NO: 2 and the sequence annotation in FIG. 2. SEQ ID NO: 2 is reproduced below:

```
TCTAGAGTTGTGAAGTCGGTAATCCCGCTGTATAGTAATACGAGTCGCAT

CTAAATACTCCGAAGCTGCTGCGAACCCGGAGAATCGAGATGTGCTGAA

-continued
AGCTTCTAGCGAGCGGCTAAATTAGCATGAAAGGCTATGAGAAATTCTGG

AGACGGCTTGTTGAATCATGGCGTTCCATTCTTCGACAAGCAAAGCGTTC

CGTCGCAGTAGCAGGCACTCATTCCCGAAAAAACTCGGAGATTCCTAAGT

AGCGATGGAACCGGAATAATATAATAGGCAATACATTGAGTTGCCTCGAC

GGTTGCAATGCAGGGGTACTGAGCTTGGACATAACTGTTCCGTACCCCAC

CTCTTCTCAACCTTTGGCGTTTCCCTGATTCAGCGTACCCGTACAAGTCG

TAATCACTATTAACCCAGACTGACCGGACGTGTTTTGCCCTTCATTTGGA

GAAATAATGTCATTGCGATGTGTAATTTGCCTGCTTGACCGACTGGGGCT

GTTCGAAGCCCGAATGTAGGATTGTTATCCGAACTCTGCTCGTAGAGGCA

TGTTGTGAATCTGTGTCGGGCAGGACACGCCTCGAAGGTTCACGGCAAGG

GAAACCACCGATAGCAGTGTCTAGTAGCAACCTGTAAAGCCGCAATGCAG

CATCACTGGAAAATACAAACCAATGGCTAAAAGTACATAAGTTAATGCCT

AAAGGAGTCATATACCAGCGGCTAATAATTGTACAATCAAGTGGCTAAAC

GTACCGTAATTTGCCAACGGCTTGTGGGGTTGCAGAAGCAACGGCAAAGC

CCCACTTCCCCACGTTTGTTTCTTCACTCAGTCCAATCTCAGCTGGTGAT

CCCCCAATTGGGTCGCTTGTTTGTTCCGGTGAAGTGAAAGAAGACAGAGG

TAAGAATGTCTGACTCGGAGCGTTTTGCATACAACCAAGGGCAGTGATGG

AAGACAGTGAAATGTTGACATTCAAGGAGTATTTAGCCAGGGATGCTTGA

GTGTATCGTGTAAGGAGGTTTGTCTGCCGATACGACGAATACTGTATAGT

CACTTCTGATGAAGTGGTCCATATTGAAATGTAAGTCGGCACTGAACAGG

CAAAAGATTGAGTTGAAACTGCCTAAGATCTCGGGCCCTCGGGCCTTCGG

CCTTTGGGTGTACATGTTTGTGCTCCGGGCAAATGCAAAGTGTGGTAGGA

TCGAACACACTGCTGCCTTTACCAAGCAGCTGAGGGTATGTGATAGGCAA

ATGTTCAGGGGCCACTGCATGGTTTCGAATAGAAAGAGAAGCTTAGCCAA

GAACAATAGCCGATAAAGATAGCCTCATTAAACGGAATGAGCTAGTAGGC

AAAGTCAGCGAATGTGTATATATAAAGGTTCGAGGTCCGTGCCTCCCTCA

TGCTCTCCCCATCTACTCATCAACTCAGATCCTCCAGGAGACTTGTACAC

CATCTTTTGAGGCACAGAAACCCAATAGTCAACCGCGGACTGGCATCATG

TATCGGAAGTTGGCCGTCATCTCGGCCTTCTTGGCCACAGCTCAGGCCGG

CCCCCAGAGCGCCAACAAGACCGGCAACGTCGACGACGCCAACAACCAGG

ACCCCATGCAGGCCCTCATGCAGCTCCTCGAGGACCTCGTCTAAAGCTCC

GTGCGAAAGCCTGACGCACCGGTAGATTCTTGGTGAGCCCGTATCATGAC

GGCGGCGGGAGCTACATGGCCCCGGGTGATTTATTTTTTTTGTATCTACT

TCTGACCCTTTTCAAATATACGGTCAACTCATCTTTCACTGGAGATGCGG

CCTGCTTGGTATTGCGATGTTGTCAGCTTGGCAAATTGTGGCTTTCGAAA

ACACAAAACGATTCCTTAGTAGCCATGCATTTTAAGATAACGGAATAGAA

GAAAGAGGAAATTAAAAAAAAAAAAAAAACAAACATCCCGTTCATAACCC

GTAGAATCGCCGCTCTTCGTGTATCCCAGTACCACGGCAAAGGTATTTCA

TGATCGTTCAATGTTGATATTGTTCCCGCCAGTATGGCTCCACCCCCCAT
```

-continued

```
CTCCGCGAATCTCCTCTTCTCGAACGCGGTGTGGCGCGCCAATTGGTAAT

GACCCCATAGGGAGACAAACAGCATAATAGCAACAGTGGAAATTAGTGGC

GAATTC
```

Introduction of a nucleic acid into a host cell includes techniques such as transformation; electroporation; nuclear microinjection; transduction; transfection, (e.g., lipofection mediated and DEAE-Dextrin mediated transfection); incubation with calcium phosphate DNA precipitate; high velocity bombardment with DNA-coated microprojectiles; and protoplast fusion. General transformation techniques are known in the art (see, e.g., Ausubel et al., (1987), supra, chapter 9; Sambrook (1989) supra; and Campbell et al., *Curr. Genet.* 16:53-56 (1989), which are hereby incorporated by reference in their entirety). Reference is also made to PCT Application Publ. No. WO 05/001036; U.S. Pat. Nos. 6,022,725; 6,103,490; 6,268,328; and published U.S. Application Publ. Nos. 20060041113, 20060040353, 20060040353 and 20050208623, which are incorporated herein by reference in their entirety.

"Transformation" means introducing DNA into a cell so that the DNA is maintained in the cell either as an extrachromosomal element or chromosomal integrant.

The expression of recombinantly introduced proteins in *Trichoderma* is described in U.S. Pat. Nos. 6,022,725; 6,268,328; Harkki et al. *Enzyme Microb. Technol.* 13:227-233 (1991); Harkki et al., *Bio Technol.* 7:596-603 (1989); EP Pat. No. 244,234; EP Pat. No. 215,594; and Nevalainen et al., "The Molecular Biology of *Trichoderma* and its Application to the Expression of Both Homologous and Heterologous Genes," in MOLECULAR INDUSTRIAL MYCOLOGY, Eds. Leong and Berka, Marcel Dekker Inc., NY (1992), pp. 129-148), which are hereby incorporated by reference in their entirety. Reference is also made to Cao et al., *Protein Sci.* 9:991-1001 (2000); Yelton et al., *Proc. Natl. Acad. Sci.* 81:1470-1471 (1984); U.S. Pat. No. 6,590,078; and Berka, et al., in: APPLICATIONS OF ENZYME BIOTECHNOLOGY, Eds. Kelly and Baldwin, Plenum Press, NY (1991), which are hereby incorporated by reference in their entirety, for transformation of *Aspergillus* strains.

In one embodiment, the vector is a *Trichoderma* expression vector related to pTrex3 g, which is described in detail in Example 6 of PCT Application Publ. No. WO 05/001036, which is hereby incorporated by reference in its entirety.

In one embodiment, the preparation of *Trichoderma* sp. for transformation involves the preparation of protoplasts from fungal mycelia. (See Campbell et al., *Curr. Genet.* 16:53-56 (1989), which is hereby incorporated by reference in its entirety). In some embodiments, the mycelia are obtained from germinated vegetative spores. Transformation and protein expression in *Aspergillus* and *Trichoderma* is further described in, for example U.S. Pat. Nos. 5,364,770; 6,022,725; and Nevalainen et al., The Molecular Biology of *Trichoderma* and its Application to the Expression of Both Homologous and Heterologous Genes, in MOLECULAR INDUSTRIAL MYCOLOGY, Eds. Leon and Berka, Marcel Dekker, Inc. (1992) pp. 129-148, which are hereby incorporated by reference in their entirety.

Production of bioactive peptides in *Pseudomonas* is derived from existing work aimed at heterologous protein production under fermentation conditions in *Pseudomonas*, as described by Retallack et al., "Reliable Protein Production in a *Pseudomonas fluorescens* Expression System," *Prot. Exp. Purif.* 81: 157-165 (2012), which is hereby incorporated by reference in its entirety. Notably, many components of *E. coli* expression plasmids are also effective in *Pseudomonas*. Adaptation of such plasmids for use in beneficial microbes may require changing the promoter. In particular, Miksch and Dobrowolski, "Growth Phase-dependent Induction of Stationary-phase Promoters of *Escherichia coli* in Different Gram-negative Bacteria," *J Bacteriol.* 177: 5374-5378 (1995), which is hereby incorporated by reference in its entirety, showed that the *E. coli* stationary phase promoters bolAp 1 and fic are functional in *Acetobacter methanolicus*, *Xanthomonas campestris*, *Pseudomonas putida*, and *Rhizobium meliloti*.

An additional aspect of the invention is the production of bioactive proteins and peptides from fungal sources. For fungal gene expression, a plasmid DNA element can be introduced that integrates into the fungal genome by recombination. U.S. Pat. No. 8,044,192, which is hereby incorporated by reference in its entirety, discloses the Stp1 promoter that is active in *Trichoderma reesei* upon glucose exhaustion. The disclosed plasmid pPGamdS can be adapted for the production of bioactive protein or peptide expression in *Trichoderma*. More recently, the cbhII promoter was successfully developed for protein expression in *Trichoderma* by Meng et al., "Heterologous Protein Expression in *Trichoderma reesei* Using the cbhII Promoter," *Plasmid* 70: 272-276 (2013), which is hereby incorporated by reference in its entirety.

A culture of cells is also provided. The culture of cells may contain a population of the above-described cells, and growth medium. The growth medium may contain glucose as a carbon source. In particular embodiments, glucose may be the sole carbon source of the growth medium. The growth medium may be free of a carbon source that is known to induce activity of cellulase gene expression (see, e.g., Ilmen et al, *Applied and Environmental Microbiology* 63: 1298-1306 (1997), which is hereby incorporated by reference in its entirety). For example, the growth medium may be free of cellulose, lactose, sophorose, cellobiose, and/or other sugar or cellulose-related material that induces cellulase expression. The culture of cells may be at a temperature of about 30° C. (e.g., 27-33° C.), or at a temperature of about 37° C. (e.g., 34-39° C.), for example. In a particular embodiment, the growth medium may contain glucose, glucose and sopohorose, or lactose as a carbon source, and the culture may be grown at 30° C. or 37° C.

As noted above, the transgene expressed by the recombinant beneficial microbe is one that encodes a plant effector protein or polypeptide, which imparts a benefit to a plant grown in the presence of the recombinant beneficial microbe. The benefit imparted by the plant effector protein or polypeptide is distinct of the benefit imparted by recombinant beneficial microbe (i.e., in its naturally occurring, non-recombinant form).

In certain embodiments, the plant effector protein or polypeptide is selected from the group consisting of a hypersensitive response elicitor protein or polypeptide fragment thereof, modified peptides derived from these hypersensitive response elicitor protein or polypeptide fragments, a bacterial flagellin protein or polypeptide, an elongation factor Tu protein or polypeptide, a transglutaminase protein or polypeptide, a fungal elicitor protein or polypeptide, a plant pathogenesis-related (or PR) protein or polypeptide fragment thereof, a plant elicitor protein or polypeptide.

A protein is considered plant bioactive if treatment of any plant tissue with the peptide causes a biochemical signaling cascade within the plant. This can result from, without limit, the specific recognition of a peptide by a receptor embedded in the plant cell membrane, import or translocation of the protein into the plant cell and recognition by a cytoplasmic receptor, or recognition of other physical interactions such as the formation of pore in the plant cell membrane. This signaling cascade may either cause a change in gene expression or the release of signaling molecules from the cell. Changes in gene expression manifest as altered RNA concentrations, detectable by qRT-PCR or microarray experiments. The released signaling molecules can be, without limit, ethylene, jasmonic acid and related metabolites, salicylic acid, gibberellins, auxin, abscisic acid, reactive oxygen species, or potassium and hydronium ions (indicated by a pH change). In some cases, the chemical signaling and gene expression changes may cause an observable change in the appearance of a plant tissue. For example, the hypersensitive response as described by Wei et al., *Science* 257:85-88 (1992), which is hereby incorporated by reference in its entirety, is characterized by coordinated cell death that causes a browning and wilting of the affected tissues.

In certain embodiments, the plant effector protein or polypeptide is a hypersensitive response elicitor polypeptide fragment that induces a hypersensitive response in a plant to which the hypersensitive response elicitor polypeptide fragment is applied.

One representative class of peptides and proteins are the harpins and HR-box family of peptides, as described in U.S. patent application Ser. No. 14/872,298 to Wei et al. (specifically, Tables 1-10 therein), which is hereby incorporated by reference in its entirety. Another exemplary class of peptides is the family of peptides described in the U.S. Provisional Patent Application Ser. No. 62/319,138, filed Apr. 6, 2016, entitled "Hypersensitive Response Elicitor-Derived Peptides and Use Thereof (specifically, HR-eliciting peptides shown in Tables 1, 2, and 4, including without limitation SEQ ID NOS: 8-12, 20, 29, 30, 33, 34, 42-44, 50, 55-57, 71, 72, and 139 as identified therein), which is hereby incorporated by reference in its entirety. These cause a hypersensitive response when infiltrated into tobacco leaves.

Specific families of peptides disclosed in U.S. patent application Ser. No. 14/872,298 to Wei et al., incorporated by reference in the preceding paragraph, include:

(i) SXGISEKXXDXXXXXXXXAXXXP (identified therein as SEQ ID NO: 2 or P4 consensus; SEQ ID NO: 19 herein), wherein
X at position 2 is Q, E, gamma-glutamate ("γ-glutamate"), G, A, or S;
X at position 8 is Q, E, 65 -glutamate, G, A, or S;
X at position 9 is L, A, D, isoaspartic acid ("isoD"), I, V, or F;
X at position 11 is Q, E, γ-glutamate, G, A, or S;
X at position 12 is L, D, isoD, I, or F;
X at position 13 is L, I, V, or F;
X at position 14 is any hydrophilic amino acid, preferably C, S, or T, S or T, or only S;
X at position 15 is Q, E, γ-glutamate, G, A, S, K, or I;
X at position 16 is L, A, I, V, M, or F;
X at position 17 is I, S, or F;
X at position 18 is Q, E, γ-glutamate, G, A, or S;
X at position 20 is L, I, V, or F;
X at position 21 is L or F; and
X at position 22 is Q, E, γ-glutamate, G, A, or S;

(ii) XXGISEKXLDXLLTXLIXALLXX (identified therein as SEQ ID NO: 3 or P1 consensus; SEQ ID NO: 20 herein), wherein
X at position 1 is N, D, isoD, G, A, or S;
X at position 2 is Q, E, γ-glutamate, G, A, or S;
X at position 8 is Q, E, γ-glutamate, G, A, or S;
X at position 11 is Q, E, γ-glutamate, G, A, or S;
X at position 15 is Q, E, γ-glutamate, G, A, or S;
X at position 18 is M, T, K, E, γ-glutamate, G, A, or S;
X at position 22 is Q, E, γ-glutamate, G, A, or S; and
X at position 23 is Q, E, γ-glutamate, G, A, or S;

(iii) (L/M)XXLLXXLLXXLL (identified therein as SEQ ID NO: 25 or P17/18 min consensus; SEQ ID NO: 21 herein), wherein
X at position 2 is A, S, T, G, D, isoD, E, γ-glutamate, Q, N, K, or R;
X at position 3 is Q, A, S, T, G, D, isoD, E, γ-glutamate, N, K, or R;
X at position 6 is A, S, T, G, D, isoD, E, γ-glutamate, Q, N, K, or R;
X at position 7 is Q, A, S, T, G, D, isoD, E, γ-glutamate, N, K, or R;
X at position 10 is K, A, S, T, G, D, isoD, E, γ-glutamate, Q, N, or R; and
X at position 11 is S, A, T, G, D, isoD, E, γ-glutamate, Q, N, K, or R;

(iv) XXXXXXXXXXX(L/M)XXLLXXLLXXLLXXX (SEQ ID NO: 49, P17/18 consensus), wherein
X at position 1 is Q, S, E, γ-glutamate, A, T, G, D, isoD, N, K, or R;
X at position 2 is Q, S, E, γ-glutamate, A, T, G, D, isoD, N, K, or R;
X at position 3 is P, Q, S, E, γ-glutamate, A, T, G, D, isoD, N, K, or R;
X at position 4 is I, Q, S, E, γ-glutamate, A, T, G, D, N, isoD, K, or R;
X at position 5 is D, isoD, S, E, γ-glutamate, A, T, G, N, Q, K, or R;
X at position 6 is R, Q, S, E, γ-glutamate, A, T, G, D, isoD, N, or K;
X of position 7 is Q, S, E, γ-glutamate, A, T, G, D, isoD, N, K, or R;
X at position 8 is T, Q, S, E, γ-glutamate, A, G, D, isoD, N, K, or R;
X at position 9 is I, Q, S, E, γ-glutamate, A, T, G, D, isoD, N, K, or R;
X at position 10 is E, γ-glutamate, Q, S, A, T, G, D, isoD, N, K, or R;
X at position 11 is Q, S, E, 65 -glutamate, A, T, G, D, isoD, N, K, or R;
X at position 13 is A, S, T, G, D, isoD, E, γ-glutamate, Q, N, K, or R;
X at position 14 is Q, A, S, T, G, D, isoD, E, γ-glutamate, N, K, or R;
X at position 17 is A, S, T, G, D, isoD, E, γ-glutamate, Q, N, K, or R;
X at position 18 is Q, A, S, T, G, D, isoD, E, γ-glutamate, N, K, or R;
X at position 21 is K, A, S, T, G, D, isoD, E, γ-glutamate, Q, N, or R;
X at position 22 is S, A, T, G, D, isoD, E, γ-glutamate, Q, N, K, or R;
X at position 25 is S, A, T, G, D, isoD, E, γ-glutamate, Q, N, K, or R;
X at position 26 is P, S, A, T, G, D, isoD, E, γ-glutamate, Q, N, K, or R;
X at position 27 is Q, S, A, T, G, D, isoD, E, γ-glutamate, N, K, or R; and
wherein one or more of amino acids 1 to 11 and/or 25 to 27 is optionally not present (v) XLXX(L/M)LXLIXX(L/I/V/F/M)(L/I/V/F/M) (identified therein as SEQ ID NO: 26 or P19 consensus; SEQ ID NO: 22 herein), wherein
  X at position 1 is optional and can be L, I, V, F, or M;
  X at position 3 is K, A, S, T, G, D, isoD, E, γ-glutamate, Q, N, or R;
  X at position 4 is A, S, T, G, D, isoD, E, γ-glutamate, Q, N, K, or R;
  X at position 7 is K, A, S, T, G, D, isoD, E, γ-glutamate, Q, N, or R;
  X at position 10 is A, S, T, G, D, isoD, E, γ-glutamate, Q, N, K, or R; and
  X at position 11 is R, A, S, T, G, D, isoD, E, γ-glutamate, Q, N, or K.

Specific peptides in Tables 1-10 of U.S. patent application Ser. No. 14/872,298 to Wei et al. include the following peptides:

```
P1-18t (identified as SEQ ID NO: 42)
NQGISEKQLDQLLTQLITALLQQ           (SEQ ID NO: 23)

P4-14s (identified as SEQ ID NO: 6)
SQGISEKQLDQLLSQLIQALLQP           (SEQ ID NO: 24)

P18 (identified as SEQ ID NO: 83
QQPIDRQTIEQMAQLLAQLLKSLL-         (SEQ ID NO: 25)
SPQ P19 (identified as SEQ ID NO: 89)
ITPDGQGGGQIGDNPLLKAMLKLIA         (SEQ ID NO: 26)

P30-3 (identified as SEQ ID NO: 190)
LEELLEELIEELLEE                   (SEQ ID NO: 27)

P30-4 (identified as SEQ ID NO: 210)
LEELLEELIEELL                     (SEQ ID NO: 28).
```

In other embodiments, the plant effector protein or polypeptide is a hypersensitive response elicitor polypeptide fragment that induces an active plant response other than a hypersensitive response when the polypeptide fragment is applied. An exemplary class of peptides is the family of peptides described in patent application Ser. No. 14/872,347 to Wei et al. (specifically, Tables 1-16 therein), which is hereby incorporated by reference in its entirety. Another exemplary class of peptides is the family of peptides described in the U.S. Provisional Patent Application Ser. No. 62/319,138, filed Apr. 6, 2016, entitled "Hypersensitive Response Elicitor-Derived Peptides and Use Thereof (specifically, HR-negative peptides shown in Tables 1, 2, and 4, including without limitation SEQ ID NOS: 13, 15-19, 25-28, 51-53, and 140 as identified therein), which is hereby incorporated by reference in its entirety. Although these do not cause a hypersensitive response, they stimulate the production of hydrogen peroxide and other reactive oxygen species within tobacco or soy leaves.

Specific families of peptides disclosed in U.S. patent application Ser. No. 14/872,347 to Wei et al., incorporated by reference in the preceding paragraph, include those having a truncated HR Box sequence according to: L-X-X-(L/I)-(L/I)-X-X-(L/I/V)-(L/I/V) (identified therein as SEQ ID NO: 116; SEQ ID NO: 29 herein), wherein
  the peptide is less than 50 amino acids in length, and is free of cysteine and methionine;
  each X at positions 2, 3, 6, 7 is independently selected from the group consisting of G, A, S, T, D, isoD, E, g-glutamate, Q, N, K, and R; and
  the peptide induces an active plant response, but does not induce a hypersensitive response, when applied to mechanically disrupted plant tissue.

Specific peptides in Tables 1-16 of U.S. patent application Ser. No. 14/872,347 to Wei et al. include the following peptides:

```
P1-29 (identified as SEQ ID NO: 130)
NQGISEKQLDQLLTQLI                 (SEQ ID NO: 30)

P4-111 (identified as SEQ ID NO: 132)
SQGISEKQLDQLLSQLI                 (SEQ ID NO: 31)

P14 (identified as SEQ ID NO: 113)
QAGPQSANKTGNVDDANN                (SEQ ID NO: 32)
QDPMQALMQLLEDLV P14a (identified as SEQ ID NO: 114)
ANNQDPMQALMQLLEDLV                (SEQ ID NO: 33).
```

Specific families of peptides disclosed in U.S. Provisional Patent Application Ser. No. 62/319,138, incorporated by reference in several paragraphs above, include:
(i) L-X-X-L-L-L-X-(F/L)-(I/L)-X-X-X-L (identified therein as SEQ ID NO: 2; SEQ ID NO: 34 herein) wherein
  X at position 3 is optional and, when present, is selected from D, isoD, E, g-glutamate, Q, N, S, and G, and
  each X at positions 2, 7, 10, 11, and 12 is independently selected from M, A, D, isoD, E, g-glutamate, Q, N, S, and G; or
(ii) (Q/E)-(Q/E)-(L/I/V/F)-X-X-(L/I/V/F)-(L/I/V/F)-(L/I/V/F)-X-(L/I/V/F)-(L/I/V/F)-X-X-X-(L/I/V/F)-(D/G/Q/E)-(D/G/Q/E) (identified therein as SEQ ID NO: 3; SEQ ID NO: 35 herein) wherein
  X at position 5 is optional and, when present, is selected from D, isoD, E, g-glutamate, Q, N, S, and G, and
  each X at positions 4, 9, 12, 13, and 14 is independently selected from M, A, D, isoD, E, g-glutamate, Q, N, S, and G; or
(iii) (L/I/V/F)-X-X-(L/I/V/F)-(L/I/V/F)-(L/I/V/F)-X-(L/I/V/F)-(L/I/V/F)-X-X-X-(L/I/V/F)-(D/G/Q/E)-(D/G/Q/E) (identified therein as SEQ ID NO: 4; SEQ ID NO: 36 herein) wherein
  X at position 3 is optional and, when present, is selected from D, isoD, E, g-glutamate, Q, N, S, and G, and
  each X at positions 2, 7, 10, 11, and 12 is independently selected from M, A, D, isoD, E, g-glutamate, Q, N, S, and G; or
(iv) (Q/E)-(Q/E)-(L/I/V/F)-X-X-(L/I/V/F)-(L/I/V/F)-(L/I/V/F)-X-(L/I/V/F)-(L/I/V/F)-X-X-X-(L/I/V/F), (identified therein as SEQ ID NO: 5; SEQ ID NO: 37 herein) wherein
  X at position 5 is optional and, when present, is selected from D, isoD, E, g-glutamate, Q, N, S, and G, and
  each X at positions 4, 9, 12, 13, and 14 is independently selected from M, A, D, isoD, E, g-glutamate, Q, N, S, and G.

Specific peptides in Tables 1, 2, and 4 of U.S. Provisional Patent Application Ser. No. 62/319,138 include the following peptides:

```
P5 (identified as SEQ ID NO: 8)
SAGSEQQLDLLLMFIMMMLQQ             (SEQ ID NO: 38)

P5a (identified as SEQ ID NO: 9)
SAGSEQQLDQLLLMFIMMMLQQ            (SEQ ID NO: 39)

P5-21 (identified as SEQ ID NO: 33)
SEEQLELLLAFIAAALQQEE              (SEQ ID NO: 40)

P5-25 (identified as SEQ ID NO: 52)
SEEEEQLDQLLLAFIAAALQQ             (SEQ ID NO: 41).
```

Of these peptides, P5, P5a, and P5-21 are capable of inducing a hypersensitive response, whereas P5-25 does not.

Each of U.S. patent application Ser. No. 14/872,298 to Wei et al., U.S. patent application Ser. No. 14/872,347 to Wei et al., and U.S. Provisional Patent Application Ser. No. 62/319,138 also describes the expression of variants of the disclosed peptides, which can be recombinantly produced and then purified. The resulting variants differ from the disclosed peptides by the substitution of individual amino acids at enzymatic cleavage sites, which avoids the possibility of internal peptide cleavage upon exposure to a particular enzyme. One enzymatic cleavage site identified in all three of these applications is a trypsin specific cleavage site, which cleaves after Lys and Arg residues. U.S. patent application Ser. No. 14/872,298 to Wei et al. and U.S. patent application Ser. No. 14/872,347 to Wei et al. both provide an exemplary description of such variants, which involves mutating lysine and arginine residues to glutamate and introducing an arginine residue at the C-terminal end of the peptide. So mutated variants of SEQ ID NOS: 23-26 and 30-32 are shown below as SEQ ID NOS: 42-48

```
K→E P1-18t variant
NQGISEEQLDQLLTQLITALLQQR          (SEQ ID NO: 42)

K→E P4-14s variant
SQGISEEQLDQLLSQLIQALLQPR          (SEQ ID NO: 43)

K/R→E P18 variant
QQPIDEQTIEQMAQLLAQLLESLLSPQR      (SEQ ID NO: 44)

K→E P19 variant
ITPDGQGGQIGDNPLLEAMLELIAR         (SEQ ID NO: 45)

K→E P1-29 variant
NQGISEEQLDQLLTQLIR                (SEQ ID NO: 46)

K→E P4-111 variant
SQGISEEQLDQLLSQLIR                (SEQ ID NO: 47)

K→E P14 variant
QAGPQSANETGNVDDANNQDPMQA          (SEQ ID NO: 48)
LMQLLEDLVR.
```

Peptides that are identified to "consist essentially of" a recited sequence include the recited amino acid sequence(s) optionally with one or more extraneous amino acids at the N- and/or C-terminal ends thereof, which extraneous amino acids do not materially alter one or more of the following properties: (i) the ability of the peptide to induce a hypersensitive response in plants, (ii) solubility of the peptide in water or aqueous solutions, (iii) stability of the peptide dissolved in water or aqueous solution at 50° C. over a period of time (e.g., 3 weeks), and (iv) resistance of the peptide to chemical degradation in the presence of an aqueous buffered solution that includes a biocidal agent (e.g.,Proxel®GXL) at 50° C. over a period of time (e.g., 3 weeks). In certain embodiments, material alteration of the one or more properties is intended to mean that there is less than 20% variation, less than 15% variation, less than 10% variation, or less than 5% variation in a recited property when comparing a peptide possessing the one or more extraneous amino acids to an otherwise identical peptide lacking the one or more extraneous amino acids. In certain embodiments, the number of extraneous amino acids at the N- or C-terminal ends is up to 20 amino acids at one or both ends, up to 15 amino acids at one or both ends, up to 10 amino acids at one or both ends, up to 7 amino acids at one or both ends, up to 5 amino acids at one or both ends, or up to 3 amino acids at one or both ends. Further, to the extent that a recited sequence is in the form of a consensus sequence where one or more of the denoted X or Xaa residues can be any of one or more amino acids, then multiple peptide sequences are embraced by the peptide consisting essentially of such a recited sequence, without regard to additional variations of such sequences that are afforded by the presence of extraneous amino acids at the N- and/or C-terminal ends thereof.

A number of peptides are described in the art as inducing a response in plant cells. Flg22 is a 22-amino acid peptide sequence from the bacterial flagellin protein that causes a response in tomato cells as shown by Felix et al., "Plants Have a Sensitive Perception System For the Most Conserved Domain of Bacterial Flagellin," *Plant J.* 18: 265-76 (1999), which is hereby incorporated by reference in its entirety. Elf18 is a peptide derived from elongation factor Tu that likewise causes an immune response in the cells of *Arabidopsis thaliana*, as shown by Kunze et al., "The N Terminus of Bacterial Elongation Factor Tu Elicits Innate Immunity in *Arabidopsis* Plants," *Plant Cell* 16: 3496-3507 (2004) which is hereby incorporated by reference in its entirety. There are also proteins of fungal origin known to induce a response in plant cells. Pep-13 is a peptide sequence from a transglutaminase protein of the pathogenic *Phytophthora sojae* that causes a response in parsley and potato cells as shown by Brunner et al., "Pep-13, a Plant Defense-inducing Pathogen-associated Pattern From *Phytophthora* Transglutaminases," *EMBO J* 21:6681-6688 (2002), which is hereby incorporated by reference in its entirety. Further, proteins PevD1 from *Verticillium dahliae* and PebC1 from *Botrytis cinerea* induce responses in cotton and *Arabidopsis*, respectively (Bu et al. "A Fungal Protein Elicitor PevD1 Induces *Verticillium* Wilt Resistance in Cotton," *Plant Cell Rep.* 33: 461-470 (2014) and Zhang et al. "Fungal Elicitor Protein PebC1 From *Botrytis cinerea* Improves Disease Resistance in *Arabidopsis thaliana*," *Biotechnolo. Lett.* 36:1069-1078 (2014), which are hereby incorporated by reference in their entirety). A 28-amino acid peptide derived from the Avr9 gene of *Cladosporum fulvum* that causes a response in certain cultivars of tomato, as shown by Van den Ackerveken et al. "The AVR9 Race-specific Elicitor of *Cladosporium flavum* is Processed by Endogenous and Plant Proteases," *Plant Physiol.* 103: 91-96 (1993), which is hereby incorporated by reference in its entirety. Additional pathogen proteins and peptides can also mediate plant defenses that are known to one skilled in the art.

Some plant-derived peptides are capable of inducing plant immune responses. The first of these to be described was Systemin, a small peptide from tomato leaves, described in U.S. Pat. No. 5,378,819, which is hereby incorporated by reference in its entirety. More recently, peptide sequences initially derived from *Arabidopsis* were found to exist in a variety of crop species, as described in U.S. Pat. Nos. 8,686,224 and 9,109,039, which are hereby incorporated by reference in their entirety. Additional members of this family are described by Lori et al. "Evolutionary Divergence of the Plant Elicitor Peptides (Peps) and Their Receptors: Interfamily Incompatibility of Perception but Compatibility of Downstream Signaling" *J Exp. Bot.* 66: 5315-5325 (2015), which is hereby incorporated by reference in its entirety. Additional peptides have also been discovered in soy plants, including GmSubPep, Gmpep914, Gmpep890, as described by Pearce et al., "A Subtilisin-like Protein From Soybean Contains an Embedded, Cryptic Signal That Activates Defense-related Genes," *PNAS* 107:14921-14925 (2010) and Yamaguchi et al., "GmPep914, an Eight-Amino Acid Peptide Isolated From Soybean Leaves, Activates Defense-related Genes," *Plant Physiol.* 156: 932-942 (2011), which are hereby incorporated by reference in their entirety.

The benefits attributable to the use of the recombinant beneficial microbe depend on the type of microbe and the plant effector protein expressed thereby. In certain embodiments, the benefit attributable to the recombinant beneficial microbe is providing nutrients to a plant, producing plant hormone analogs that stimulate growth or reduce stress signaling, or competing with pathogenic organisms. In certain embodiments, the benefit attributable to the plant effector protein or polypeptide is improved disease resistance, growth enhancement, tolerance and resistance to biotic stressors, tolerance to abiotic stress, desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. Multiple different recombinant host cells can be used in combination.

Once engineered microbes are raised, e.g., in a fermentation apparatus, the engineered microbes can be recovered and then provided in either a dry composition or a liquid composition or suspension. Thus, a further aspect of the invention relates to a composition that includes a plurality of recombinant host cells as described above and one or more carriers. The plurality of recombinant host cells can be the same type, e.g., conferring the same benefits to plants grown in their presence, or the plurality of recombinant host cells can include a plurality of distinct recombinant host cells that each confer distinct combinations of benefits to plants grown in their presence.

Colony forming units (c.f.u.) are used to quantify microbes. 1 c.f.u. of a microbe generates a single colony when spread onto a solid nutrient agar compatible with the organism and corresponds to one healthy, replication competent cell. In a dry powder formulation, the concentration of microbes can exceed $5 \times 10^{10}$ cfu/gram of material. Suitable concentrations for a dry formulation include $>10^{11}$, $>5 \times 10^{10} > 10^{10}$, $>10^9$, $>10^8$, $10^7$, or $10^6$ cfu/gram. Likewise, microbes can be provided as a liquid suspension. Suitable concentrations for a liquid formulation include $>10^{10}$, $>10^9$, $>10^8$, $>10^7$, $>10^6$, $>10^5$ cfu/ml.

Suitable carriers include water, aqueous solutions optionally containing one or more co-solvents, slurries, and solid carrier particles. Exemplary solid carriers include mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, and products of vegetable origin, such as cereal meal, tree bark meal, wood meal and nutshell meal, cellulose powders, starches and starch derivatives, as well as other mono-, di-, and poly-saccharides. Exemplary aqueous solutions include those having pH 6-8, more preferably 6.5 to 7.5, containing a buffer matched to this range. Suitable buffers include, without limitation citrate, phosphate, carbonate, and HEPES. However, some microbes can persist in a spore form that is more resilient extremes of heat and pH as well as extended storage. Exemplary aqueous solutions compatible with this spore state include those having pH 3-8, more preferably 4.0-7.5, containing a buffer matched to this range. In addition to buffers described supra, suitable buffers include, without limitation, acetate, glutamate, and aspartate. The solution may optionally be supplemented with an enzymatic digest of proteins, yeast extract, and mineral nutrients, including but not limited to magnesium and iron.

Other suitable additives include buffering agents, wetting agents, coating agents, and abrading agents. These materials can be used to facilitate application of the compositions in accordance with the present invention.

For liquid compositions or suspensions, the microbes can be mixed in water, or a buffer solution, and applied as a spray or soaking treatment to the plant seeds, the plants or the locus where plants are grown. Alternatively, the solution can be applied prior to planting seeds at the locus, after planting seeds at the locus, prior to planting one or more seedlings at the locus, after planting one or more seedlings at the locus, or to the locus while plants are being grown at the locus.

For dry compositions, the microbes can be dried with or without inert carrier particles, and the dry composition can be applied to seeds, the locus where seeds will be planted or plants are being grown, or directly to plants.

As discussed hereinafter, the recombinant beneficial microbes can be used to impart multiple benefits to plants grown in the presence of the recombinant beneficial microbes. These uses involve application of the recombinant beneficial microbes directly to plant seeds, directly onto plants, or indirectly onto plants via application to the locus where seeds will be plants or plants are being grown. In these embodiments, the locus may include artificial or natural soil, a polymer growth medium, or a hydroponic growth medium. The soil can be present in any of a variety of environments including an open field, a partially covered field, a greenhouse, etc.

The present invention further relates to methods of imparting disease resistance to plants, enhancing plant growth, effecting pest control, imparting biotic or abiotic stress tolerance to plants, and/or modulating plant biochemical signaling. According to one embodiment, these methods involve applying an effective amount of recombinant host cell of the invention, or a composition of the invention to a plant or plant seed or the locus where the plant is growing or is expected to grow. As a consequence of such application, the recombinant host cell contacts cells of the plant or plant seed, and induces in the plant or a plant grown from the plant seed disease resistance, growth enhancement, tolerance to biotic stress, tolerance to abiotic stress, or altered biochemical signaling. According to an alternative embodiment, the recombinant host cell or composition of the invention can be applied to plants such that seeds recovered from such plants themselves are able to impart disease resistance in plants, to enhance plant growth, to affect insect control, to impart tolerance to biotic or abiotic stress, and/or to modulate biochemical signaling, to modulate maturation.

In these embodiments, it is also possible to select plants or plant seeds or the locus to which the recombinant host cell or composition of the invention is applied. For example, for fields known to contain a high nematode content, the plants or plant seeds to be grown in such fields, or the fields (locus), can be selectively treated by applying the recombinant host cell or composition of the invention as described herein; whereas no such treatment may be necessary for plants or plant seeds grown in fields containing low nematode content. Similarly, for fields having reduced irrigation, the plants or plant seeds to be grown in such fields, or the fields (locus), can be selectively treated by applying the recombinant host cell or composition of the invention as described herein; whereas no such treatment may be necessary for plants or plant seeds grown in fields having adequate irrigation. Likewise, for fields prone to flooding, the plants or plant seeds to be grown in such fields, or the fields (locus), can be selectively treated by applying the recombinant host cell or composition of the invention as described herein; whereas no such treatment may be necessary for plants or plant seeds grown in fields that are not prone to flooding. As yet another example of such selection, for fields prone to insect attack at certain times of the growing season, the plants or plant seeds to be grown in such fields, or the fields (locus), can be selectively treated by applying the recombinant host cell or composition of the invention as described herein; whereas the same field may not be treated at ineffective times of the growing season or other fields that are not prone to such attack may go untreated. Such selection steps can be carried out when practicing each of the methods of use described herein, i.e., imparting disease resistance to plants, enhancing plant growth, effecting pest control (including insects and nematodes), imparting biotic or abiotic stress tolerance to plants, and/or modulating plant biochemical signaling.

The present invention further relates to methods of improving desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. These methods involve applying an effective amount of recombinant host cell of the present invention or a composition according to the present invention to a plant or the locus where the plant is growing. As a consequence of such application, the recombinant host cell contacts cells of the plant or plant seed, and induces desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants. Alternatively, an effective amount of recombinant host cell of the present invention or a composition according to the present invention can be applied to a harvested fruit or vegetable. As a consequence of such application, the recombinant host cell contacts cells of the harvested fruit or vegetable, and induces post-harvest disease resistance or desiccation resistance to the treated fruit or vegetables, and/or improved longevity of fruit or vegetable ripeness for the treated fruit or vegetables.

In these embodiments, it is also possible to select plants, cuttings, fruits, vegetables, or the locus to which the recombinant host cell or composition of the invention is applied. For example, for harvested cuttings or fruit or vegetables that are being shipped great distances or stored for long periods of time, then these can be selectively treated by applying the recombinant host cell or composition of the invention as described herein; whereas harvested cuttings or fruit or vegetables that are being shipped locally and intended to be consumed without substantially periods of storage can be excluded from such treatment.

Suitable plants that can be treated in accordance with the present invention include dicots and monocots, including agricultural, silvicultural, ornamental and horticultural plants, whether in a natural or genetically modified form. Exemplary plants include, without limitation, alfalfa, apple, apricot, asparagus, avocados, bananas, barley, beans, beech (*Fagus* spec.), begonia, birch, blackberry, blueberry, cabbage, camphor, canola, carrot, castor oil plant, cherry, cinnamon, citrus, cocoa bean, coffee, corn, cotton, cucumber, cucurbit, eucalyptus, fir, flax, fodder beet, fuchsia, garlic, geranium, grapes, ground nut, hemp, hop, juneberry, juncea (*Brassica juncea*), jute, lentil, lettuce, linseed, melon, mustard, nectarine, oak, oats, oil palm, oil-seed rape, olive, onion, paprika, pea, peach, pear, pelargonium, peppers, petunia, pine (*Pinus* spec.), plum, poplar (*Populus* spec.), pome fruit, potato, rape, raspberry, rice, rubber tree, rye, sorghum, soybean, spinach, spruce, squash, strawberry, sugar beet, sugar cane, sunflower, tea, teak, tobacco, tomato, triticale, turf, watermelon, wheat and willow (*Salix* spec.), *Arabidopsis thaliana*, Saintpaulia, poinsettia, chrysanthemum, carnation, and zinnia.

With respect to modified biochemical signaling, this includes both enhancement of certain plant biochemical pathways and diminishment of certain other plant biochemical pathways. Biochemical signaling pathways that can be altered in accordance with the present invention include gene expression and protein production, production of metabolites, and production of signaling molecules/secondary metabolites. Exemplary biochemical signaling pathways and their modifications include, without limitation, induction of nitric oxide production, peroxide production, and other secondary metabolites; agonist of the ethylene signaling pathway and induction of ethylene-responsive gene expression (see Dong et al., *Plant Phys.* 136:3628-3638 (2004); Li et al., *Planta* 239:831-46 (2014); Chang et al., *PLoS One* 10, e0125498 (2015), each of which is hereby incorporated by reference in its entirety); agonist of the salicylic acid signaling pathway and induction of salicylic acid-responsive gene expression (see Dong et al., *Plant J.* 20:207-215 (1999), which is hereby incorporated by reference in its entirety); agonist of the abscisic acid pathway and induction of abscisic acid-responsive gene expression (see Dong et al., *Planta* 221: 313-327 (2005), which is hereby incorporated by reference in its entirety); agonist of the gibberellin signaling pathway and induction of gibberellin-responsive gene expression (see Li et al., *Planta* 239:831-46 (2014), which is hereby incorporated by reference in its entirety); antagonist of jasmonic acid signaling and inhibiting expression of jasmonic acid-responsive genes (see Dong et al., *Plant Phys.* 136:3628-3638 (2004), which is hereby incorporated by reference in its entirety); inducing protease inhibitor expression (see Laluk and Mengiste, *Plant J.* 68:480-494 (2011); Xia et al., *Chin. Sci. Bull* 56: 2351-2358 (2011), each of which is hereby incorporated by reference in its entirety); inducing reactive oxygen species production in plant tissues; inducing immune-related and antimicrobial peptide production, such as, without limitation, peroxidase, superoxide dismutase, chitinase, and β-1,3-glucanase (Wang et al., *J. Agric. Food Chem.* 59:12527-12533 (2011), which is hereby incorporated by reference in its entirety); and inducing expansin gene expression and production (see Li et al., *Planta* 239:831-46 (2014), which is hereby incorporated by reference in its entirety).

With respect to disease resistance, absolute immunity against infection may not be conferred, but the severity of the disease is reduced and symptom development is delayed. Lesion number, lesion size, and extent of sporulation of fungal pathogens are all decreased. This method of imparting disease resistance has the potential for treating previously untreatable diseases, treating diseases systemically which might not be treated separately due to cost, and avoiding the use of infectious agents or environmentally harmful materials.

The method of imparting pathogen resistance to plants in accordance with the present invention is useful in imparting resistance to a wide variety of pathogens including viruses, bacteria, and fungi. Resistance, inter alia, to the following viruses can be achieved by the method of the present invention: Tobacco mosaic virus and Tomato mosaic virus. Resistance, inter alia, to the following bacteria can also be imparted to plants in accordance with present invention:

pathogenic *Pseudomonas* spp., pathogenic *Erwinia* spp., pathogenic *Xanthomonas* spp., and pathogenic *Ralstonia* spp. Plants can be made resistant, inter alia, to the following fungi by use of the method of the present invention: *Fusarium* spp. and *Phytophthora* spp.

With regard to the use of the recombinant host cell or compositions of the present invention to enhance plant growth, various forms of plant growth enhancement or promotion can be achieved. This can occur as early as when plant growth begins from seeds or later in the life of a plant. For example, plant growth according to the present invention encompasses greater yield, increased plant vigor, increased vigor of seedlings (i.e., post-germination), increased plant weight, increased biomass, increased number of flowers per plant, higher grain and/or fruit yield, increased quantity of seeds produced, increased percentage of seeds germinated, increased speed of germination, increased plant size, decreased plant height (for wheat), greater biomass, more and bigger fruit, earlier fruit coloration, earlier bud, fruit and plant maturation, more tillers or side shoots, larger leaves, delayed leaf senescence, increased shoot growth, increased root growth, altered root/shoot allocation, increased protein content, increased oil content, increased carbohydrate content, increased pigment content, increased chlorophyll content, increased total photosynthesis, increased photosynthesis efficiency, reduced respiration (lower $O_2$ usage), compensation for yield-reducing treatments, increased durability of stems (and resistance to stem lodging), increased durability of roots (and resistance to root lodging), better plant growth in low light conditions, and combinations thereof. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

With regard to the use of the recombinant host cell or compositions of the present invention to control pests (including but not limited to insects and nematodes, which are biotic stressors), such pest control encompasses preventing pests from contacting plants to which the recombinant host cell or composition of the invention has been applied, preventing direct damage to plants by feeding injury, causing pests to depart from such plants, killing pests proximate to such plants, interfering with insect larval feeding on such plants, preventing pests from colonizing host plants, preventing colonizing insects from releasing phytotoxins, interfering with egg deposition on host plants, etc. The present invention also prevents subsequent disease damage to plants resulting from pest infection.

The present invention is effective against a wide variety of insects (biotic stressors). European corn borer is a major pest of corn (dent and sweet corn) but also feeds on over 200 plant species including green, wax, and lima beans and edible soybeans, peppers, potato, and tomato plus many weed species. Additional insect larval feeding pests which damage a wide variety of vegetable crops include the following: beet armyworm, cabbage looper, corn ear worm, fall armyworm, diamondback moth, cabbage root maggot, onion maggot, seed corn maggot, pickleworm (melonworm), pepper maggot, and tomato pinworm. Collectively, this group of insect pests represents the most economically important group of pests for vegetable production worldwide. The present invention is also effective against nematodes, another class of economically important biotic stressors. Soybean Cyst Nematode (*Heterodera glycines*) is a major pest of soybeans. Reniform Nematode (*Rotylenchulus reniformis*) is a major pest of cotton as can parasitize additional crop species, notably soy and corn. Additional nematode pests include the root knot nematodes of the genus *Meloidogyne* (particularly in cotton, wheat, and barley), cereal cyst nematodes of the genus *Heterodera* (particularly in soy, wheat, and barley), root lesion nematodes of the genus *Pratylenchus*, seed gall nematodes of the genus *Anguina* (particularly in wheat, barley, and rye), and stem nematodes of the genus *Ditylenchus*. Other biotic stressors include arachnids, weeds, and combinations thereof.

With regard to the use of the recombinant host cells or compositions of the present invention to impart abiotic stress resistance to plants, such abiotic stress encompasses any environmental factor having an adverse effect on plant physiology and development. Examples of such environmental stress include climate-related stress (e.g., drought, flood, frost, cold temperature, high temperature, excessive light, and insufficient light), air pollution stress (e.g., carbon dioxide, carbon monoxide, sulfur dioxide, $NO_x$, hydrocarbons, ozone, ultraviolet radiation, acidic rain), chemical (e.g., insecticides, fungicides, herbicides, heavy metals), nutritional stress (e.g., over- or under-abundance of fertilizer, micronutrients, macronutrients, particularly potassium, nitrogen derivatives, and phosphorus derivatives), and improved healing response to wounding. Use of recombinant host cells of the present invention imparts resistance to plants against such forms of environmental stress.

The methods of the present invention involving application of the recombinant host cell or composition can be carried out through a variety of procedures when all or part of the plant is treated, including leaves, stems, roots, propagules (e.g., cuttings), fruit, etc. Recombinant host cells can be applied in the form of an aqueous solution comprising a suspension of such beneficial microbes, which is then applied to the plant by spraying, coating, or immersion as described above. When treating plant seeds, in accordance with the application embodiment of the present invention, the microbes can be applied by low pressure spraying, coating, immersion (e.g., soaking), or injection. Other suitable application procedures can be envisioned by those skilled in the art provided they are able to effect contact of the beneficial microbes with cells of the plant or plant seed. In accordance with the application embodiment of the present invention, the beneficial microbes can be applied to plants or plant seeds in dry form. By way of example, dry application of microbes can be accomplished using bacterial or fungal products such as Kodiak® HB, available from Chemtura, and T-22™ HC, available from BioWorks. Once treated with the microbes of the present invention, the seeds can be planted in natural or artificial soil and cultivated using conventional procedures to produce plants. After plants have been propagated from seeds treated in accordance with the present invention, the plants may be treated with one or more applications of the microbes of the invention or compositions of the invention, to impart disease resistance to plants, to enhance plant growth, to control insects on the plants, to impart biotic or abiotic stress tolerance, to improve desiccation resistance of removed cuttings, to impart postharvest disease resistance or desiccation resistance to harvested fruit or vegetables, and/or improved longevity of fruit or vegetable ripeness for harvested fruit or vegetables.

The recombinant host cells or compositions of the invention can be applied to plants or plant seeds in accordance with the present invention alone or in a mixture with other materials. Alternatively, the recombinant host cells or compositions can be applied separately to plants with other materials being applied at different times.

EXAMPLES

The following examples are provided to illustrate embodiments of the present invention but are by no means intended to limit its scope.

Example 1—Design of Peptide Expression Plasmids

Briefly, protein expression constructs were made incorporating one of the following harpin peptides: P5-21 (SEEQLELLLAFIAAALQQEE (SEQ ID NO: 4), which is also described in U.S. Provisional Patent Application Ser. No. 62/319,138 as SEQ ID NO: 33), P4-111 (SQ-GISEKQLDQLLSQLI (SEQ ID NO: 5), which is also described in U.S. patent application Ser. No. 15/244,919 as SEQ ID NO: 132), or P30-3 (LEELLEELIEELLEE (SEQ ID NO: 6), which is also described in U.S. patent application Ser. No. 14/872,298 as SEQ ID NO: 190). The expression construct further contained a fluorescent protein fusion for easy detection and increased stability in live cells along with a polyhistidine tag for easy purification. These expression constructs are identified in Table 1 below.

Red fluorescent protein sequences Fresno and Yukon were obtained from ATUM (Newark, Calif., USA). The pBE-S *Bacillus subtilis* expression plasmid was obtained from Clontech/Takara Bio USA (Mountain View, Calif., USA). The sequence of the pBE-S plasmid and the associated user manual are published at the following address: www.clontech.com/US/Products/Protein_Expression_and_Purification/Bacterial_Expression_Systems/High_Yield_Expression/B_subtilis_Secretory_Protein. These are hereby incorporated by reference.

The sequences for the above peptides were added to the C-terminus of the fluorescent protein sequence and were reverse-transcribed using a *Bacillus subtilis* codon bias table from the following address: www.kazusa.or.jp/codon/cgi-bin/showcodon.cgi?species=1423. These sequences were prepared for insertion into the *Bacillus subtilis* expression vector pBE-S by adding context sequence from the plasmid. This includes: 30 base pairs of plasmid sequence upstream of the MluI cleavage site in the pBE-S MCS and 30 base pairs of plasmid sequence downstream of the XbaI cleavage site. These DNA sequences were synthesized commercially as dsDNA, shown as SEQ ID NOs: 7-12 below.

The nucleic acid sequence of Fresno-P30-3 (SEQ ID NO: 7) is as follows:

TAAGTCTACTCTGAACTTAAGCAAAAGGAGAGGGACGCGTATGAATTCAC

TGATTAAAGAAAATATGCATATGAAACTGTATATGGAAGGCACAGTTAAT

AATCATCATTTTAAATGCACATCAGAAGGCGAAGGCAAACCGTATGAAGG

CACACAAACAATGAGAATTAAAGTTGTTGAAGGCGGCCCGCTGCCGTTTG

CATTTGATATTCTGGCAACATCATTTATGTATGGCTCAAGAACATTTATT

AAATATCCGAAAGGCATTCCGGATTTTTTTAAACAATCATTTCCGGAAGG

CTTTACATGGGAAAGAGTTACAAGATATGAAGATGGCGGCGTTGTTACAG

CAACACAAGATACATCACTGGAAGATGGCTGCCTGGTTTATCATGTTCAA

GTTAGAGGCGTTAATTTTCCGTCAAATGGCCCGGTTATGCAAAAAAAAAC

ACTGGGCTGGGAACCGAATACAGAAATGCTGTATCCGGCAGATGGCGGCC

TGGAAGGCAGATCAGATATGGCACTGAAACTGGTTGGCGGCGGCCATCTG

TCATGCTCATTTGTTACAACATATAGATCAAAAAAAACAGTTGGCAATAT

TAAAATGCCGGGCATTCATGCAGTTGATCATAGACTGGTTAGAATTAAAG

AAGCAGATAAAGAAACATATGTTGAACAACATGAAGTTGCAGTTGCAAAA

TTTGCAGGCCTGGGCGGCGGCATGGATGAACTGTATAAATTAGAGGAACT

GCTTGAAGAATTAATTGAAGAATTGCTCGAAGAGTCTAGACATCACCATC

ATCACCACTAATGCGGTAGTTTAT

The nucleic acid sequence of Yukon-P30-3 (SEQ ID NO: 8) is as follows:

TAAGTCTACTCTGAACTTAAGCAAAAGGAGAGGGACGCGTATGTCTCTTT

CCAAGCAGGTCCTTCCGCGTGATGTTCGTATGAGATTTCATATGGATGGG

TGTGTTAATGGACATCAATTTACTATTGAAGGTGAAGGTGCTGGGAAACC

GTATGAAGGTAAAAAAACATTGAAACTGAGAGTGACAAAAGGTGGGCCTC

TTCCCTTCGCCTTCGATATACTTTCAGCAACATTTACGTATGGCAATCGG

TGCTTTTGTGATTACCCGGAAGATATGCCGGACTATTTCAAACAAAGTTT

GCCGGAGGGATACTCATGGGAACGAACGCTGATGTTTGAGGATGGGGGTT

GCGGCACAGCGTCCGCGCACATTTCGTTAGAGAAAGACTGTTTCATTCAC

AACAGCACTTTTCATGGGGTAAATTTCCCAGCAAACGGACCTGTAATGCA

GAAAAAAACACTGAATTGGGAACCTTCATCCGAGCTGATTACGGCTTGTG

ATGGCATCCTGAAGGGGGATGTCACAATGTTTTTACTGCTTGAGGGCGGA

CACCGATTAAAGTGTCAATTCACAACGTCCTATAAGGCCCATAAGGCAGT

GAAAATGCCGCCGAATCATATTATTGAACATGTGCTGGTAAAAAAGAGG

TCGCCGACGGTTTCCAGATTCAGGAACATGCCGTCGCAAAACATTTTACC

GTGGATGTCAAGGAAACATTAGAGGAACTGCTTGAAGAATTATTGAAGAA

TTGCTCGAAGAGTCTAGACATCACCATCATCACCACTAATGCGGTAGTTT

AT

The nucleic acid sequence of Fresno-P4-111 (SEQ ID NO: 9) is as follows:

TAAGTCTACTCTGAACTTAAGCAAAAGGAGAGGGACGCGTATGAATTCAC

TGATTAAAGAAAATATGCATATGAAACTGTATATGGAAGGCACAGTTAAT

AATCATCATTTTAAATGCACATCAGAAGGCGAAGGCAAACCGTATGAAGG

CACACAAACAATGAGAATTAAAGTTGTTGAAGGCGGCCCGCTGCCGTTTG

CATTTGATATTCTGGCAACATCATTTATGTATGGCTCAAGAACATTTATT

AAATATCCGAAAGGCATTCCGGATTTTTTTAAACAATCATTTCCGGAAGG

CTTTACATGGGAAAGAGTTACAAGATATGAAGATGGCGGCGTTGTTACAG

CAACACAAGATACATCACTGGAAGATGGCTGCCTGGTTTATCATGTTCAA

GTTAGAGGCGTTAATTTTCCGTCAAATGGCCCGGTTATGCAAAAAAAAAC

ACTGGGCTGGGAACCGAATACAGAAATGCTGTATCCGGCAGATGGCGGCC

-continued

TGGAAGGCAGATCAGATATGGCACTGAAACTGGTTGGCGGCGGCCATCTG

TCATGCTCATTTGTTACACATATAGATCAAAAAAAAACAGTTGGCAATAT

TAAAATGCCGGGCATTCATGCAGTTGATCATAGACTGGTTAGAATTAAAG

AAGCAGATAAAGAAACATATGTTGAACAACATGAAGTTGCAGTTGCAAAA

TTTGCAGGCCTGGGCGGCGGCATGGATGAACTGTATAAATCGCAAGGAAT

TAGTGAGAAACAGCTAGATCAACTATTATCTCAGCTCATATCTAGACATC

ACCATCATCACCACTAATGCGGTAGTTTAT

The nucleic acid sequence of Yukon-P4-111 (SEQ ID NO: 10) is as follows:

TAAGTCTACTCTGAACTTAAGCAAAAGGAGAGGGACGCGTATGTCACTGT

CAAAACAAGTTCTGCCGAGAGATGTTAGAATGAGATTTCATATGGATGGC

TGCGTTAATGGCCATCAATTTACAATTGAAGGCGAAGGCGCAGGCAAACC

GTATGAAGGCAAAAAAACACTGAAACTGAGAGTTACAAAAGGCGGCCCGC

TGCCGTTTGCATTTGATATTCTGTCAGCAACATTTACATATGGCAATAGA

TGCTTTTGCGATTATCCGGAAGATATGCCGGATTATTTTAAACAATCACT

GCCGGAAGGCTATTCATGGGAAAGAACACTGATGTTTGAAGATGGCGGCT

GCGGCACAGCATCAGCACATATTTCACTGGAAAAAGATTGCTTTATTCAT

AATTCAACATTTCATGGCGTTAATTTTCCGGCAAATGGCCCGGTTATGCA

AAAAAAAACACTGAATTGGGAACCGTCATCAGAACTGATTACAGCATGCG

ATGGCATTCTGAAAGGCGATGTTACAATGTTTCTGCTGCTGGAAGGCGGC

CATAGACTGAAATGCCAATTTACAACATCATATAAAGCACATAAAGCAGT

TAAAATGCCGCCGAATCATATTATTGAACATGTTCTGGTTAAAAAAGAAG

TTGCAGATGGCTTTCAAATTCAAGAACATGCAGTTGCAAAACATTTTACA

GTTGATGTTAAAGAAACATCGCAAGGAATTAGTGAGAAACAGCTAGATCA

ACTATTATCTCAGCTCATATCTAGACATCACCATCATCACCACTAATGCG

GTAGTTTAT

The nucleic acid sequence of Fresno P5-21 (SEQ ID NO: 11) is as follows:

TAAGTCTACTCTGAACTTAAGCAAAAGGAGAGGGACGCGTATGAATAGTC

TTATCAAAGAGAACATGCATATGAAACTGTATATGGAAGGGACAGTGAAT

AACCATCACTTCAAGTGTACCTCTGAAGGAGAAGGGAAACCGTATGAAGG

CACGCAAACGATGCGCATTAAAGTCGTTGAAGGCGGACCCTTACCATTTG

CCTTTGACATTCTGGCAACGAGCTTTATGTATGGAAGCCGGACTTTTATT

AAATACCCAAAAGGCATTCCAGATTTCTTTAAACAAAGCTTCCCAGAAGG

GTTTACATGGGAACGGGTCACAAGATATGAAGACGGCGGAGTCGTGACGG

CAACACAAGATACGAGTCTGGAAGATGGCTGCTTGGTATATCATGTACAA

GTCAGAGGAGTAAACTTTCCGTCTAACGGCCCGGTAATGCAGAAAAAGAC

TTTAGGGTGGGAACCGAATACGGAGATGCTTTATCCTGCAGATGGGGCT

TAGAAGGACGCTCAGACATGGCCGTTAAAATTGGTCGGCGGCGGCCATCTT

-continued

TCCTGTTCTTTCGTGACCACCTATCGATCTAAGAAAACTGTGGGTAACAT

CAAAATGCCAGGGATCCACGCTGTCGATCATCGTTTAGTAAGAATCAAAG

AAGCGGACAAAGAAACGTACGTCGAACAGCATGAAGTGGCAGTTGCTAAA

TTTGCAGGTTTAGGAGGCGGTATGGATGAGTTGTACAAGTCAGAGGAACA

ACTTGAACTGTTATTAGCATTTATCGCAGCCGCCCTTCAACAAGAAGAAT

CTAGACATCACCATCATCACCACTAATGCGGTAGTTTAT

The nucleic acid sequence of Yukon-P5-21 (SEQ ID NO: 12) is as follows:

TAAGTCTACTCTGAACTTAAGCAAAAGGAGAGGGACGCGTATGTCTCTTT

CCAAGCAGGTCCTTCCGCGTGATGTTCGTATGAGATTTCATATGGATGGG

TGTGTTAATGGACATCAATTTACTATTGAAGGTGAAGGTGCTGGGAAACC

GTATGAAGGTAAAAAAACATTGAAACTGAGAGTGACAAAAGGTGGGCCTC

TTCCCTTCGCCTTCGATATACTTTCAGCAACATTTACGTATGGCAATCGG

TGCTTTTGTGATTACCCGGAAGATATGCCGGACTATTTCAAACAAAGTTT

GCCGGAGGGATACTCATGGGAACGAACGCTGATGTTTGAGGATGGGGTT

GCGGCACAGCGTCCGCGCACATTTCGTTAGAGAAAGACTGTTTCATTCAC

AACAGCACTTTTCATGGGGTAAATTTCCCAGCAAACGGACCTGTAATGCA

GAAAAAAACACTGAATTGGGAACCTTCATCCGAGCTGATTACGGCTTGTG

ATGGCATCCTGAAGGGGGATGTCACAATGTTTTTACTGCTTGAGGGCGGA

CACCGATTAAAGTGTCAATTCACAACGTCCTATAAGGCCCATAAGGCAGT

GAAAATGCCGCCGAATCATATTATTGAACATGTGCTGGTAAAAAAGAGG

TCGCCGACGGTTTCCAGATTCAGGAACATGCCGTCGCAAAACATTTTACC

GTGGATGTCAAGGAAACATCAGAGGAACAACTTGAACTGTTATTAGCATT

TATCGCAGCCGCCCTTCAACAAGAAGAATCTAGACATCACCATCATCACC

ACTAATGCGGTAGTTTAT

Example 2—Assembly of Expression Plasmids pBE-S plasmid DNA was double-digested using the restriction enzymes MluI and XbaI (from New England Biolabs, Ipswitch, Mass., USA) according to manufacturer instructions and purified on PCR cleanup columns (Qiagen USA, Germantown, Md., USA). The synthesized dsDNA inserts were inserted into the cut pBE-S plasmid using the Gibson Assembly Hifi 1-Step Kit (Synthetic Genomics, La Jolla, Calif., USA) according to manufacturer instructions. The resulting plasmid DNA libraries were transformed into DH5alpha *E. coli* cells and plated on LB agar supplemented with 100 ug/ml carbenicillin. Select colonies were grown in 10 ml LB broth with 100 ug/ml carbenecillin and plasmid DNA collected by Mini-Prep (Qiagen). The fidelity of the cloning was verified by sequencing of the insert. Satisfactory clones were obtained for all plasmids except Fresno-p30-3. The coding sequence for each of these included: the fluorescent marker protein with the bioactive peptide and a 6×His tag at the C-terminal end. Protein sequences are listed as SEQ ID NOs: 13-18 in Table 1 below

TABLE 1

| Construct Name | Sequence | SEQ ID NO: |
|---|---|---|
| Fresno-P5-21 | MNSLIKENMHMKLYMEGTVNNHHFKCTSEGEGKPYEGTQTMRIKV VEGGPLPFAFDILATSFMYGSRTFIKYPKGIPDFFKQSFPEGFTW ERVTRYEDGGVVTATQDTSLEDGCLVYHVQVRGVNFPSNGPVMQK KTLGWEPNTEMLYPADGGLEGRSDMALKLVGGGHLSCSFVTTYRS KKTVGNIKMPGIHAVDHRLVRIKEADKETYVEQHEVAVAKFAGLG GGMDELYKSEEQLELLLAFIAAALQQEESRHHHHHH | 13 |
| Yukon-P5-21 | MSLSKQVLPRDVRMRFHMDGCVNGHQFTIEGEGAGKPYEGKKTLK LRVTKGGPLPFAFDILSATFTYGNRCFCDYPEDMPDYFKQSLPEG YSWERTLMFEDGGCGTASAHISLEKDCFIHNSTFHGVNFPANGPV MQKKTLNWEPSSELITACDGILKGDVTMFLLLEGGHRLKCQFTTS YKAHKAVKMPPNHIIEHVLVKKEVADGFQIQEHAVAKHFTVDVKE TSEEQLELLLAFIAAALQQEESRHHHHHH | 14 |
| Fresno-P4-111 | MNSLIKENMHMKLYMEGTVNNHHFKCTSEGEGKPYEGTQTMRIKV VEGGPLPFAFDILATSFMYGSRTFIKYPKGIPDFFKQSFPEGFTW ERVTRYEDGGVVTATQDTSLEDGCLVYHVQVRGVNFPSNGPVMQK KTLGWEPNTEMLYPADGGLEGRSDMALKVGGGHLSCSFVTTYRSK KTVGNIKMPGIHAVDHRLVRIKEADKETYVEQHEVAVAKFAGLGG GMDELYKSQGISEKQLDQLLSQLISRHHHHHH | 15 |
| Yukon-P4-111 | MSLSKQVLPRDVRMRFHMDGCVNGHQFTIEGEGAGKPYEGKKTLK LRVTKGGPLPFAFDILSATFTYGNRCFCDYPEDMPDYFKQSLPEG YSWERTLMFEDGGCGTASAHISLEKDCFIHNSTFHGVNFPANGPV MQKKTLNWEPSSELITACDGILKGDVTMFLLLEGGHRLKCQFTTS YKAHKAVKMPPNHIIEHVLVKKEVADGFQIQEHAVAKHFTVDVKE TSQGISEKQLDQLLSQLISRHHHHHH | 16 |
| Fresno-P30-3 | MNSLIKENMHMKLYMEGTVNNHHFKCTSEGEGKPYEGTQTMRIKV VEGGPLPFAFDILATSFMYGSRTFIKYPKGIPDFFKQSFPEGFTW ERVTRYEDGGVVTATQDTSLEDGCLVYHVQVRGVNFPSNGPVMQK KTLGWEPNTEMLYPADGGLEGRSDMALKLVGGGHLSCSFVTTYRS KKTVGNIKMPGIHAVDHRLVRIKEADKETYVEQHEVAVAKFAGLG GGMDELYKLEELLEELIEELLEESRHHHHHH | 17 |
| Yukon-P30-3 | MSLSKQVLPRDVRMRFHMDGCVNGHQFTIEGEGAGKPYEGKKTLK LRVTKGGPLPFAFDILSATFTYGNRCFCDYPEDMPDYFKQSLPEG YSWERTLMFEDGGCGTASAHISLEKDCFIHNSTFHGVNFPANGPV MQKKTLNWEPSSELITACDGILKGDVTMFLLLEGGHRLKCQFTTS YKAHKAVKMPPNHIIEHVLVKKEVADGFQIQEHAVAKHFTVDVKE TLEELLEELIEELLEESRHHHHHH | 18 |

Example 3—Expression of Fluorescent Transgene

Plasmid DNA for Fresno-p4-111, Yukon-p4-111, Fresno-p5-21, Yukon-p5-21, and Yukon p30-3 were transformed into Bacillus subtilis strain RIK1275 as described by the manufacturer of the plasmid and plated on LB plates supplemented with 10 ug/ml Kanamycin. Colonies from this plate were tested for visual evidence of fluorescence using a green laser light source (~532 nm) and an amber-colored filter. Fluorescent colonies were observed for Yukon-p4-111, Fresno-p5-21, Yukon-p5-21, and Yukon p30-3, indicating the production of the protein insert in the Bacillus subtilis cells.

Example 4—Confirmation of Soluble Protein in Bacterial Cell Lysates

Fluorescent colonies from Example 3 were inoculated into 5 ml cultures of LB medium supplemented with 10 ug/ml Kanamycin and grown for 2 days with 170 rpm shaking at 37° C. Cells were harvested by centrifugation (5000 g for 15 minutes at 4° C.). The culture was decanted away from the cell pellet. The cell pellets were resuspended in 1 ml each of Bugbuster Protein Extraction Reagent (EMD Millipore, Billerica, Mass., USA) supplemented with 200 ug/ml of lysozyme. Lysis was allowed to proceed for 20 minutes at room temperature (20° C.). The lysates were centrifuged at 20,000 g for 10 minutes at 4° C. to separate soluble from insoluble proteins. A reddish supernatant was observed for Fresno-p5-21, suggesting that the recombinant protein was soluble and well-expressed. For the other samples, no color was observed in the supernatant, though some fluorescence was observed in the lysate pellet.

Example 5—Ni-NTA Chromatography of Fresno-p5-21

The lysate supernatant from Example 4 containing Fresno-p5-21 was mixed with 0.5 ml of settled NiNTA resin (5-Prime, Hilden, Germany) and was mixed by gentle rotation for 2 hours at 4° C. The resin was then poured into a small gravity-fed chromatography column. Red color from the lysate supernatant adhered to the column, turning it a reddish-purple color. The column was washed with 5 column volumes of 50 mM sodium phosphate pH 7.4, 200 mM NaCl. The protein was then eluted with 250 mM imidazole+ 100 mM NaCl, pH 7.5. Upon elution, the red color was released from the column, generating a red eluate. The column reverted to its normal blue color. This indicates that the fluorescent protein could be purified by NiNTA chromatography. Since the bioactive peptide is between the fluorescent protein and the polyhistidine purification tag, it is inferred that the eluted protein includes the harpin peptide sequence.

Example 6—Hypersensitive Response Testing of Fresno-p5-21 Purified from *B. subtilis*

The production and purification procedure of Examples 4 and 5 were scaled up to 1 L to produce a quantity of protein appropriate for hypersensitive response elicitation in tobacco leaves.

Briefly, 1 L of LB culture media was supplemented with 10 ug/ml Kanamycin and cells were grown as in Example 3 for 2 days in a baffled flask. Cells were harvested at 6000 g for 20 minutes at 4° C. Culture supernatant was removed from the cells and the cells were resuspended in 20 ml of Bugbuster Protein Extraction Reagent supplemented with 50 ug/ml lysozyme. The sample was gently rocked at room temperature for 30 minutes and then frozen on liquid nitrogen and stored at −80° C.

The sample was thawed on ice and a 1/50 volume of 500 mM imidazole was added for a final concentration of 10 mM imidazole. 8 ml of the sample was mixed with 2 ml of settled Ni-NTA agarose resin (5-Prime) end-over-end for 2 hours at 4° C. The column was then settled for 20 minutes and allowed to flow by gravity. The flowthrough was collected. The resin was washed with 5 column volumes of 50 mM sodium phosphate, 15 mM imidazole, 200 mM NaCl. Finally, the protein was eluted with 250 mM imidazole, pH 7.5. The protein eluted from the resin was further desalted using centrifugal filtration columns (EMD Millipore, 10 kDa molecular weight cutoff), replacing the imidazole buffer with 10 mM sodium phosphate. A 1 ml sample of protein was generated. The protein concentration was quantified by UV/Vis spectroscopy using a Nanodrop 2000 (Thermo Fisher Scientific, Waltham, Mass., USA). The spectrum included peaks at 280 nm (A=0.084 for 1 cm path) and 555 nm (A=0.045 for 1 cm path). Based on a theoretical $\varepsilon 280=24360$ $1/(M*cm)$ and a molecular weight of 29283 Da, the protein concentration was about 10 ug/ml.

This protein solution was infused into tobacco leaves for a hypersensitive response test as previously described The protein solution caused lesions after 2 days at a 1× concentration and a 2× dilution typical of HR. This result indicates that the recombinant harpin peptide produced from *Bacillus subtilis* is biologically active in plants.

Example 7—Application of *B. subtilis* Expressing Fresno-p5-21 to Plants Via Foliar Spray Harpin proteins and *Bacillus subtilis* have separately been shown to improve plant health when applied as a leaf spray. It is believed that a foliar application of *Bacillus subtilis* expressing Fresno-p5-21 will cause multiple beneficial effects. The recombinant *Bacillus subtilis* will be supplied as a liquid product of an industrial-scale bacterial fermentation at a concentration of at least $1 \times 10^8$ CFU/mL. At this concentration, the solution will be sprayed directly onto the plant. (Higher concentration formulations can be sold as a concentrate which would be diluted by the end user prior to application.)

Ideally, the plants will be treated before the onset of disease symptoms during the early growth stage of life (3-6 leaves). The plants will not be watered for 4 hours after application and the application will not be carried out within 4 hours of rainfall. In addition, the application site will have a minimum of airflow to prevent significant drift of the sprayed liquid. The liquid will be sprayed directly onto plant leaves until the leaf surfaces are dripping.

Positive and negative controls include: foliar spray with water, foliar spray with an aqueous solution containing P5-21, and foliar spray with a comparable CFU/mL of Subtilex® NG (*Bacillus subtilis* biological inoculant) available from BASF.

The resulting plants will be evaluated for one or more of the following effects: enhanced growth (such as wet and dry root mass), nematode resistance, and drought resistance.

Example 8—Application of *B. subtilis* Expressing Fresno-p5-21 to Plants Via Root Drench

*Bacillus subtilis* is a soil-dwelling microbe and harpin peptide application has been shown to affect root morphology. It is believed a root drench application of *Bacillus subtilis* expressing Fresno-p5-21 will cause multiple beneficial effects. As in Example 7, above, the *Bacillus subtilis* expressing Fresno-p5-21 is industrially produced. For this application, a solution of at least $1 \times 10^9$ CFU/mL will be used. Ideally, the solution will be applied at the time of seed planting or soon after germination. As above, the application will be carried out when the soil is dry and rain is not expected.

This solution will be applied directly to dry soil within 4 inches of the plant stem or the seed. Application will continue until the soil is saturated or the bacterial culture begins to run off.

Positive and negative controls include: root drench with water, root drench with an aqueous solution containing P5-21, and root drench with a comparable CFU/mL of Subtilex® NG (*Bacillus subtilis* biological inoculant) available from BASF.

The resulting plants will be evaluated for one or more of the following effects: enhanced growth (such as wet and dry root mass), nematode resistance, and drought resistance. A comparison of the results following foliar spray in Example 7 and root drench in Example 8 will identify the best treatment(s) for the plants.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed:

1. A recombinant host cell comprising a transgene that comprises a promoter-effective nucleic acid molecule operably coupled to a nucleic acid molecule that encodes a plant effector polypeptide, wherein the recombinant host cell is a microbe having an endogenous gene that imparts a first benefit to a plant grown in the presence of the recombinant microbe and the plant effector polypeptide imparts a second benefit to the plant grown in the presence of the recombinant microbe, wherein said first benefit and said second benefit are distinct, and wherein the encoded plant effector polypeptide either:

(i) comprises the amino acid sequence of (L/M) XXLLXXLLXXLL (SEQ ID NO: 21) and includes up to 11 additional amino acids at the N-terminal end thereof, up to 10 additional amino acids at the C-terminal end thereof, or both, wherein X at position 2 is A, S, T, G, D, isoD, E, γ-glutamate, Q, or N;

X at position 3 is Q, A, S, T, G, D, isoD, E, γ-glutamate, or N;

X at position 6 is A, S, T, G, D, isoD, E, γ-glutamate, Q, or N;

X at position 7 is Q, A, S, T, G, D, isoD, E, γ-glutamate, or N;

X at position 10 is K, A, S, T, G, D, isoD, E, γ-glutamate, Q, or N; and

X at position 11 is S, A, T, G, D, isoD, E, γ-glutamate, Q, or N; or (ii) consists of the amino acid sequence of XXXXXXXXXXX(L/M)XXLLXXLLXXLLXXX (SEQ ID NO: 49), wherein X at position 1 is optional and, when present, is selected from Q, S, E, γ-glutamate, A, T, G, D, isoD, N, K, or R;

X at position 2 is optional and, when present, is selected from Q, S, E, γ-glutamate, A, T, G, D, isoD, N, K, or R;

X at position 3 is optional and, when present, is selected from P, Q, S, E, γ-glutamate, A, T, G, D, isoD, N, K, or R;

X at position 4 is optional and, when present, is selected from I, Q, S, E, γ-glutamate, A, T, G, D, N, isoD, K, or R;

X at position 5 is optional and, when present, is selected from D, isoD, S, E, γ-glutamate, A, T, G, N, Q, K, or R;

X at position 6 is optional and, when present, is selected from R, Q, S, E, γ-glutamate, A, T, G, D, isoD, N, or K;

X of position 7 is optional and, when present, is selected from Q, S, E, γ-glutamate, A, T, G, D, isoD, N, K, or R;

X at position 8 is optional and, when present, is selected from T, Q, S, E, γ-glutamate, A, G, D, isoD, N, K, or R;

X at position 9 is optional and, when present, is selected from I, Q, S, E, γ-glutamate, A, T, G, D, isoD, N, K, or R;

X at position 10 is optional and, when present, is selected from E, γ-glutamate, Q, S, A, T, G, D, isoD, N, K, or R;

X at position 11 is optional and, when present, is selected from Q, S, E, γ-glutamate, A, T, G, D, isoD, N, K, or R;

X at position 13 is A, S, T, G, D, isoD, E, γ-glutamate, Q, or N;

X at position 14 is Q, A, S, T, G, D, isoD, E, γ-glutamate, or N;

X at position 17 is A, S, T, G, D, isoD, E, γ-glutamate, Q, or N;

X at position 18 is Q, A, S, T, G, D, isoD, γ-glutamate, or N;

X at position 21 is K, A, S, T, G, D, isoD, E, γ-glutamate, Q, or N;

X at position 22 is S, A, T, G, D, isoD, E, γ-glutamate, Q, or N;

X at position 25 is optional and, when present, is selected from S, A, T, G, D, isoD, E, γ-glutamate, Q, or N;

X at position 26 is optional and, when present, is selected from P, S, A, T, G, D, isoD, E, γ-glutamate, Q, or N; and X at position 27 is optional and, when present, is selected from Q, S, A, T, G, D, isoD, E, γ-glutamate, or N.

2. The recombinant host cell according to claim 1, wherein the microbe is a bacterium.

3. The recombinant host cell according to claim 1, wherein the microbe is a fungus.

4. The recombinant host cell according to claim 1, wherein the transgene is stably integrated into the genome of the microbe.

5. The recombinant host cell according to claim 1, wherein the transgene is present in an expression vector.

6. The recombinant host cell according to claim 1, wherein the recombinant microbe is epiphytic.

7. The recombinant host cell according to claim 1, wherein the recombinant microbe is endophytic.

8. The recombinant host cell according to claim 1, wherein the first benefit comprises providing nutrition to a plant, producing plant hormone analogs that stimulate growth or reduce stress signaling, or competing with pathogenic organisms.

9. The recombinant host cell according to claim 1, wherein the second benefit comprises disease resistance, growth enhancement, tolerance and resistance to biotic stressors, tolerance to abiotic stress, desiccation resistance for cuttings removed from ornamental plants, post-harvest disease resistance or desiccation resistance to fruit or vegetables harvested from plants, and/or improved longevity of fruit or vegetable ripeness for fruit or vegetables harvested from plants.

10. A composition comprising a plurality of recombinant host cells according to claim 1.

11. The composition according to claim 10, wherein the composition is in the form of a dry powder.

12. The composition according to claim 11, wherein the dry powder comprises a carrier and the recombinant host cell.

13. The composition according to claim 10, wherein the composition is in the form of an aqueous solution or suspension.

14. The composition according to claim 10, wherein the composition comprises a mixture of two or more different recombinant host cells.

15. A mixture comprising one or more plant seeds and a composition according to claim 10.

16. A method for treating plant seeds comprising:
providing one or more plant seeds; and
applying to the provided one or more plant seeds a recombinant host cell according to claim 1.

17. The method according to claim 16, wherein said applying comprises mixing a dry powder comprises the recombinant host cells with the one or more plants seeds.

18. The method according to claim 16, wherein said applying comprises soaking or spraying the one or more plant seeds with an aqueous solution or suspension comprising the recombinant host cells.

19. A method for treating plants comprising:
providing one or more plants; and
applying to the provided one or more plants a recombinant host cell according to claim 1.

20. The method according to claim 19, wherein said applying comprises spraying the one or more plants with an aqueous solution or suspension comprising the recombinant host cells.

21. The method according to claim 19, wherein said applying comprises dusting the one or more plants with a dry powder comprising the recombinant host cells.

22. A method for treating plants comprising:
  applying to a locus where plants are being grown or will be grown a recombinant host cell according to claim 1 and
  growing one or more plants at the locus where the recombinant host cell is applied.

23. The method according to claim 22, wherein the recombinant host cell is applied prior to planting seeds or one or more seedlings at the locus.

24. The method according to claim 22, wherein the recombinant host cell is applied after planting seeds or one or more seedlings at the locus.

25. The method according to claim 22, wherein the recombinant host cell is applied to the locus while plants are being grown at the locus.

26. The method according to claim 22, wherein the locus comprises artificial or natural soil, a polymer growth medium, or a hydroponic growth medium.

27. A method of imparting disease resistance to plants comprising:
  applying an effective amount of a recombinant host cell according to claim 1 to a plant or plant seed or the locus where the plant is growing or will be grown, wherein said applying is effective to impart disease resistance to the plant.

28. A method of enhancing plant growth comprising:
  applying an effective amount of a recombinant host cell according to claim 1 to a plant or plant seed or the locus where the plant is growing or will be grown, wherein said applying is effective to enhance plant growth.

29. A method of increasing a plant's tolerance to biotic stress comprising:
  applying an effective amount of a recombinant host cell according to claim 1 to a plant or plant seed or the locus where the plant is growing or will be grown, wherein said applying is effective to increase the plant's tolerance to biotic stress factors selected from the group consisting of insects, arachnids, nematodes, weeds, and combinations thereof.

30. A method of increasing a plant's tolerance to abiotic stress comprising:
  applying an effective amount of a recombinant host cell according to claim 1 to a plant or plant seed or the locus where the plant is growing or will be grown, wherein said applying is effective to increase the plant's tolerance to abiotic stress factors selected from the group consisting of salt stress, water stress, ozone stress, heavy metal stress, cold stress, heat stress, nutritional stress, and combinations thereof.

31. A recombinant host cell comprising a transgene that comprises a promoter-effective nucleic acid molecule operably coupled to a nucleic acid molecule that encodes a plant effector polypeptide, wherein the recombinant host cell is a microbe having an endogenous gene that imparts a first benefit to a plant grown in the presence of the recombinant microbe and the plant effector polypeptide imparts a second benefit to the plant grown in the present of the recombinant microbe, wherein said first benefit and said second benefit are distinct, and wherein the encoded plant effector polypeptide has the amino acid sequence consisting essentially of:

| Peptide Name | Peptide Amino Acid Sequence | Sequence Identifier |
|---|---|---|
| P18 | QQPIDRQTIEQMAQLLAQLLKSLLSPQ | (SEQ ID NO: 25) or |
| K/R→E P18 variant | QQPIDEQTIEQMAQLLAQLLESLLSPQR | (SEQ ID NO: 44). |

* * * * *